(12) United States Patent
Alemparte-Gallardo et al.

(10) Patent No.: US 10,774,096 B2
(45) Date of Patent: *Sep. 15, 2020

(54) 4-SUBSTITUTED BENZOXABOROLE COMPOUNDS AND USES THEREOF

(71) Applicants: GLAXOSMITHKLINE INTELLECTUAL PROPERTY (NO.2) LIMITED, Brentford, Middlesex (GB); ANACOR PHARMACEUTICALS, INC., Palo Alto, CA (US)

(72) Inventors: Carlos Alemparte-Gallardo, Tres Cantos (ES); Michael Richard Kevin (Dickon) Alley, Palo Alto, CA (US); David Barros-Aguirre, Tres Cantos (ES); Ilaria Giordano, Tres Cantos (ES); Vincent Hernandez, Palo Alto, CA (US); Xianfeng Li, Palo Alto, CA (US); Jacob J. Plattner, Palo Alto, CA (US)

(73) Assignees: GLAXOSMITHKLINE INTELLECTUAL PROPERTY (NO.2) LIMITED, Brentford, Middlesex (GB); ANACOR PHARMACEUTICALS, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/550,693

(22) PCT Filed: Feb. 12, 2016

(86) PCT No.: PCT/IB2016/050775
§ 371 (c)(1),
(2) Date: Aug. 11, 2017

(87) PCT Pub. No.: WO2016/128948
PCT Pub. Date: Aug. 18, 2016

(65) Prior Publication Data
US 2018/0044353 A1 Feb. 15, 2018

(30) Foreign Application Priority Data

Feb. 12, 2015 (EP) .................................... 15382054
Feb. 12, 2015 (EP) .................................... 15382055
Feb. 12, 2015 (EP) .................................... 15382056

(51) Int. Cl.
*C07F 5/02* (2006.01)
*A61K 31/69* (2006.01)
*A61K 45/06* (2006.01)

(52) U.S. Cl.
CPC .............. *C07F 5/025* (2013.01); *A61K 31/69* (2013.01); *A61K 45/06* (2013.01); *C07B 2200/13* (2013.01)

(58) Field of Classification Search
CPC ....................................................... C07F 5/025
(Continued)

(56) References Cited

U.S. PATENT DOCUMENTS 7,205,425 B2   4/2007   Shibasaki et al.
7,446,236 B2   11/2008  Naud et al.
(Continued)

FOREIGN PATENT DOCUMENTS

WO   WO 2006/096131 A1   9/2006
WO   WO 2008/157726 A1   12/2008
(Continued)

OTHER PUBLICATIONS

King, Med Chem: Principle and Practice (1994), pp. 206-208.*
Adamczyk-Woźniak et al., "Benzoxaboroles—Old compounds with new applications," J. Organometallic Chem., vol. 694, Issue 22, (Available Online Jul. 12, 2009), pp. 3533-3541.
International Search Report issued in PCT/IB2016/050775 (PCT/ISA/210), dated Apr. 6, 2016.
Written Opinion of the International Searching Authority issued in PCT/IB2016/050775 (PCT/ISA/237), dated Apr. 6, 2016.
Hernandes et al., "Halogen Atoms in the Modern Medicinal Chemistry: Hints for the Drug Design," Current Drug Targets, vol. 11, No. 3, Mar. 2010, pp. 303-314.
U.S. Office Action issued in co-pending U.S. Appl. No. 15/550,658 and dated Jul. 6, 2018.
(Continued)

*Primary Examiner* — Taofiq A Solola
(74) *Attorney, Agent, or Firm* — Dority & Manning, P.A.

(57) ABSTRACT

Substituted benzoxaboroles whose structure comprises Formula (III), wherein $R^3$ is selected from —$CH_3$, —$CH_2CH_3$, —$CH_2$=$CH_2$, —$CH_2CH_2CH_3$, —$CH(CH_3)_2$, —$CH_2CH_2$=$CH_2$, and cyclopropyl, $R^1$ and $R^2$ are each independently selected from H, —$CH_3$, —$CH_2CH_3$, —$CH_2CH_2CH_3$, and —$CH(CH_3)_2$; compositions containing such compounds, their use in therapy, including their use as anti-mycobacterial agents, for example in the treatment of a mycobacterial infection in a mammal, and methods for the preparation of such compounds, are provided.

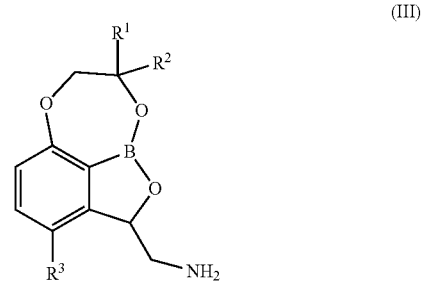

(III)

25 Claims, 5 Drawing Sheets

(58) Field of Classification Search
USPC .......................................................... 549/213
See application file for complete search history.

(56) References Cited

U.S. PATENT DOCUMENTS

| | | |
|---|---|---|
| 7,816,344 B2 | 10/2010 | Baker et al. |
| 8,530,452 B2 | 9/2013 | Gordeev et al. |
| 8,703,742 B2 | 4/2014 | Hernandez et al. |
| 9,243,003 B2 | 1/2016 | Conde et al. |
| 2009/0227541 A1 | 9/2009 | Baker et al. |
| 2010/0048570 A1 | 2/2010 | Kim et al. |
| 2012/0115813 A1 | 5/2012 | Hernandez et al. |
| 2013/0035501 A1 | 2/2013 | Conde et al. |
| 2013/0064783 A1 | 3/2013 | Baker et al. |
| 2013/0165411 A1 | 6/2013 | Gordeev et al. |
| 2016/0168167 A1 | 6/2016 | Kim et al. |

FOREIGN PATENT DOCUMENTS

| | | |
|---|---|---|
| WO | WO 2008157726 | 12/2008 |
| WO | WO 2011/127143 A1 | 10/2011 |
| WO | WO 2012/033858 A2 | 3/2012 |
| WO | WO 2013/093615 A1 | 6/2013 |
| WO | WO 2015/016558 A1 | 2/2015 |
| WO | WO 2015/021396 A2 | 2/2015 |
| WO | WO 2015021396 | 2/2015 |

OTHER PUBLICATIONS

Vippagunta et al., "Crystalline solids", Elsevier Science B.V., Advanced Drugs Delivery Reviews 48 (2001) pp. 3-26.

* cited by examiner

FIGURE 2

US 10,774,096 B2

4-SUBSTITUTED BENZOXABOROLE COMPOUNDS AND USES THEREOF

FIELD OF THE INVENTION

This invention relates to compounds, compositions containing them, their use in therapy, including their use as anti-mycobacterials, for example in the treatment of tuberculosis, and methods for the preparation of such compounds.

JOINT RESEARCH AGREEMENT

The subject matter in the instant application was developed by or on behalf of the applicants in a joint research agreement, within the meaning of 35 U.S.C. § 100(h) and § 1.9(e), that was in effect on or before the effective filing date of the claimed invention, and the subject matter was made as a result of activities undertaken within the scope of this joint research agreement.

BACKGROUND OF THE INVENTION

*Mycobacterium* is a genus in the class of bacteria called Actinobacteria with its own distinct family known as Mycobacteriacae. *Mycobacterium* contains various obligate and opportunistic pathogens of animals, which may also be transmitted to humans and cause disease in humans, thus exhibiting a considerable zoonotic potential. During the past few decades, members of the *Mycobacterium avium-intracellulare* complex (MAIC) emerged as pathogens of human diseases, including lymphadenitis in children, pulmonary tuberculosis-like disease, and disseminated infections (occurring predominantly in immunocompromised persons, particularly AIDS patients). Similarly, important animal diseases result from infections in an animal by members of this group, e.g., avian tuberculosis and *paratuberculosis* in ruminants. MAIC includes *M. intracellulare* and 4 subspecies of *M. avium*, namely, *M. avium* subsp. *avium*, *M. avium* subsp. *hominissuis*, *M. avium* subsp. *silvaticum*, and *M. avium* subsp. *paratuberculosis*. Whereas members of the *M. tuberculosis* complex are transmitted by direct host contact, MAIC species are acquired predominantly from environmental sources, including soil, water, dust, and feed.

*Mycobacterium tuberculosis* (MTB) is a small aerobic non-motile high-GC *bacillus* with an "outer-membrane" that is unusually thick, "waxy," hydrophobic, rich in mycolic acids, and extremely impermeable, making mycobacterium infections difficult to treat. One third of the world's population is thought to be infected (including latent MTB), but this number increases to upwards of 80% of the population in many Asian and African countries. If untreated, the death rate from active MTB infections is more than 50%. In addition, the combination of HIV and MTB is deadly and increasing numbers of MTB strains are becoming resistant to standard of care drugs; approximately 300,000 new cases of multidrug resistant (MDR) *M. tuberculosis* are reported each year. Multidrug resistant (MDR) *M. tuberculosis* are resistant to isoniazid and rifampicin, and extensive drug resistant (XDR) *M. tuberculosis* are also resistant to at least one quinolone and one aminoglycoside. As can be seen in FIG. 1, XDR *M. tuberculosis* has been reported across much of the globe.

Add to these issues the ease of transmission, as shown in FIG. 2, the globalization of travel, and the ongoing relocation and emigration of many segments of the world's population and it is apparent that MTB is becoming a global crisis.

Synthetic drugs for treating tuberculosis (TB) have been available for over half a century, but incidences of the disease continue to rise world-wide. More than 2 billion people are currently infected with *M. tuberculosis*, most being latent cases, and it is estimated that over 9 million new cases occur each year, worldwide, resulting in from 1.7 to nearly 2 million deaths per year. In 2004 alone approximately 24,500 new infections and close to 5,500 deaths were recorded, each day. See Zignol, M et al., M. Surveillance of anti-tuberculosis drug resistance in the world: an updated analysis, 2007-2010. Bull. World Health Organ 2012, 90 (2), 111-119D) Co-infection with HIV is driving the increase in incidence (Williams, B. G.; Dye, C. Science, 2003, 301, 1535) and the cause of death in 31% of AIDS patients in Africa can be attributed to TB. See Corbett, E. L et al., *Arch. Intl. Med.*, 2003, 163, 1009, Septkowitz, A et al., *Clin. Microbiol. Rev.* 1995, 8, 180).

The limitations of tuberculosis therapy and prevention are well known. The current available vaccine, BCG was introduced in 1921 and fails to protect most people past childhood. According to a 2006 report—"International Standards for Tuberculosis Care", a document developed by the Tuberculosis Coalition for Technical Assistance (TBCTA) which partners include Centers for Disease Control, American Thoracic Society, Tuberculosis Foundation, KNCV, the World Health Organization and the International Union Against Tuberculosis and Lung Disease—patients who do become infected with active disease currently endure two months of combination therapy with medicines introduced between 50 and 60 years ago—isoniazid (1952), rifampin (1963), pyrazinamide (1954) and ethambutol (1961)—followed by another 4 months of isoniazid and rifampin (also known as rifampicin). Alternatively the continuation phase could include Isoniazid and ethambutol for six months when adherence cannot be assessed, but according to this report, a longer continuation phase is associated with a higher rate of failure and relapse, especially in patients with HIV infection. Moreover, as detailed in this report, the doses of antituberculosis drugs used should conform to international recommendation and fixed-dose combinations of two (isoniazid and rifampicin), three (isoniazid, rifampicin, and pyrazinamide), and four (isoniazid, rifampicin, pyrazinamide, and ethambutol) drugs are highly recommended, especially when it is not possible to monitor the patient to ensure the treatment is ingested.

Daily dosing is required in these treatment phases and poor compliance drives the emergence and spread of multidrug-resistant strains, which are challenging to treat. Shorter courses of more active agents which can be taken less frequently and which present a high barrier to the emergence of resistance, i.e. agents which are effective against multidrug resistant strains of TB (MDR-TB), are urgently required. A March 2013 report (http://www.aidsmap.com/Once-weekly-continuation-phase-TB-treatment-equals-standard-of-care/page/2589498/) suggests that a two-drug combination of rifapentine (a long-acting derivative of rifampicin) with moxifloxacin (a fluoroquinolone antibiotic that has not been used previously in TB treatment) can allow tuberculosis (TB) treatment to be taken once-weekly during the four-month continuation phase and achieves the same standard of care as the traditional continuation treatment of daily treatment with isoniazid and rifampin. Such a treatment phase would allow treatment supervision to extend throughout the continuation phase, increasing adherence. However, moxifloxacin is not yet approved for treatment of TB, and the once-weekly treatment protocol is not yet endorsed or approved as an alternative standard of care treatment—guideline panels at international and national levels will need to review the published evidence to determine if this alternative continuation treatment protocol should be recommended and adopted. In addition, rifapentine is expensive, and interactions between rifapentine and antiretroviral drugs in the non-nucleoside reverse transcriptase inhibitor (NNRTI) and protease inhibitor classes may prevent its use in TB patients who are also HIV positive and taking antiretroviral medicines. Thus, at present, the costs/benefits analysis of a continuation treatment with weekly rifapentine versus daily rifampicin is yet to be fully assessed.

The tuberculosis drug Sirturo™ (bedaquiline) was approved in the United States in late December 2012, and another, delamanid, is attempting to gain regulatory approval in the EU. However, both are reserved for drug-resistant tuberculosis, which accounts for just 5% of new cases. A 2007 Editorial and News Focus in Nature Medicine discusses many aspects of TB such as pathogenesis, epidemiology, drug discovery and vaccine development to date (Nature Medicine, 2007, Focus on Tuberculosis, Vol 13(3), pages 263-312), noting that 125 years after the anniversary of the discovery of Mycobacterium tuberculosis, more than one-third of people in the world are infected with M. tuberculosis, and of these, more than 1 in 10 will develop the disease known as tuberculosis, formerly known as consumption, in their lifetime.

When coupled with the emergence of multi-drug resistant strains of Mycobacterium tuberculosis (MDR-TB), the scale of the problem is amplified. The global rise of bacteria and other microorganisms resistant to antibiotics and antimicrobials in general, poses a major threat. Deployment of massive quantities of antimicrobial agents into the ecosphere during the past 60 years has introduced a powerful selective pressure for the emergence and spread of antimicrobial-resistant pathogens. There is therefore a need to discover and develop new chemical entities to treat TB (recent leads are reviewed in: Grosset J H, Singer T G, Bishai W R. New Drugs for the Treatment of Tuberculosis: Hope and Reality. Int J Tuberc Lung Dis. 2012 August; 16(8):1005-14).

The present invention relates to certain substituted benzoxaboroles that show unexpected selectivity for inhibiting replication of Mycobacterium tuberculosis (M. tuberculosis) versus inhibition (toxicity) of human cells compared to other substituted benzoxaboroles, and exhibit sub-micromolar MIC values against mycobacterium species, particularly Mycobacterium tuberculosis and Mycobacterium tuberculosis complex (MTC), Mycobacterium avium and Mycobacterium avium complex (MAC) and Mycobacterium avium intracellulare complex (MAIC). Generally speaking, the benzoxaborole ring of substituted benzoxaborole has the following structure as shown below in Formula I, and may be characterized with the following substituent numbering system:

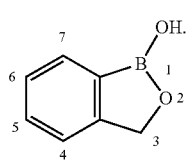

Formula I

It is understood that the International Union of Pure and Applied Chemistry (IUPAC) nomenclature may designate a different numbering system depending on substituents around the benzoxaborole ring. Throughout this application, unless the IUPAC name is given for a specific compound, the substituted benzoxaboroles disclosed herein may be named and numbered using the numbering scheme depicted in Formula I, shown above.

Boron-containing molecules such as benzoxaboroles that are useful as antimicrobials have been described previously, see e.g. "Benzoxaboroles—Old compounds with new applications" Adamczyk-Woźniak, A. et al., Journal of Organometallic Chemistry Volume 694, Issue 22, 15 Oct. 2009, Pages 3533-3541, and U.S. Pat. Pubs. US20060234981, US20070155699, WO2012033858, and US2013165411.

Certain substituted benzoxaboroles which are substituted at position 7 may form a tricyclic benzoxaborole compound (see US20090227541, US2013165411 and WO/KR2015/016558). Applicants have surprisingly found that certain substituted benzoxaboroles substituted at the 7 position (numbered using the numbering scheme depicted in Formula I, shown above) may also exist as an equilibrium mixture of a tricyclic benzoxaborole structure and a bicyclic benzoxaborole structure in aqueous solvents. When the resulting 7-substituted benzoxaborole is additionally substituted with an alkyl substituent at position 4 and an aminomethyl substituent at position 3 (numbered using the numbering scheme in Formula I, shown above), such substituted benzoxaboroles are surprisingly selective towards and effective against mycobacteria including M. tuberculosis. The selectivity observed is assessed by comparing MIC values for such compounds relative to inhibition (toxicity) of these compounds to human cells, compared to other substituted benzoxaboroles.

US20090227541 discloses a multitude of compounds, including two tricyclic benzoxaborole compounds with differing antibacterial activity against a panel of Gram negative bacteria (See e.g. Tables 1 and 2), but does not disclose tricyclic benzoxaborole compounds with alkyl substitution at the 4 position on the benzoxaborole ring (numbered using the numbering scheme depicted in Formula I, shown above). WO2012033858 discloses substituted benzoxaboroles with activity against Mycobacterium tuberculosis, including certain substituted benzoxaboroles (see e.g. Examples 1.A through 1.V), but again, no tricyclic benzoxaborole compound is disclosed with an alkyl substitution at the 4 position on the benzoxaborole ring (numbered using the numbering scheme depicted in Formula I, shown above). US2013165411 discloses tricyclic benzoxaborole compounds showing activity against Acinetobacter baumannii, Pseudomonas aeruginosa, Escherichia coli and Klebsiella pneumoniae (see Table 1), but notes specifically that the halogen-substituted tricyclic compounds investigated (Examples 17, 18 and 19) lack activity against A. baumannii, with MIC values ≥16 µg/µL antibacterial activity (see FIG. 1). In addition, nothing in US2013165411 suggests that any of the disclosed tricyclic benzoxaborole compounds are capable of existing as an equilibrium mixture of a tricyclic benzoxaborole structure and a bicyclic benzoxaborole structure in aqueous solvent conditions.

SUMMARY OF THE INVENTION

The inventors have surprisingly found that substituted benzoxaboroles as described herein show unexpected selectivity for inhibiting replication of Mycobacterium tuberculosis (M. tuberculosis) versus inhibition (toxicity) of human cells compared to other substituted benzoxaboroles. These substituted benzoxaboroles exhibit sub-micromolar MIC values against M. tuberculosis, which is comparable to or better than the MIC values for current therapies available for inhibiting *M. tuberculosis*. Further, in other embodiments, the substituted benzoxaboroles as described herein are envisioned for use in combination with current anti-tubercular compounds and are envisioned to achieve greater efficacy in treating animals, including humans, infected with *M. tuberculosis*.

Resistance remains an issue in the treatment of tuberculosis (TB) and one clinical strategy is to focus on early combination with other TB drugs and to expedite early assessment of the compound's efficacy in patients. Compounds whose structure comprises Formula III or Formula IIIa offer a unique opportunity to address the serious issues which arise during the treatment of TB, such as multi-drug resistance, extensive-drug resistance, reactivity and/or adverse interaction between therapeutic agents in a multi-drug combination, and treatment length, thereby addressing potential patient needs.

In certain embodiments of the present invention there is featured combinations of anti-tuberculosis agents and certain substituted benzoxaboroles, for use in the treatment of *Mycobacterium tuberculosis* infections in animals, including humans. In particular embodiments, such substituted benzoxaboroles are used, in combination with other known anti-tuberculosis agents, for treating an animal subject with a *Mycobacterium tuberculosis* infection, particularly in an animal subject that is additionally infected with a human retrovirus, in particular a human immunodeficiency virus (HIV).

In an exemplary embodiment, the invention is a compound as described herein, or a salt thereof, including a pharmaceutically acceptale salt there, or hydrate thereof.

In particular embodiments, the substituted benzoxaborole is a compound or a salt thereof, including a pharmaceutically acceptable salt thereof, whose structure comprises Formula III:

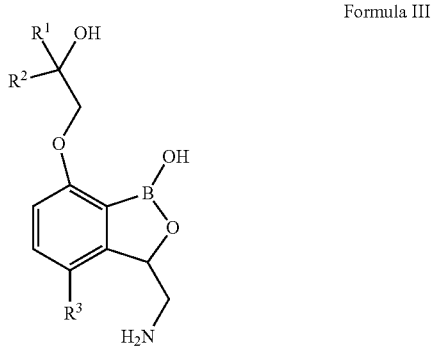

Formula III wherein $R^3$ is selected from —$CH_3$, —$CH_2CH_3$, —$CH_2$=$CH_2$, —$CH_2CH_2CH_3$, —$CH(CH_3)_2$, —$CH_2CH_2$=$CH_2$, or cyclopropyl; $R^1$ and $R^2$ are each independently selected from H, —$CH_3$, —$CH_2CH_3$, —$CH_2CH_2CH_3$, and —$CH(CH_3)_2$.

In particular embodiments, the substituted benzoxaborole may exist in an equilibrium, as indicated below, between a closed form (Formula II) and an open form (Formula III), in certain environments and/or solvents.

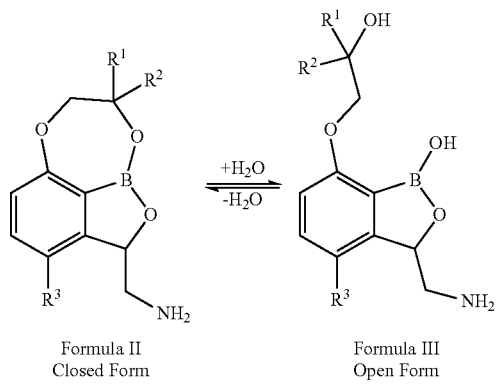

Formula II
Closed Form

Formula III
Open Form

In particular embodiments there is provided a compound whose structure comprises Formula III or a salt thereof, wherein $R^3$ is —$CH_3$ or —$CH_2CH_3$; $R^1$ and $R^2$ are each independently selected from H, —$CH_3$, —$CH_2CH_3$, —$CH_2CH_2CH_3$, and —$CH(CH_3)_2$.

In particular embodiments there is provided a compound whose structure comprises Formula III or a salt thereof, wherein $R^3$ is —$CH_3$ and $R^1$ and $R^2$ are as described herein. In particular embodiments there is provided a compound whose structure comprises Formula III or a salt thereof, wherein $R^3$ is —$CH_3$ and $R^1$ is H and $R^2$ is as described herein. In particular embodiments there is provided a compound whose structure comprises Formula III or a salt thereof, wherein $R^3$ is —$CH_3$ and $R^1$ is —$CH_3$ and $R^2$ is as described herein.

In particular embodiments there is provided a compound whose structure comprises Formula III or a salt thereof, wherein $R^3$ is —$CH_2CH_3$ and $R^1$ and $R^2$ are as described herein. In particular embodiments there is provided a compound whose structure comprises Formula III or a salt thereof, wherein $R^3$ is —$CH_2CH_3$ and $R^1$ and $R^2$ are as each independently H or —$CH_3$. In particular embodiments there is provided a compound whose structure comprises Formula III or a salt thereof, wherein $R^3$ is —$CH_2CH_3$ and $R^1$ is H and $R^2$ is —$CH_3$. In particular embodiments there is provided a compound whose structure comprises Formula III or a salt thereof, wherein $R^3$ is —$CH_2CH_3$ and $R^1$ is —$CH_3$ and $R^2$ is as described herein.

In particular embodiments there is provided a compound whose structure comprises Formula III or a salt thereof, wherein $R^3$ is —$CH_2CH_2CH_3$, and $R^1$ and $R^2$ are as described herein.

In particular embodiments there is provided a compound whose structure comprises Formula III or a salt thereof, wherein $R^3$ is —$CH(CH_3)_2$ and $R^1$ and $R^2$ are as described herein.

In particular embodiments there is provided a compound whose structure comprises Formula III or a salt thereof, wherein $R^3$ is —$CH_2CH_2CH_3$; $R^1$ and $R^2$ are each independently selected from H, —$CH_3$, and —$CH_2CH_3$.

In particular embodiments there is provided a compound whose structure comprises Formula III or a salt thereof, wherein $R^3$ is —$CH_2CH_2CH_3$ and $R^1$ and $R^2$ are each independently H or —$CH_3$ In particular embodiments there is provided a compound whose structure comprises Formula III or a salt thereof, wherein $R^3$ is —$CH(CH_3)_2$ and $R^1$ and $R^2$ are each independently selected from H, —$CH_3$, and —$CH_2CH_3$.

In particular embodiments there is provided a compound whose structure comprises Formula III or a salt thereof, wherein $R^3$ is —CH(CH$_3$)$_2$ and $R^1$ and $R^2$ are each independently H or —CH$_3$.

In particular embodiments there is provided a compound comprising a structure of Formula IIIa

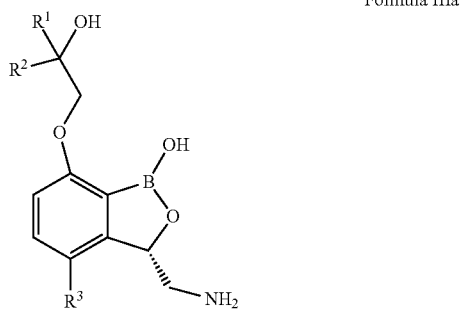

Formula IIIa wherein $R^3$ is —CH$_3$, —CH$_2$CH$_3$, —CH$_2$=CH$_2$, —CH$_2$CH$_2$CH$_3$, —CH(CH$_3$)$_2$, —CH$_2$CH$_2$=CH$_2$, or cyclopropyl and $R^1$ and $R^2$ are each independently selected from H, —CH$_3$, —CH$_2$CH$_3$, —CH$_2$CH$_2$CH$_3$, and —CH(CH$_3$)$_2$, or a salt thereof, including a pharmaceutically acceptable salt thereof.

In particular embodiments, the compound of Formula IIIa may exist in equilibrium, as indicated below, between a closed form (Formula IIa) and an open form (Formula IIIa), in certain environments and/or solvents.

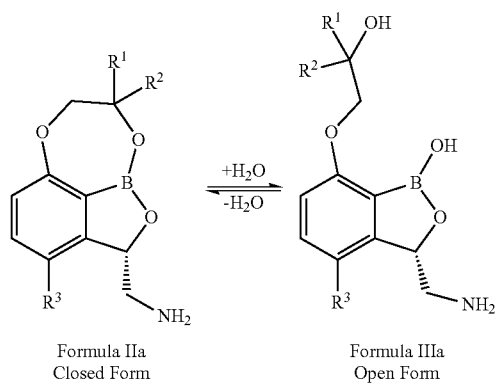

Formula IIa
Closed Form

Formula IIIa
Open Form

In particular embodiments, the compound of Formula IIIa may exist in the open form of Formula IIIa in the solid state. In particular embodiments there is provided a compound whose structure comprises Formula IIIa wherein $R^3$ is —CH$_3$, —CH$_2$CH$_3$, —CH$_2$=CH$_2$, —CH$_2$CH$_2$CH$_3$, —CH(CH$_3$)$_2$, —CH$_2$CH$_2$=CH$_2$, or cyclopropyl, and $R^1$ and $R^2$ are each independently selected from H, —CH$_3$, and —CH$_2$CH$_3$, or a pharmaceutically acceptable salt or hydrate thereof.

In particular embodiments there is provided a compound whose structure comprises Formula IIIa wherein $R^3$ is —CH$_3$, —CH$_2$CH$_3$, —CH$_2$=CH$_2$, —CH$_2$CH$_2$CH$_3$, —CH(CH$_3$)$_2$, —CH$_2$CH$_2$=CH$_2$, or cyclopropyl and $R^1$ and $R^2$ are each independently selected from H and —CH$_3$, or a pharmaceutically acceptable salt or hydrate thereof.

In particular embodiments there is provided a compound whose structure comprises Formula IIIa or a salt or hydrate thereof, wherein $R^3$ is —CH$_3$ and $R^1$ and $R^2$ are as described herein. In particular embodiments there is provided a compound whose structure comprises Formula IIIa or a salt or hydrate thereof, wherein $R^3$ is —CH$_3$ and $R^1$ is H and $R^2$ is as described herein. In particular embodiments there is provided a compound whose structure comprises Formula IIIa or a salt or hydrate thereof, wherein $R^3$ is —CH$_3$ and $R^1$ is —CH$_3$ and $R^2$ is as described herein.

In particular embodiments there is provided a compound whose structure comprises Formula IIIa or a salt or hydrate thereof, wherein $R^3$ is —CH$_2$CH$_3$ and $R^1$ and $R^2$ are as described herein. In particular embodiments there is provided a compound whose structure comprises Formula IIIa or a salt or hydrate thereof, wherein $R^3$ is —CH$_2$CH$_3$ and $R^1$ is H and $R^2$ is as described herein. In particular embodiments there is provided a compound whose structure comprises Formula IIIa or a salt or hydrate thereof, wherein $R^3$ is —CH$_2$CH$_3$ and $R^1$ is —CH$_3$ and $R^2$ is as described herein.

In particular embodiments there is provided a compound whose structure comprises Formula IIIa or a salt or hydrate thereof, wherein $R^3$ is —CH(CH$_3$)$_2$, and $R^1$ and $R^2$ are as described herein.

In particular embodiments there is provided a compound whose structure comprises Formula IIIa or a salt or hydrate thereof, wherein $R^3$ is —CH$_3$, and $R^1$ and $R^2$ are as described herein.

In particular embodiments there is provided a compound whose structure comprises Formula IIIa wherein $R^3$ is —CH$_3$ and $R^1$ and $R^2$ are each independently selected from H, —CH$_3$, —CH$_2$CH$_3$, —CH$_2$CH$_2$CH$_3$, and —CH(CH$_3$)$_2$, or a salt or hydrate thereof, including a pharmaceutically acceptable salt thereof.

In particular embodiments there is provided a compound whose structure comprises Formula IIIa wherein $R^3$ is —CH$_3$, and $R^1$ and $R^2$ are each independently selected from H, —CH$_3$, and —CH$_2$CH$_3$, or a salt or hydrate thereof, including a pharmaceutically acceptable salt thereof.

In particular embodiments there is provided a compound whose structure comprises Formula IIIa wherein $R^3$ is —CH$_3$, and $R^1$ and $R^2$ are each independently selected from H and —CH$_3$, or a salt or hydrate thereof, including a pharmaceutically acceptable salt thereof.

In particulate embodiments, compounds of Formula III and compounds of Formula IIIa as described herein exist as a hydrate as indicated by Formula IV or Formula IVa below:

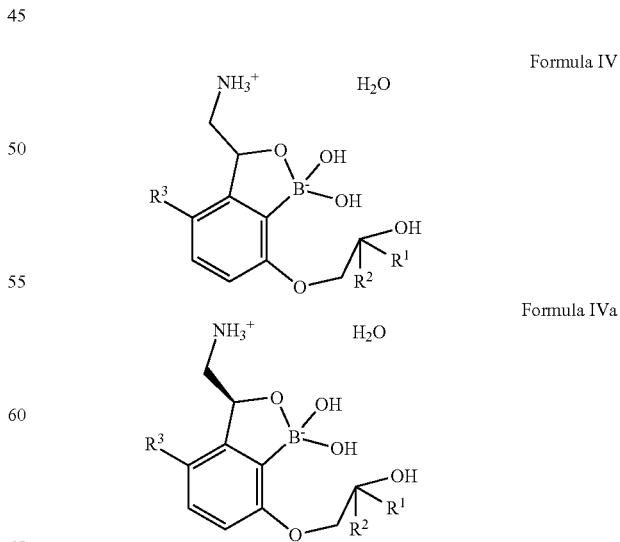

wherein $R^1$, $R^2$ and $R^3$ and are as described herein.

In particular embodiments, the substituted benzoxaborole comprises a structure of as indicated below:

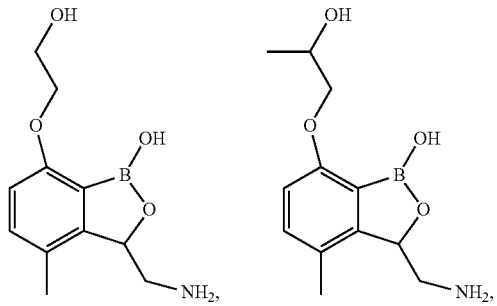

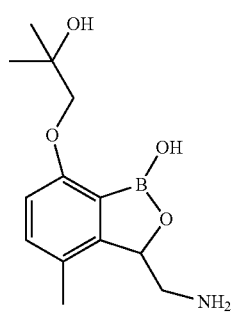

or a pharmaceutically acceptable salt thereof.

In particular embodiments, the substituted benzoxaborole is a compound comprising a structure of as indicated below:

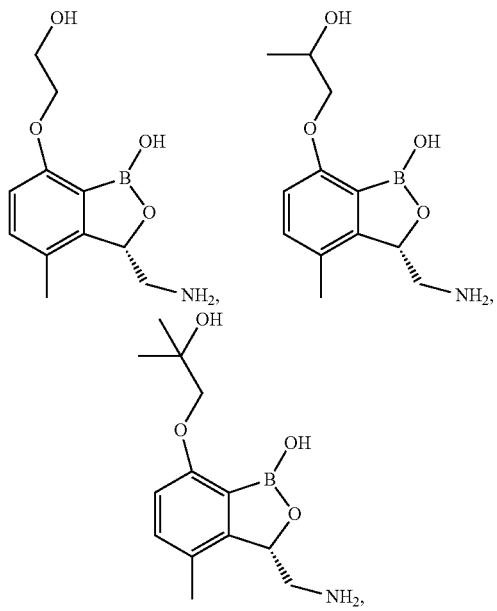

or a pharmaceutically acceptable salt thereof.

In other embodiments, the substituted benzoxaborole is a compound comprising a structure as indicated below:

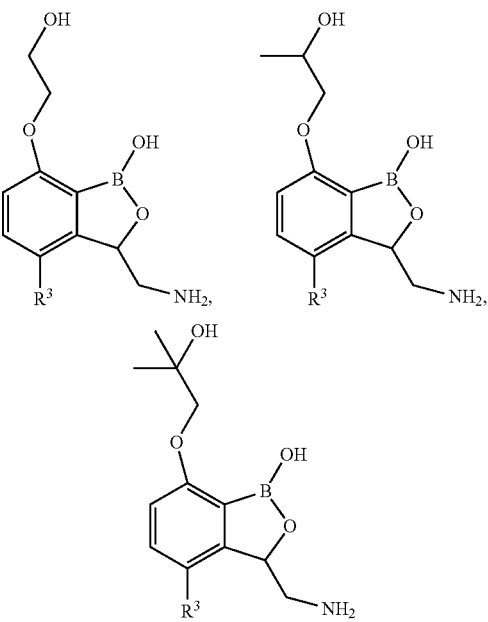

wherein $R^3$ is as defined herein, or a pharmaceutically acceptable salt thereof.

In other embodiments, the substituted benzoxaborole is a compound comprising a structure as indicated below:

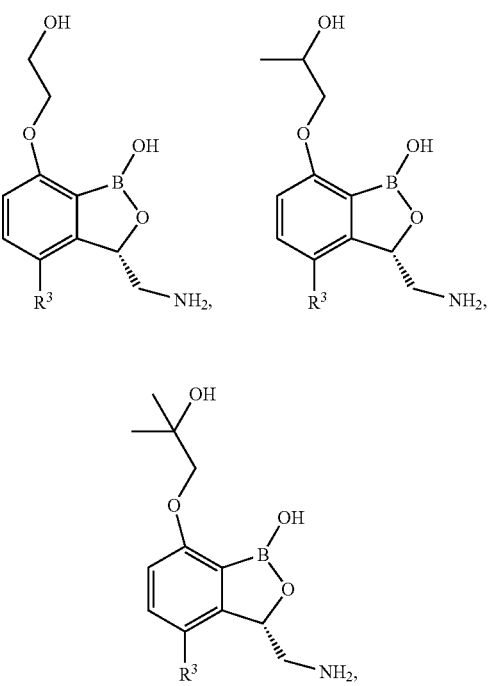

wherein $R^3$ is as defined herein, or a pharmaceutically acceptable salt thereof.

In still other embodiments, the substituted benzoxaborole is a compound comprising a structure as indicated below:

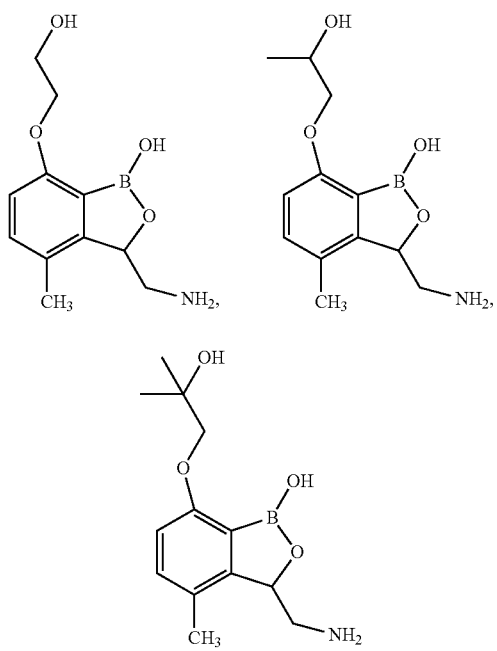

and a pharmaceutically acceptable salt thereof.

In still other embodiments, the substituted benzoxaborole is a compound comprising a structure as indicated below:

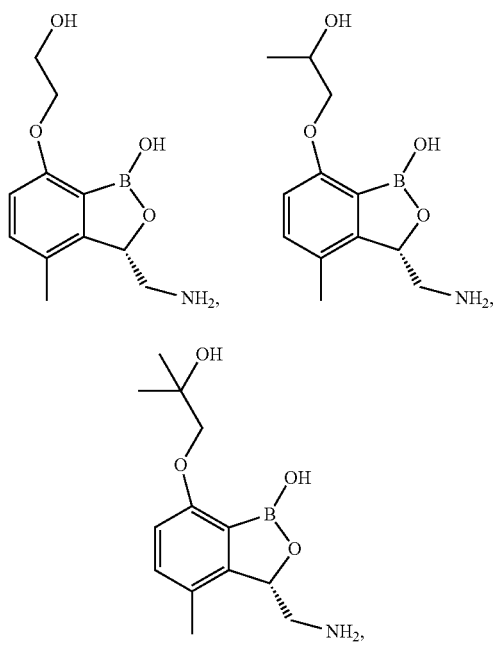

or a pharmaceutically acceptable salt thereof.

In another embodiment there is provided a compound, (S)-(3-methyl-7,8-dihydro-2H-1,6,9-trioxa-9a-borabenzo[cd]azulen-2-yl)methanamine, comprising a structure as indicated below:

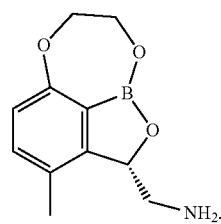 [SMILES: Cc1ccc2c3c1[C@@H](CN)OB3OCCO2]

In another embodiment there is provided a compound, (S)-(3-methyl-7,8-dihydro-2H-1,6,9-trioxa-9a-borabenzo[cd]azulen-2-yl)methanamine, comprising a structure as indicated below:

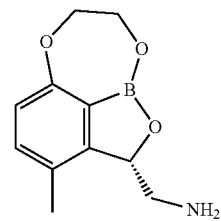 [SMILES: Cc1ccc2c3c1[C@@H](CN)OB3OCCO2]

or a pharmaceutically acceptable salt thereof.

Another embodiment provides a pharmaceutically acceptable salt of a compound, (S)-(3-methyl-7,8-dihydro-2H-1,6,9-trioxa-9a-borabenzo[cd]azulen-2-yl)methanamine, comprising a structure as indicated below:

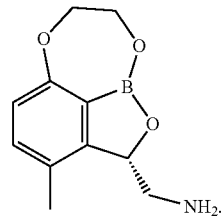 [SMILES: Cc1ccc2c3c1[C@@H](CN)OB3OCCO2]

Another embodiment provides a pharmaceutical composition comprising a pharmaceutically acceptable salt of a compound, (S)-(3-methyl-7,8-dihydro-2H-1,6,9-trioxa-9a-borabenzo[cd]azulen-2-yl)methanamine, wherein the compound comprises a structure as indicated below:

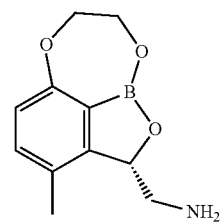 [SMILES: Cc1ccc2c3c1[C@@H](CN)OB3OCCO2]

together with at least one pharmaceutically acceptable excipient.

In yet another embodiment there is provided a compound, (S)-(3,8,8-trimethyl-7,8-dihydro-2H-1,6,9-trioxa-9a-borabenzo[cd]azulen-2-yl)methanamine, comprising a structure as indicated below:

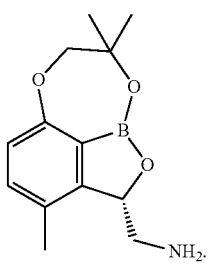 [SMILES: Cc1ccc2c3c1[C@@H](CN)OB3OC(C)(C)CO2]

Still another embodiment provides a compound, (S)-(3,8,8-trimethyl-7,8-dihydro-2H-1,6,9-trioxa-9a-borabenzo[cd]azulen-2-yl)methanamine, comprising a structure as indicated below:

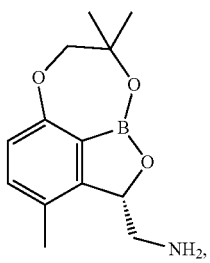 [SMILES: Cc1ccc2c3c1[C@@H](CN)OB3OC(C)(C)CO2]

or a pharmaceutically acceptable salt thereof.

Another embodiment provides a pharmaceutically acceptable salt of a compound, (S)-(3,8,8-trimethyl-7,8-dihydro-2H-1,6,9-trioxa-9a-borabenzo[cd]azulen-2-yl)methanamine, comprising a structure as indicated below:

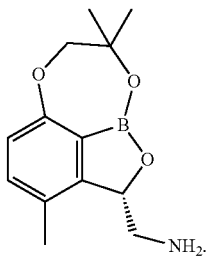 [SMILES: Cc1ccc2c3c1[C@@H](CN)OB3OC(C)(C)CO2]

Another embodiment provides a pharmaceutical composition comprising a compound, (S)-(3,8,8-trimethyl-7,8-dihydro-2H-1,6,9-trioxa-9a-borabenzo[cd]azulen-2-yl)methanamine, wherein the compound comprises a structure as indicated below:

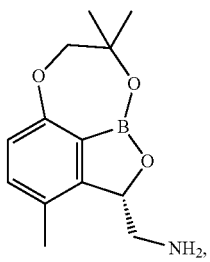 [SMILES: Cc1ccc2c3c1[C@@H](CN)OB3OC(C)(C)CO2]

together with at least one pharmaceutically acceptable excipient.

One embodiment provides a substituted benzoxaborole or a pharmaceutically acceptable salt thereof, comprising a structure whose IUPAC name is:
3-methyl-7,8-dihydro-2H-1,6,9-trioxa-9a-borabenzo[cd] azulen-2-yl)methanamine;
(S)-(3-methyl-7,8-dihydro-2H-1,6,9-trioxa-9a-borabenzo[cd]azulen-2-yl)methanamine;
3,8-dimethyl-7,8-dihydro-2H-1,6,9-trioxa-9a-borabenzo[cd]azulen-2-yl)methanamine;
((2S)-3,8-dimethyl-7,8-dihydro-2H-1,6,9-trioxa-9a-borabenzo[cd]azulen-2-yl)methanamine;
(3,8,8-trimethyl-7,8-dihydro-2H-1,6,9-trioxa-9a-borabenzo[cd]azulen-2-yl)methanamine;
(S)-(3,8,8-trimethyl-7,8-dihydro-2H-1,6,9-trioxa-9a-borabenzo[cd]azulen-2-yl)methanamine.

One embodiment provides a substituted benzoxaborole or a pharmaceutically acceptable a salt thereof, comprising a structure whose IUPAC name is:
3-(aminomethyl)-7-(2-hydroxyethoxy)-4-methylbenzo[c][1,2]oxaborol-1(3H)-ol;
(S)-3-(aminomethyl)-7-(2-hydroxyethoxy)-4-methylbenzo[c][1,2]oxaborol-1(3H)-ol
3-(aminomethyl)-7-(2-hydroxypropoxy)-4-methylbenzo[c][1,2]oxaborol-1(3H)-ol;
(3S)-3-(aminomethyl)-7-(2-hydroxypropoxy)-4-methylbenzo[c][1,2]oxaborol-1(3H)-ol;
3-(aminomethyl)-7-(2-hydroxy-2-methylpropoxy)-4-methylbenzo[c][1,2]oxaborol-1(3H)-ol;
(S)-3-(aminomethyl)-7-(2-hydroxy-2-methylpropoxy)-4-methylbenzo[c][1,2]oxaborol-1(3H)-ol.

In a related embodiment, the pharmaceutically acceptable salt is selected from hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like. In other related embodiments, the pharmaceutically acceptable salt is derived from organic acids including acetic acid, propionic acid, isobutyric acid, maleic acid, malonic acid, benzoic acid, succinic acid, suberic acid, fumaric acid, glucaronic acid, galacturonic acid, lactic acid, mandelic acid, phthalic acid, benzenesulfonic acid, p-tolylsulfonic acid, citric acid, tartaric acid, methanesulfonic acid, and the like. Still other related embodiments the pharmaceutically acceptable salt includes salts of amino acids such as arginate, lysinate, glycinate. In another embodiment, the pharmaceutically acceptable salt includes salts of acids, including salts of HCl and $H_2SO_4$.

In particular aspects of the invention, the compound of Formula III or Formula IIIa is a mixture of diastereomers. In other particular aspects of the invention, the compound of Formula III or Formula IIIa is a diastereomer. In other particular aspects of the invention, the compound of Formula III is a racemic mixture of enantiomers. In still other particular aspects of the invention, the compound of Formula III is a specific enantiomer. In particular aspects of the invention when $R^1$ and $R^2$ are both H or $CH_3$, the compound of Formula III or Formula IIIa has (S) stereochemistry at the chiral center at the 3-position on the benzoxaborole ring.

One embodiment provides a combination comprising: a first therapeutic agent wherein the first therapeutic agent is a compound as described herein, or a pharmaceutically acceptable salt thereof; optionally a second therapeutic agent; optionally a third therapeutic agent; optionally a fourth therapeutic agent; optionally a fifth therapeutic agent; and optionally a sixth therapeutic agent.

A related embodiment provides a combination as described wherein the optional second, third, fourth, fifth and sixth therapeutic agent is independently selected from isoniazid, rifampin, pyrazinamide, ethambutol, moxifloxacin, rifapentine, clofazimine, bedaquiline (TMC207), nitroimidazo-oxazine PA-824, delamanid (OPC-67683), an oxazolidinone such as linezolid, tedizolid, radezolid, sutezolid (PNU-100480), or posizolid (AZD-5847), EMB analogue SQ109, a benzothiazinone, a dinitrobenzamide or an antiviral agent including an antiretroviral agent.

A related embodiment provides a combination as described wherein the antiretroviral agents is zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, or darunavir.

Another embodiment of the invention provides a combination as described wherein the second, third, fourth, fifth and sixth therapeutic agent is selected from a therapeutic agent approved or recommended for the treatment of tuberculosis.

One embodiment of the present invention provides a pharmaceutical formulation comprising a first therapeutic agent, said first therapeutic agent being a therapeutically effective amount of a compound whose structure comprises Formula III or Formula IIIa according to any of the embodiments described herein or a pharmaceutically acceptable salt thereof. A related embodiment provides a combination as described herein and a pharmaceutically acceptable excipient, adjuvant or diluent. In another embodiment, the pharmaceutical formulation may further comprise a second therapeutic agent.

Another embodiment provides a method of killing mycobacteria and/or inhibiting replication of mycobacteria that causes disease in an animal, comprising contacting the mycobacteria with an effective amount of a compound whose structure comprises Formula III or Formula IIIa as described herein or a pharmaceutically acceptable salt thereof, so as to kill the mycobacteria and/or prevent the replication of the mycobacteria.

Another embodiment of the invention provides a method of treating a mycobacterium infection in an animal comprising: administering to the animal any one of: (i) a therapeutically effective amount of a compound whose structure comprises III or Formula IIIa as described herein or a pharmaceutically acceptable salt thereof; (ii) a therapeutically effective amount of a combination comprising a compound whose structure comprises Formula III or Formula IIIa as described herein or a pharmaceutically acceptable salt thereof; or (iii) a therapeutically effective amount of a pharmaceutical formulation comprising a compound whose structure comprises Formula III or Formula IIIa as described herein or a pharmaceutically acceptable salt thereof, so as to treat the mycobacterium infection in the animal.

In a further aspect, the invention provides a method of killing mycobacteria and/or inhibiting replication of mycobactera or a method of treating a mycobacterial infection in an animal such as livestock and pets, including cattle sheep, goats, dogs and cats, or a human, including an immunesuppressed human said method comprising: contacting the mycobactera with an effective amount of a compound whose structure comprises Formula III or Formula IIIa as described herein, thereby killing the mycobacteria and/or inhibiting replication of the mycobacteria, or said method comprising administering to the animal with the mycobacterial infection a therapeutically effective amount of a compound whose structure comprises Formula III or Formula IIIa, or a pharmaceutically acceptable salt thereof. In an exemplary embodiment, the compound of Formula III or compound of Formula IIIa is part of a pharmaceutical formulation described herein. In another exemplary embodiment, the contacting occurs under conditions which permit entry of the combination into the mycobacterium.

Another embodiment of the invention provides a method as described herein, wherein the mycobacteria is selected from *Mycobacterium tuberculosis*, *Mycobacterium avium* including subspecies (subsp.) *Mycobacterium avium* subsp. *avium*, *Mycobacterium avium* subsp. *hominissuis*, *Mycobacterium avium* subsp. *silvaticum*, and *Mycobacterium avium* subsp. *paratuberculosis*; *Mycobacterium kansasii*, *Mycobacterium malmoense*, *Mycobacterium simiae*, *Mycobacterium szulgai*, *Mycobacterium xenopi*, *Mycobacterium scrofulaceum*, *Mycobacterium abscessus*, *Mycobacterium chelonae*, *Mycobacterium haemophilum*, *Mycobacterium leprae*, *Mycobacterium marinum*, *Mycobacterium fortuitum*, *Mycobacterium parafortuitum*, *Mycobacterium gordonae*, *Mycobacterium vaccae*, *Mycobacterium bovis*, *Mycobacterium bovis* BCG, *Mycobacterium africanum*, *Mycobacterium canetti*, *Mycobacterium caprae*, *Mycobacterium microti*, *Mycobacterium pinnipedi*, *Mycobacterium leprae*, *Mycobacterium ulcerans*, *Mycobacterium intracellulare*, *Mycobacterium tuberculosis* complex. (MTC), *Mycobacterium avium* complex (MAC), *Mycobacterium avian-intracellulare* complex (MAIC), *Mycobacterium gordonae* clade; *Mycobacterium kansasii* clade; *Mycobacterium chelonae* clade; *Mycobacterium fortuitum* clade; *Mycobacterium parafortuitum* clade; and *Mycobacterium vaccae* clade.

Another embodiment provides a method of treating a mycobacterium infection in an animal comprising: administering to the animal any one of: (i) a therapeutically effective amount of a compound whose structure comprises Formula III or Formula IIIa as described herein or a pharmaceutically acceptable salt thereof; (ii) a therapeutically effective amount of a combination comprising a compound whose structure comprises Formula III or Formula IIIa as described herein or a pharmaceutically acceptable salt thereof; or (iii) a therapeutically effective amount of a pharmaceutical formulation comprising a compound whose structure comprises Formula III or Formula IIIa as described herein or a pharmaceutically acceptable salt thereof, so as to treat the mycobacterium infection in the animal, wherein the mycobacterium infection is a *M. tuberculosis* infection.

Another embodiment provides a compound whose structure comprises Formula III or Formula IIIa as described herein or a pharmaceutically acceptable salt thereof, for use in the treatment of a disease resulting from a mycobacterial infection in an animal, including a human. Another embodiment provides a compound as described herein, wherein the disease is selected from tuberculosis, leprosy, Johne's disease, Buruli or Bairnsdale ulcer, Crohn's disease, pulmonary disease or pulmonary infection. pneumonia, bursa, synovial, tendon sheaths, localized abscess, lymphadenitis, skin and soft tissue infections Lady Windermere syndrome, MAC lung disease, disseminated *Mycobacterium avium* complex (DMAC), disseminated *Mycobacterium avium intracellu-*

*lare* complex (DMAIC), hot-tub lung, MAC mastitis, MAC pyomyositis, *Mycobacterium avum paratuberculosis*, or granuloma, disease.

One embodiment provides the use of a compound whose structure comprises Formula III or Formula IIIa as described herein or a pharmaceutically acceptable salt thereof in the manufacture of a medicament for the treatment of mycobacterial infection in an animal.

Another embodiment provides a method of treating a disease resulting from a mycobacterial infection in an animal, particularly in a mammal, more particularly in a human, which method comprises administering to the animal in need of such treatment an effective amount of a compound Formula III or Formula IIIa as described herein or a pharmaceutically acceptable salt thereof. Another embodiment provides a method as described, wherein the disease is selected from tuberculosis, leprosy, Johne's disease, Buruli or Bairnsdale ulcer, Crohn's disease, pulmonary disease or pulmonary infection. pneumonia, bursa, synovial, tendon sheaths, localized abscess, lymphadenitis, skin and soft tissue infections Lady Windermere syndrome, MAC lung disease, disseminated *Mycobacterium avium* complex (DMAC), disseminated *Mycobacterium avium intracellulare* complex (DMAIC), hot-tub lung, MAC mastitis, MAC pyomyositis, *Mycobacterium avum paratuberculosis*, or granuloma disease.

Another embodiment provides a method of treating a mycobacterial infection in an animal, particularly in a mammal, which method comprises administering to the animal in need of such treatment a therapeutically effective amount of a compound described herein, or pharmaceutically acceptable salt thereof. Another embodiment provides a method of treating a mycobacterial infection in an animal, particularly a mammal, wherein the mycobacterial infection is *Mycobacterium tuberculosis*.

In one embodiment there is provided a pharmaceutical formulation comprising a first therapeutic agent, said first therapeutic agent being a therapeutically effective amount of a compound described herein or pharmaceutically acceptable salt thereof, and a pharmaceutically acceptable excipient, adjuvant or diluent.

More particularly, a pharmaceutical formulation is provided comprising a first therapeutic agent that is a compound whose structure comprises Formula III or Formula IIIa, said first therapeutic agent being a therapeutically effective amount of a compound as described herein or pharmaceutically acceptable salt thereof, in any embodiment as described herein; a pharmaceutically acceptable excipient, adjuvant or diluent; and a second therapeutic agent that is not a compound whose structure comprises Formula III or Formula IIIa. In related aspects, the pharmaceutical formulation comprises a first therapeutic agent that is a compound whose structure comprises Formula III or Formula IIIa as described herein, or a pharmaceutically acceptable salt thereof, and optionally comprises a second therapeutic agent that is not a compound whose structure comprises Formula III or Formula IIIa, and optionally comprises a third therapeutic agent, and optionally comprises a fourth therapeutic agent, and optionally comprises a fifth therapeutic agent, and optionally comprises a sixth therapeutic agent. In related aspects, the second, third, fourth, fifth and sixth therapeutic agent is an anti-mycobacterial agent other than a compound whose structure comprises Formula III or Formula IIIa. In related aspects, the second, third, fourth, fifth and sixth therapeutic agent is selected from isoniazid, rifampin, pyrazinamide, ethambutol, moxifloxacin, rifapentine, clofazimine, bedaquiline (TMC207), nitroimidazo-oxazine PA-824, delamanid (OPC-67683), oxazolidinone such as linezolid, tedizolid, radezolid, sutezolid (PNU-100480), and posizolid (AZD-5847), EMB analogue SQ109, a benzothiazinone, a dinitrobenzamide and an antiviral agent including an antiretroviral agent. In related aspects, the second, third, fourth, fifth and sixth therapeutic agent is a therapeutic agent approved and/or recommended for the treatment of tuberculosis.

A related embodiment provides a pharmaceutical formulation comprising a compound whose structure comprises Formula III or Formula IIIa or a salt thereof, and optionally comprises a second, third, fourth, fifth or sixth therapeutic agent, wherein the optional first, second, third, fourth, fifth or sixth therapeutic agent is an antiretroviral agent selected from of zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, or darunavir.

As described herein, embodiments of the invention include coadministering, whether simultaneously, sequentially or in combination, a first therapeutic agent that is a substituted benzoxaborole or salt thereof as described herein, preferably a substituted benzoxaborole of Formula III or Formula IIIa as described herein, or a pharmaceutically acceptable salt thereof, optionally in combination with a second therapeutic agent, optionally in combination with a third therapeutic agent, optionally in combination with a fourth therapeutic agent, optionally in combination with a fifth and/or a sixth therapeutic agent, to a subject exposed to or infected with a mycobacterium species, including a *Mycobacterium tuberculosis* species. In certain embodiments, the first therapeutic agent is a substituted benzoxaborole of Formula III or Formula IIIa as described herein or a pharmaceutically acceptable salt thereof, and the second and/or third and/or fourth therapeutic agent is an anti-tubercular agent. In certain embodiments, the mycobacterium species is a drug-resistant variant; in certain embodiments the mycobacterium species is a multi-drug resistant variant.

In other particular embodiments there is provided a method for killing mycobacteria comprising contacting the mycobacteria or an animal, including a human, exposed to or infected with a mycobacterium with a first therapeutic agent that is a compound whose structure comprises Formula III or Formula IIIa as described herein, or a pharmaceutically acceptable salt thereof, optionally contacting the cells or subject with a second therapeutic agent, optionally contacting the cells or subject with a third therapeutic agent, optionally contacting the cells or subject with a fourth therapeutic agent, optionally contacting the cells or subject with a fifth and/or a sixth therapeutic agent, such that contacting kills mycobacteria cells. In particular embodiments, the first therapeutic agent is a substituted benzoxaborole that is a compound whose structure comprises Formula III or Formula IIIa as described herein, or a pharmaceutically acceptable salt thereof and the optional second, third, fourth, fifth and/or sixth therapeutic agent is an anti-tubercular agent or a salt thereof. In other particular embodiments, the subject was exposed to or is infected with *Mycobacterium tuberculosis*.

Still other particular embodiments provide a method for inhibiting the replication of mycobacterial cells, the method comprising contacting the mycobacterial cells or an animal, including a human exposed to or infected with a mycobacterial cells with a first therapeutic agent that is a compound as described herein or a salt thereof, optionally contacting the mycobacterial cells or animal with a second therapeutic agent, optionally contacting the mycobacterial cells or animal with a third therapeutic agent, optionally contacting the mycobacterial cells or animal with a fourth therapeutic agent, optionally contacting the mycobacterial cells or animal with a fifth and/or a sixth therapeutic agent, such that contacting inhibits the replication of the mycobacterial cells. In particular embodiments, the first therapeutic agent is a substituted benzoxaborole that is a compound as described herein or a salt thereof and the optional second, third, fourth, fifth and/or sixth therapeutic agent is an anti-tubercular agent or a salt thereof. In other particular embodiments, the subject was exposed to or is infected with *Mycobacterium tuberculosis*.

BRIEF DESCRIPTIONS OF THE DRAWINGS

Figure 2:
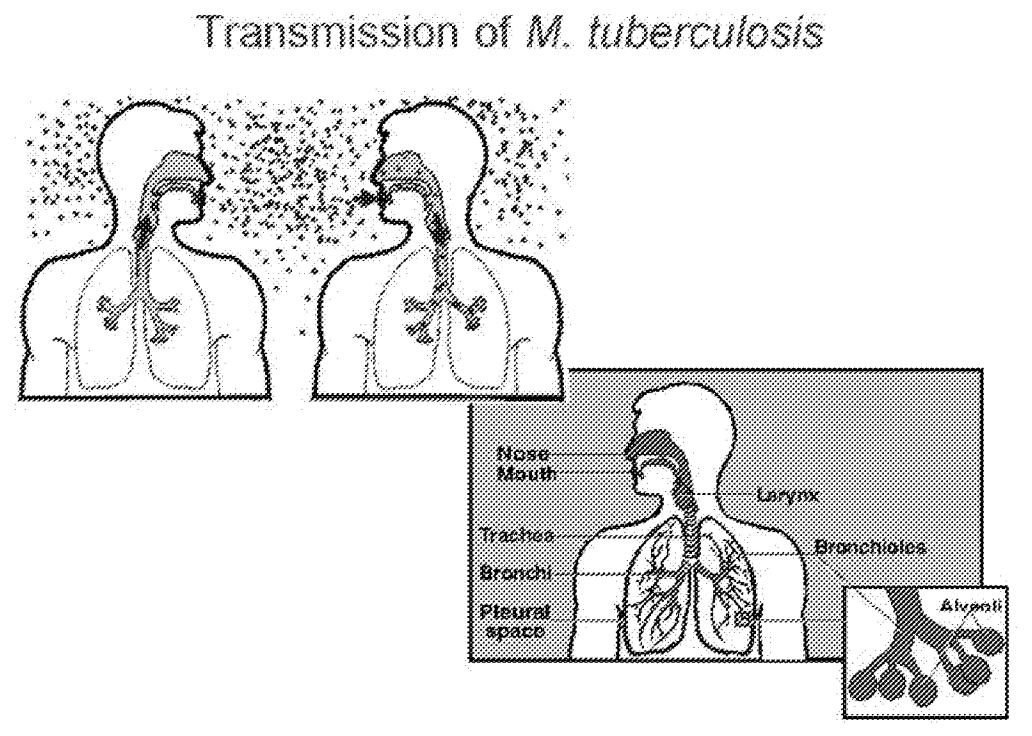

FIG. 2 shows transmission of tuberculosis.

Figure 1:
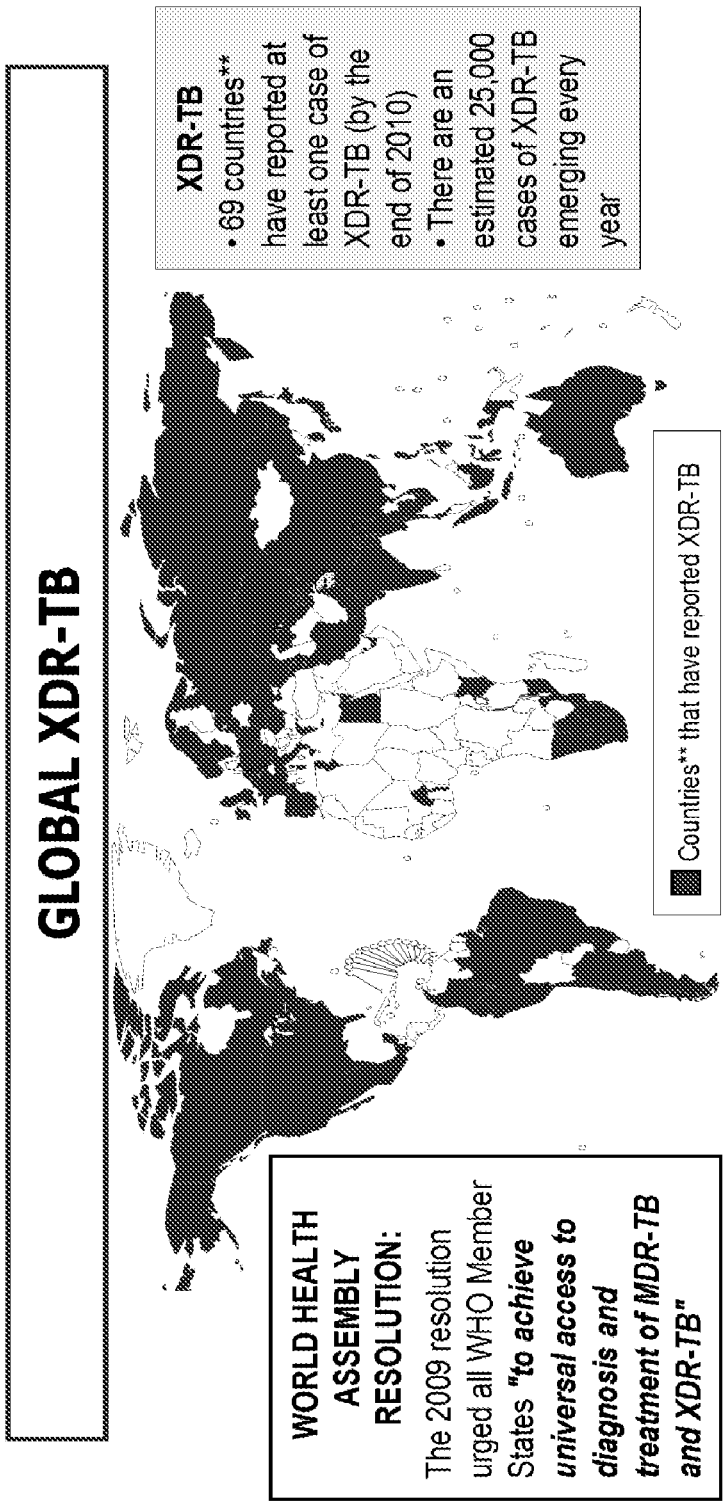
FIG. 1 is a world map indicating where, geographically, XDR-TB has been documented.

Table 1 provides MIC values against non-Mycobacterial strains for substituted benzoxaboroles.

Table 2 provides LeuRS inhibition IC50 values, MIC values against the *M. tuberculosis* standard strain Mtb H37Rv, toxicity values against human HepG2 cells, and selectivity values for comparator substituted benzoxaboroles.

Table 3 provides LeuRS inhibition IC50 values, MIC values against the *M. tuberculosis* standard strain Mtb H27Rv, toxicity values against human HepG2 cells, and selectivity values for certain exemplified compounds of the invention.

DETAILED DESCRIPTION OF SPECIFIC EMBODIMENTS

"Animal" as used herein means any of a kingdom (Animalia) of living things including many-celled organisms, including livestock and pets, including cattle, sheep, goats, dogs and cats, or a human, including an immune-suppressed human.

"Compound of the Invention" as used herein refers to a compound described herein for use in treating a mycobacteriaum infection and/or that has activity against mycobacteria, and particulary has selectivity for killing *Mycobacterium tuberculosis* strains, particularly when compared to acitive against other non-mycobacterium strains.

"Combination of the invention," as used herein refers to the combinations of compounds described and/or exemplified herein, and salts (e.g. pharmaceutically acceptable salts), prodrugs, solvates and hydrates of these compounds.

"Diastereomer" as used herein refers to one of a pair of stereoisomers that is not mirror image of the other stereoisomer.

"Enantiomer" as used herein refers to one of a pair of non-superimposable racemic compounds (racemates) that is a mirror image of the other enantiomer. Enantiomers have the property of rotating the plane of polarized light in one direction or another when in pure form but as a racemic mixture, the mixture does not rotate the plane of polarized light.

"Effective" amount of a compound, combination thereof or formulation thereof, means an amount of a compound that is the active agent which inhibits the growth or proliferation or kills mycobacteria, particularly *Mycobacterium tuberculosis*, including a combination of formulation thereof, such that the amount is sufficient to provide the desired local or systemic effect. A "therapeutically effective" or "pharmaceutically effective" amount refers to the amount of compound, including a combination or formulation thereof, sufficient to achieve a desired therapeutic or pharmaceutical result.

The term "pharmaceutically acceptable salt" is meant to include a salt of a compound described herein which is prepared with relatively nontoxic acids or bases, depending on the particular substituents found on the compounds described herein. When compounds as described herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, I-arginine, d-lysine or I-lysine), or magnesium salt, or a similar salt. When compounds as described herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds as described herein contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds as described herein. Additionally, prodrugs can be converted to the compounds of the invention by chemical or biochemical methods in an ex vivo environment.

Certain of the compounds of Formula III and Formula IIIa may form acid addition salts with one or more equivalents of the acid. The present invention includes within its scope all possible stoichiometric and non-stoichiometric forms.

The term "$^1$H NMR structure" refers to a structure determined from a proton nuclear magnetic resonance ($^1$H NMR) spectrum. A $^1$H NMR spectrum may be generated by performing $^1$H NMR spectroscopy on any molecule having carbon atoms and hydrogens (protons), such as the compounds described in the Examples. $^1$H NMR spectroscopy is performed using a 300-MHz or 400-MHz NMR spectrometer, wherein the compound is dissolved in a fully-deuterated organic solvent, such as DMSO-δ6 or CD$_3$OD. In $^1$H NMR spectroscopy, chemically equivalent protons (those having the exact chemical and electronic environment) give rise to unique signals in a $^1$H NMR spectrum. The position of each proton signal in a $^1$H NMR spectrum—its chemical shift—is shown relative to a reference compound—tetramethylsilane (TMS)—and is measured as a delta from the zero point—the proton signal for TMS. The intensity and characteristic of the proton signal provides information about the environment of each unique and each chemically equivalent proton in a molecule, as well as information on how many protons are represented by a particular signal. The signal for protons attached to C, O, and other atoms of a molecule can be assigned by one of skill in the art using $^1$H NMR spectroscopy, and from that assignment a structure for the molecule or compound can be determined. In the Examples described below, proton nuclear magnetic resonance ($^1$H NMR) spectra were recorded, with chemical shifts reported in parts per million (δ) downfield from the standard tetramethylsilane (TMS).

The signal from the small percentage of non-fully deuterated protons present in the deuterated solvent used for the $^1$H NMR is used as a reference. Abbreviations for NMR data are as follows: s=singlet, d=doublet, t=triplet, q=quartet, m=multiplet, dd=doublet of doublets, dt=doublet of triplets, app=apparent, br=broad.

Thus, for example, the synthesis of Intermediate 1, a), below, indicates a $^1$H NMR spectrum was recorded at 400 MHz, with the compound dissolved in DMSO-d$_6$, such that the spectrum produced a doublet of peaks at 8.47-8.48 assigned as a single Hydrogen (8.47-8.48 (d, J=4.4 Hz, 1H)); a triplet of peaks at 8.77-8.74 assigned as a single Hydrogen (8.77-8.74 (t, J=7.6 Hz, 1H)); a doublet of peaks at 7.43-7.41 assigned as a single Hydrogen (7.43-7.41 (d, J=8.0 Hz, 1H)); a doublet-doublet of peaks at 7.25-7.22, assigned as a single Hydrogen (7.25-7.22 (dd, J=4.8 Hz, 1H)); a doublet-doublet of peaks at 4.49-4.38 assigned a two Hydrogens (4.49-4.38 (dd, J=16.4 Hz, 2H)), a multiplet of peaks at 2.46-2.42 assigned as a single Hydrogen (2.46-2.42 (m, 1H)); a multiplet of peaks at 1.97-1.93 assigned as two Hydrogens (1.97-1.93 (m, 2H)); a multiplet of peaks as 1.84-1.79 assigned as a single Hydrogen (1.84-1.79 (m, 1H)); a multiplet of peaks at 1.71-1.64 assigned as a single Hydrogen (1.71-1.64 (m, 1H)); a multiplet of peaks at 1.33-1.22 assigned as two Hydrogens (1.33-1.22 (m, 2H)); a singlet peak at 0.93 assigned as three Hydrogens (0.93 (s, 3H)); a singlet peak at 0.92 assigned as three Hydrogens (0.92 (s, 3H)); and a singlet peak at 0.73 assigned as three Hydrogens (0.73 (s, 3H)).

Certain of the substituted benzoxaboroles of Formula III and Formula IIIa described herein may exist in an equilibrium between a closed structure as shown in Formula II and Formula IIa, and an open form, as shown in Formula III and Formula IIIa, in certain solvent environments, such as in the presence of H$_2$O or when in an aqueous solvent. In addition, the $^1$H NMR spectra of certain of the substituted benzoxaboroles described herein, show that such compounds, when dissolved in organic solvents, for example DMSO-δ6 and CD$_3$OD, exist in the closed form, as indicated by the $^1$H NMR data shown in the synthesis Examples below.

In contrast, solid state NMR spectra indicate that certain of the substituted benzoxaboroles described herein exist in the solid state in the open forms of Formula III and Formula IIIa. Throughout the application, substituted benzoxaboroles described herein may be shown either in the $^1$H NMR solution structures of the closed ring forms of Formula II and Formula IIa, or in the solid state structures of the open ring forms of Formula III and Formula IIIa. It is also understood that in certain conditions, such as when dissolved in organic solvents, the substituted benzoxaboroles may exist in the closed forms of Formula II and Formula IIa; whereas in other conditions, e.g. such as when water is present, the substituted benzoxaboroles described herein may exist in an equilibrium between the open forms of Formula III and Formula IIIa and the closed forms of Formulas II and Formula IIa. It has also been shown that in the solid state, certain of the substituted benzoxaboroles described herein may exist in the open forms of Formula III and Formula IIIa.

The compounds of Formula III and Formula IIIa may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water). Compounds of Formula III and compounds of Formula IIIa as described herein may exist as a hydrate according to the structure of Formula IV or of Formula Iva below:

Formula IV

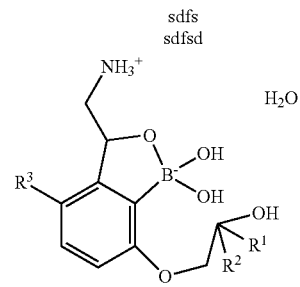

Formula Iva

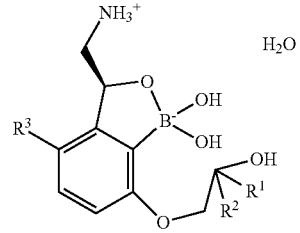

wherein R$^1$, R$^2$ and R$^3$ and are as described herein.

The subject invention also includes isotopically-labeled compounds which are identical to those recited in Formula III and Formula IIIa but for the fact that one or more atoms are replaced by an atom having an atomic mass or mass number different from the atomic mass or mass number most commonly found in nature. Examples of isotopes that can be incorporated into compounds as described herein include isotopes of hydrogen, carbon, nitrogen, oxygen, fluorine, iodine and chlorine such as $^3$H, $^{11}$C, $^{14}$C, $^{18}$F, $^{123}$I or $^{125}$I.

Compounds of the present invention and pharmaceutically acceptable salts of said compounds that contain the aforementioned isotopes and/or other isotopes of other atoms are within the scope of the present invention. Isotopically labeled compounds of the present invention, for example those into which radioactive isotopes such as $^3$H or $^{14}$C have been incorporated, are useful in drug and/or substrate tissue distribution assays. Tritiated, ie. $^3$H, and carbon-14, ie. $^{14}$C, isotopes are particularly preferred for their ease of preparation and detectability. $^{11}$C and $^{18}$F isotopes are particularly useful in PET (positron emission tomography).

Because the compounds of Formula III and Formula IIIb as described herein are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

One embodiment provides a substituted benzoxaborole or a salt thereof having a structure comprising Formula III:

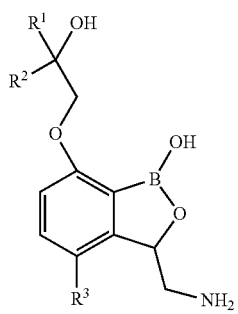

Formula III wherein $R^3$ is selected from —CH$_3$; $R^1$ and $R^2$ are each independently H, —CH$_3$, —CH$_2$CH$_3$, —CH$_2$CH$_2$CH$_3$, and —CH(CH$_3$)$_2$;

One embodiment provides a substituted benzoxaborole whose structure comprises Formula III wherein $R^3$ is —CH$_2$CH$_3$ and $R^1$ and $R^2$ are each independently selected from H, —CH$_3$, —CH$_2$CH$_3$, —CH$_2$CH$_2$CH$_3$, and —CH(CH$_3$)$_2$.

One embodiment provides a substituted benzoxaborole whose structure comprises Formula III or a pharmaceutically acceptable salt thereof, wherein $R^3$ is —CH$_3$; $R^1$ and $R^2$ are each independently selected from H, —CH$_3$, and —CH$_2$CH$_3$.

One embodiment provides a substituted benzoxaborole whose structure comprises Formula III or a salt thereof, wherein $R^3$ is —CH$_3$; $R^1$ and $R^2$ are each independently selected H or —CH$_3$.

One embodiment provides a substituted benzoxaborole whose structure comprises Formula III or a pharmaceutically acceptable salt thereof, wherein $R^3$ is —CH$_3$; $R^1$ and $R^2$ are independently H or —CH$_3$.

One embodiment provides a substituted benzoxaborole whose structure comprises Formula III as shown below:

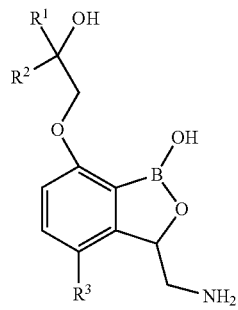

or a pharmaceutically acceptable salt thereof, wherein $R^3$ is —CH$_3$; $R^1$ and $R^2$ are each independently H or —CH$_3$.

In one embodiment, there is provided a compound whose structure comprises Formula III:

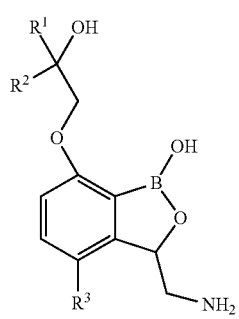

Formula III wherein $R^3$ is selected from —CH$_3$, —CH$_2$CH$_3$, —CH$_2$CH$_2$CH$_3$, —CH(CH$_3$)$_2$, phenyl, and thiophenyl; $R^1$ and $R^2$ are each independently selected from H, —CH$_3$, —CH$_2$CH$_3$, —CH$_2$CH$_2$CH$_3$, and —CH(CH$_3$)$_2$.

Another embodiment provides a substituted benzoxaborole whose structure comprises Formula IIIa

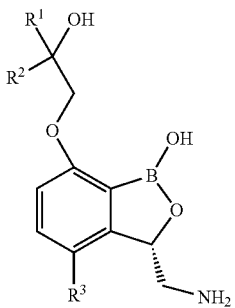

Formula IIIa wherein $R^3$ is —CH$_3$ and $R^1$ and $R^2$ are each independently H or —CH$_3$, or a pharmaceutically acceptable salt thereof.

In one aspect the invention provides a pharmaceutical composition comprising a substituted benzoxaborole whose structure comprises Formula III or Formula IIIa, or a pharmaceutically acceptable salt or solvate thereof, and one or more pharmaceutically acceptable carriers, excipients or diluents.

Another aspect of the invention further provides a method of treatment of a mycobacterial infection in a mammal, particularly in a human, which method comprises administering to a mammal in need of such treatment an effective amount of a first therapeutic agent that is a compound whose structure comprises Formula III or a compound whose structure comprises Formula IIIa, or a pharmaceutically acceptable salt or solvate thereof. Related embodiments further comprise administering to a mammal in need of such treatment an effective amount of a first therapeutic agent that is a compound whose structure comprises Formula III or a compound whose structure comprises Formula IIIa, or a pharmaceutically acceptable salt thereof, optionally administering in combination with an effective amount of a second therapeutic agent, optionally administering in combination with an effective amount of a third therapeutic agent, optionally administering in combination with an effective amount of a fourth therapeutic agent, optionally administering in combination with an effective amount of a fifth therapeutic agent, optionally administering in combination with an effective amount of a sixth therapeutic agent.

In related aspects of the embodiment the optional second, third, fourth, fifth and sixth therapeutic agent is an anti-mycobacterial agent. In related aspects, administering the first therapeutic agent and optionally administering the second, third, fourth, fifth and sixth therapeutic agent occurs concurrently, or administering the first therapeutic agent and optionally administering the second, third, fourth, fifth and sixth therapeutic agent occurs sequentially. In other related aspects of the invention, any one of the second, third, fourth, fifth or sixth therapeutic agent is selected from an antimicrobial agent, an antiviral agent, an anti-infective agent, an analgesic, a vitamin, a nutritional supplement, an anti-inflammatory agent, an analgesic, and an steroid.

The invention yet further provides a compound whose structure comprises Formula III, or a pharmaceutically acceptable salt or solvate thereof, for use in the treatment of a mycobacterial infection in a mammal, particularly in a human. In related aspects, the mammal is a human wherein the mycobacterial infection is a *Mycobacterium tuberculosis* infection. In other aspects, the human with a *Mycobacterium tuberculosis* infection is also infected with a retrovirus, including a human immunodeficiency virus.

The invention still further provides the use of a compound whose structure comprises Formula III or Formula IIIa, or a pharmaceutically acceptable salt or solvate thereof, in the manufacture of a medicament for use in the treatment of a mycobacterial infection in a mammal, particularly in a human.

The invention also provides a pharmaceutical composition comprising a compound whose structure comprises Formula III or Formula IIIa, or a pharmaceutically acceptable salt, or solvate thereof, and one or more pharmaceutically acceptable carriers, excipients or diluents, for use in the treatment of a mycobacterial infection in a mammal, particularly in a human.

The invention also provides a pharmaceutical composition comprising a compound whose structure comprises Formula III or Formula IIIa, or a pharmaceutically acceptable salt, or solvate thereof, and one or more pharmaceutically acceptable carriers, excipients or diluents, for use in the treatment of mycobacterial infections in a mammal, particularly in a human.

In another particular embodiment the substituted benzoxaborole in the combination has a solid state NMR structure comprising a structure indicated below:

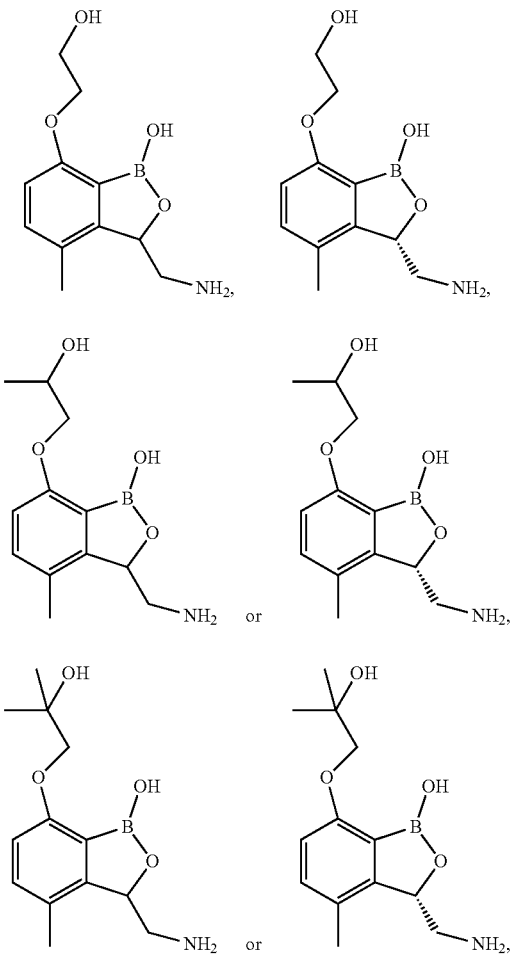

or a pharmaceutically acceptable salt thereof.

In one particular embodiment, the compound has a structure as indicated below:

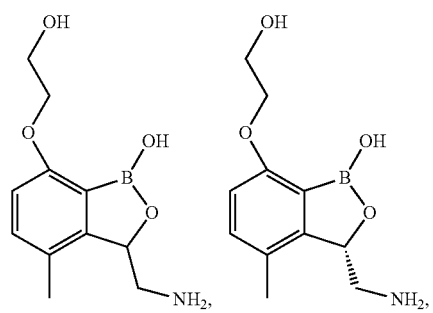 [SMILES: Cc1ccc(OCCO)c2c1C(CN)OB2O ; Cc1ccc(OCCO)c2c1[C@@H](CN)OB2O]

or a pharmaceutically acceptable salt thereof.

In one particular embodiment, the compound comprises a structure as indicated below:

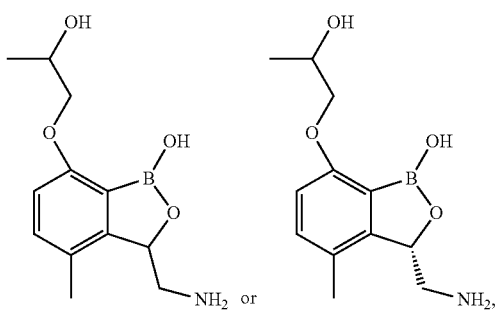 [SMILES: Cc1ccc(OCC(C)O)c2c1C(CN)OB2O ; "or" ; Cc1ccc(OCC(C)O)c2c1[C@@H](CN)OB2O]

or a pharmaceutically acceptable salt thereof.

In one particular embodiment, the compound comprises a structure as indicated below:

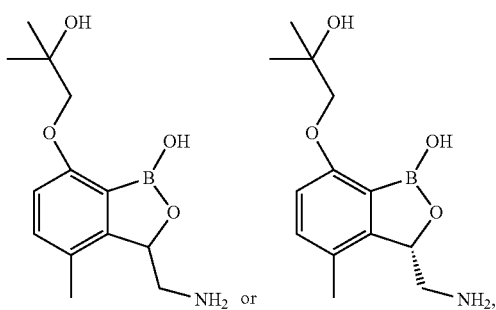 [SMILES: Cc1ccc(OCC(C)(C)O)c2c1C(CN)OB2O ; "or" ; Cc1ccc(OCC(C)(C)O)c2c1[C@@H](CN)OB2O]

or a pharmaceutically acceptable salt thereof.

An embodiment of the invention provides a substituted benzoxaborole whose closed form is:
3-methyl-7,8-dihydro-2H-1,6,9-trioxa-9a-borabenzo[cd]azulen-2-yl)methanamine;
(S)-(3-methyl-7,8-dihydro-2H-1,6,9-trioxa-9a-borabenzo[cd]azulen-2-yl)methanamine;
3,8-dimethyl-7,8-dihydro-2H-1,6,9-trioxa-9a-borabenzo[cd]azulen-2-yl)methanamine;
((2S)-3,8-dimethyl-7,8-dihydro-2H-1,6,9-trioxa-9a-borabenzo[cd]azulen-2-yl)methanamine;
(3,8,8-trimethyl-7,8-dihydro-2H-1,6,9-trioxa-9a-borabenzo[cd]azulen-2-yl)methanamine;
(S)-(3,8,8-trimethyl-7,8-dihydro-2H-1,6,9-trioxa-9a-borabenzo[cd]azulen-2-yl)methanamine;
or a pharmaceutically acceptable salt thereof.

An embodiment of the invention provides a substituted benzoxaborole whose open form is:
3-(aminomethyl)-7-(2-hydroxyethoxy)-4-methylbenzo[c][1,2]oxaborol-1(3H)-ol;
(S)-3-(aminomethyl)-7-(2-hydroxyethoxy)-4-methylbenzo[c][1,2]oxaborol-1(3H)-ol
3-(aminomethyl)-7-(2-hydroxypropoxy)-4-methylbenzo[c][1,2]oxaborol-1(3H)-ol;
(3S)-3-(aminomethyl)-7-(2-hydroxypropoxy)-4-methyl-benzo[c][1,2]oxaborol-1(3H)-ol;
3-(aminomethyl)-7-(2-hydroxy-2-methylpropoxy)-4-methylbenzo[c][1,2]oxaborol-1(3H)-ol;
(S)-3-(aminomethyl)-7-(2-hydroxy-2-methylpropoxy)-4-methylbenzo[c][1,2]oxaborol-1(3H)-ol.

Figure 4:
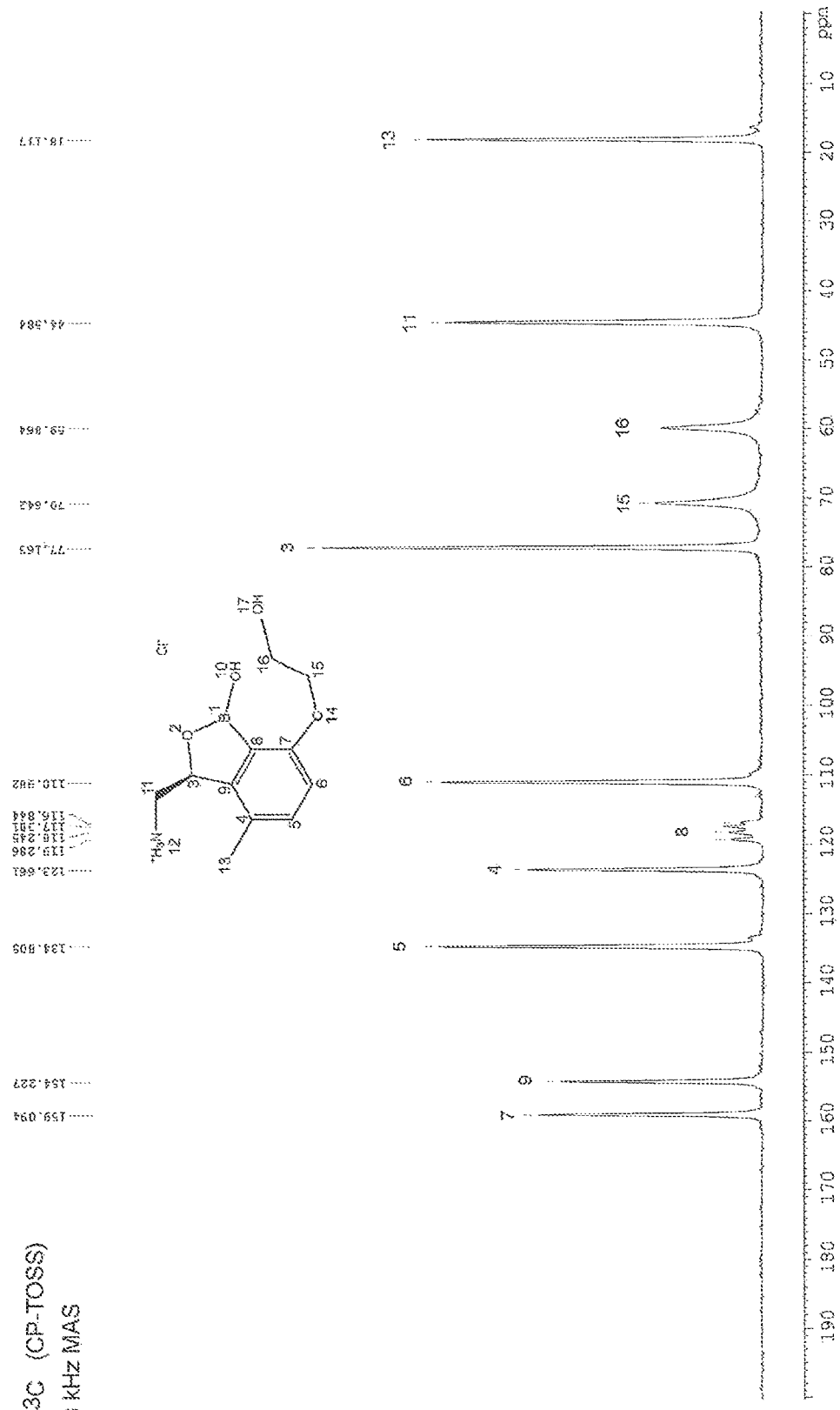
FIG. 4 shows the ssNMR $^{13}$C CP-TOSS spectrum for the open form of the G26-CH$_3$ in the solid state.

One embodiment provides a compound having a solid state NMR pattern substantially as shown in FIG. 4, or a pharmaceutically acceptable salt there.

Another embodiment provides a pharmaceutical composition comprising a compound as described herein and at least one excipient.

Another embodiment provides a compound as described herein for use in a medicine for the treatment of *Mycobacterium tuberculosis*.

In another particular embodiment, the treatment of a mycobacterial infection or condition occurs through inhibition of an editing domain of an aminoacyl tRNA synthetase by means of binding to the editing active site. In another exemplary embodiment, the treatment of a mycobacterial infection or condition occurs through blocking of an editing domain of an aminoacyl tRNA synthetase.

In a particular embodiment, the mycobacterial infection and/or disease is treated through oral administration of the combination of the invention. In an exemplary embodiment, the mycobacterial infection and/or disease is treated through intravenous administration of the combination of the invention.

Pharmaceutical Formulations

In another aspect, the invention is a pharmaceutical formulation which includes: (a) a compound as disclosed herein and b) a pharmaceutically acceptable excipient; or (a) a combination of the invention. In another aspect, the pharmaceutical formulation includes: (a) a compound as disclosed herein and a pharmaceutically acceptable excipient; or (b) a combination described herein. In another aspect, the pharmaceutical formulation includes: (a) a pharmaceutically acceptable excipient; and (b) a combination described herein, or a salt, prodrug, hydrate or solvate thereof. In another aspect, the pharmaceutical formulation includes: (a) a pharmaceutically acceptable excipient; and (b) a combination described herein, or a salt, hydrate or solvate thereof. In another aspect, the pharmaceutical formulation includes: (a) a pharmaceutically acceptable excipient; and (b) a combination described herein, or a salt, hydrate or solvate thereof. In another aspect, the pharmaceutical formulation includes: (a) a pharmaceutically acceptable excipient; and (b) a salt of a combination described herein. In an exemplary embodiment, the salt is a pharmaceutically acceptable salt. In another aspect, the pharmaceutical formulation includes: (a) a pharmaceutically acceptable excipient; and (b) a prodrug of a combination described herein. In another aspect, the pharmaceutical formulation includes: (a) a pharmaceutically acceptable excipient; and (b) a combination described herein. In an exemplary embodiment, the pharmaceutical formulation is a unit dosage form. In an exemplary embodiment, the pharmaceutical formulation is a single unit dosage form.

In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a three unit dosage form. In an exemplary embodiment, the pharmaceutical formulation is a four unit dosage form. In an exemplary embodiment, the pharmaceutical formulation is a five unit dosage form. In an exemplary embodiment, the pharmaceutical formulation is a six unit dosage form. In an exemplary embodiment, the pharmaceutical formulation is a one, two, three, four, five, six or seven unit dosage form comprising a first unit dosage form and a second, third, fourth, fifth and/or sixth unit dosage form, wherein the first unit dosage form includes a) a therapeutically effective amount of a compound as described herein and b) a first pharmaceutically acceptable excipient; and the second, third, fourth, fifth, and/or sixth unit dosage form includes c) a therapeutically acceptable amount of an additional therapeutic agent that is an anti-mycobacterial agent and d) a second pharmaceutically acceptable excipient.

Information regarding excipients of use in the formulations of the invention can be found in Remington: The Science and Practice of Pharmacy, 21st Ed., Pharmaceutical Press (2011) which is incorporated herein by reference.

Combinations

In an exemplary embodiment, the invention provides a) a first therapeutic agent that is a substituted benzoxaborole or salt thereof as described herein; b) a second therapeutic activity. In certain embodiments, the second therapeutic agent is an antibacterial agent, more specifically an anti-tubercular agent, more specifically an anti-*M. tuberculosis* agent.

In an exemplary embodiment, the combination is part of a pharmaceutical formulation described herein. Such conditions are known to one skilled in the art and specific conditions are set forth in the Examples appended hereto.

Dosage Forms of the Combination

The individual components of the combinations of the invention, for example, a combination described herein, may be administered either simultaneously or sequentially in a unit dosage form. The unit dosage form may be a single or multiple unit dosage form. In an exemplary embodiment, the invention provides a combination in a single unit dosage form. An example of a single unit dosage form is a capsule wherein both the substituted benzoxaborole and additional therapeutic agent are contained within the same capsule. In an exemplary embodiment, the invention provides a combination in a two unit dosage form. An example of a two unit dosage form is a first capsule which contains the substituted benzoxaborole and a second capsule which contains the additional therapeutic agent. Thus the term 'single unit' or 'two unit' or 'multiple unit' refers to the object which the patient ingests, not to the interior components of the object. Appropriate doses of substituted benzoxaborole will be readily appreciated by those skilled in the art. Appropriate doses of an additional therapeutic agent that is not a compound whose structure comprises Formula III or Formula IIIa will be readily appreciated by those skilled in the art. In one particular embodiment, the substituted benzoxaborole is present in the combination in a therapeutically effective amount. In one particular embodiment, the additional therapeutic agent that is not a compound whose structure comprises Formula III or Formula IIIa is present in the combination in an amount sufficient to kill or reduce the presence, amount or growth rate of mycobacteria exposed to the substituted benzoxaborole, including *M. tuberculosis*.

Additional Therapeutic Agent(s) in the Combination

The combinations of the invention, for example, a combination described herein, may also include an additional therapeutic agent or therapeutic agents. The invention thus provides, in a further aspect, a combination comprising a substituted benzoxaborole described herein or a pharmaceutically acceptable salt thereof, and at least one additional therapeutic agent. The invention thus provides, in a further aspect, a combination comprising a substituted benzoxaborole described herein or a pharmaceutically acceptable salt thereof, and at least one additional therapeutic agent. In an exemplary embodiment, the additional therapeutic agent is an antimycobacterial agent. In one aspect, the invention comprises: a) a combination of the invention; and b) at least one additional therapeutic agent. In another exemplary embodiment, the invention comprises: a) a combination of the invention; b) a first additional therapeutic agent; and c) a second additional therapeutic agent. In another exemplary embodiment, the invention comprises: a) a combination of the invention; b) a first additional therapeutic agent; c) a second additional therapeutic agent; and d) a third additional therapeutic agent. The first additional therapeutic agent or second additional therapeutic agent or third additional therapeutic agent may be selected from the additional therapeutic agents described herein.

The combinations may conveniently be presented for use in the form of a pharmaceutical formulation. In a further aspect of the present invention there is provided a pharmaceutical combination comprising a compound whose structure comprises Formula III, or a pharmaceutically acceptable salt or solvate thereof, together with one or more additional therapeutic agents, and one or more pharmaceutically acceptable carriers, excipients or diluents. The individual components of such combinations may be administered either sequentially or simultaneously in separate or combined pharmaceutical Formulations by any convenient route.

When an additional therapeutic agent is used with a combination as described herein against the same disease state, the dose of each compound may differ from that when the compound is used alone. Appropriate doses will be readily appreciated by those skilled in the art. It will be appreciated that the amount of a compound as described herein required for use in treatment will vary with the nature of the condition being treated and the age and the condition of the patient and will be ultimately at the discretion of the attendant physician or veterinarian.

Preparation of Boron-Containing Compounds

Compounds of use in the invention can be prepared using commercially available starting materials, known intermediates, or by using the synthetic methods described herein, or published in references described and incorporated by reference herein, such as U.S. Pat. Nos. 7,816,344, 8,461,364, 8,703,742, 9,243,003 and continuation and divisional applications thereof; US publication numbers US20100292504, US20140315860 and applications claiming priority therefrom; and PCT published application numbers WO2008/157726, WO2010080558, WO2011127143, WO2012/033858 and WO2015/021396 and applications claiming priority therefrom. The general procedures used to synthesize the compounds of Formula III and Formula IIIa, are described in the reaction Schemes below and are illustrated in the Examples.

Certain substituted benzoxaboroles as described herein may be prepared as outlined in Scheme 1.

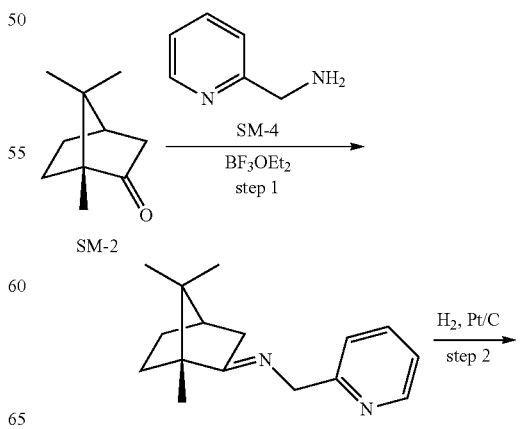

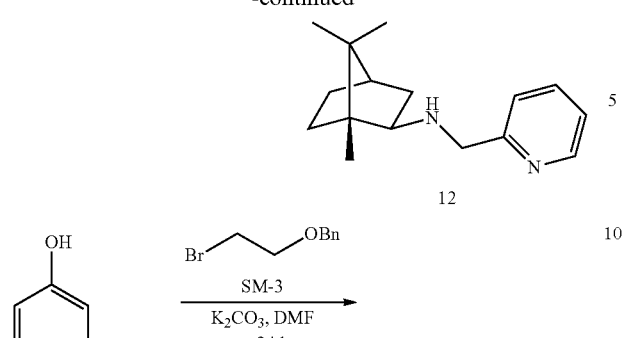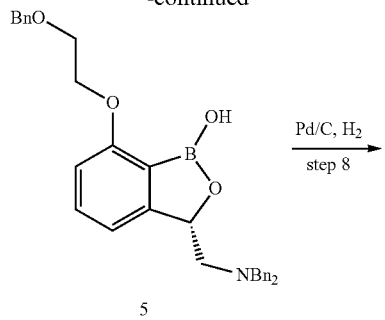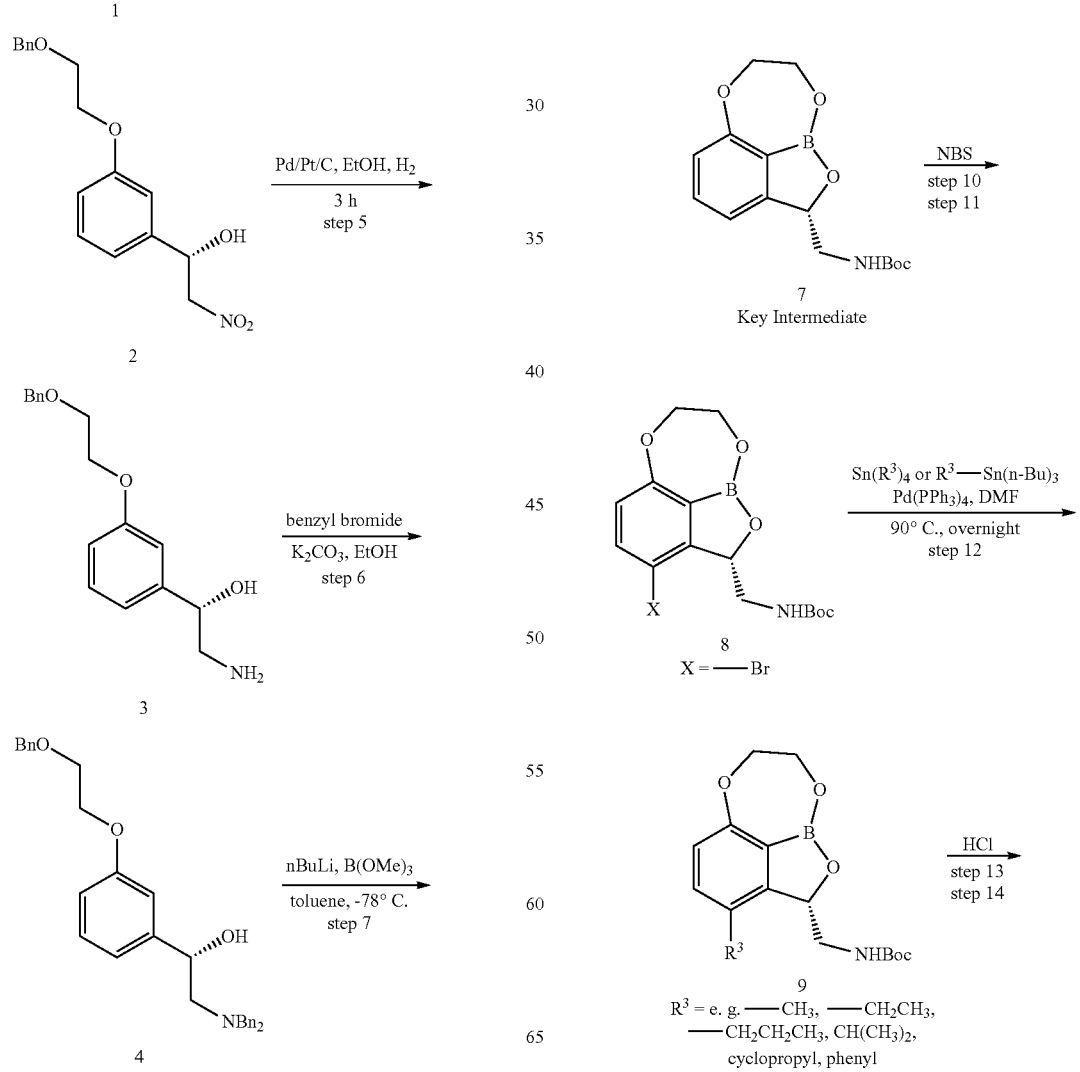

-continued

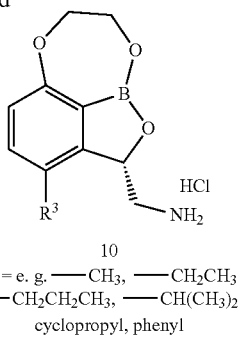

10
$R^3$ = e. g. —CH$_3$, —CH$_2$CH$_3$,
—CH$_2$CH$_2$CH$_3$, —CH(CH$_3$)$_2$,
cyclopropyl, phenyl Although not expressly shown, compounds 6, 7, 8, 9 and 10 of Scheme 1 may exist in equilibrium with the corresponding open structure depending on the environment. In addition, certain substituted benxozaborole compounds disclosed herein may exist in such an equilibrium in certain solvents. Such an equilibirium is shown by example below:

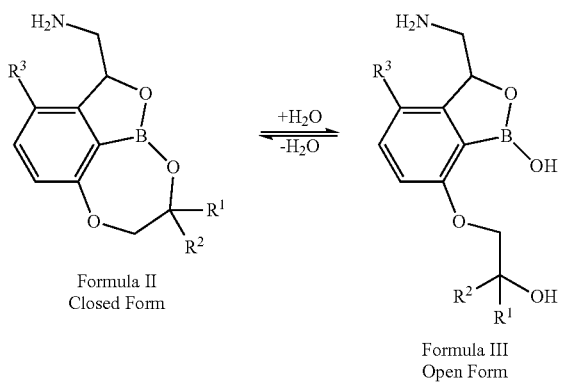

Formula II
Closed Form

Formula III
Open Form

In an embodiment, certain substituted benzoxaboroles disclosed herein have been found to exist in the open form in the solid state. A combination of single $^{13}$C and solid state NMR analysis confirms that certain substituted benzoxaboroles disclosed herein exist in the open form in the solid state. Solution state NMR studies also show that when dissolved in solution, certain substituted benzoxaborole compounds disclosed herein exist in equilibrium between the open and closed form, and that the balance of the equilibrium is affected by the solvent used and the presence of H$_2$O.

It is understood that the substituted benzoxaboroles disclosed herein, whether shown in the closed form or the open form, may exist in the closed form in organic solvents such as DMSO and CH$_3$OH, may exist in an equilibrium between the closed form and open form in an environment comprising H$_2$O, and may exist in the open form in the solid state.

Composition and Formulations

The compounds as described herein may be formulated for administration in any convenient way for use in human or veterinary medicine, by analogy with formulation of anti-mycobacterial agents, or formulation of other anti-tubercular agents.

The compounds described herein will normally, but not necessarily, be formulated into pharmaceutical compositions prior to administration to a patient. In one aspect, the invention is directed to a pharmaceutical composition comprising a compound whose structure comprises Formula III or Formula IIIa, or a pharmaceutically acceptable salt. In another aspect the invention is directed to a pharmaceutical composition comprising a compound whose structure comprises Formula III, a compound whose structure comprises Formula IIIa, or a pharmaceutically acceptable salt, and one or more pharmaceutically acceptable carriers, excipients or diluents. The carrier, excipient or diluent must be "acceptable" in the sense of being compatible with the other ingredients of the Formulation and not deleterious to the recipient thereof.

The pharmaceutical compositions described herein include those in a form adapted for oral, or parenteral use and may be used for the treatment of a mycobacterial infection in a mammal including a human.

The pharmaceutical compositions described herein include those in a form adapted for oral, topical or parenteral use and may be used for the treatment of mycobacterial infections in a mammal including a human.

The composition may be formulated for administration by any convenient route. For the treatment of tuberculosis, the compositions may be in the form of tablets, capsules, powders, granules, lozenges, aerosols or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

In one aspect of the invention, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 20-1000 mg of the active ingredient. The dosage as employed for adult human treatment will typically range from 50 to 300 mg per day, for instance 150 to 200 mg per day depending on the route and frequency of administration. Such a dosage corresponds to 0.5 to 5 mg/kg per day. Preferably the dosage is from 0.5 to 2 mg/kg per day and more preferably the dose is less than 1 mg/kg per day.

The compound whose structure comprises Formula III, Formula IIIa, or a pharmaceutically acceptable pharmaceutically acceptable salt or solvate thereof, may be the sole therapeutic agent in the compositions described herein, or it may be present in the Formulation in combination with one or more additional therapeutic agents. The invention thus provides, in a further aspect, a combination comprising a compound whose structure comprises Formula III or Formula IIIa, or a pharmaceutically acceptable salt, solvate thereof together with one or more additional therapeutic agents.

The one or more additional therapeutic agent is, for example, an agent useful for the treatment of tuberculosis in a mammal. Examples of such therapeutic agents include, rifampin, pyrazinamide, ethambutol, moxifloxacin, rifapentine, clofazimine, bedaquiline (TMC207), nitroimidazo-oxazine PA-824, delamanid (OPC-67683), oxazolidinone such as linezolid, tedizolid, radezolid, sutezolid (PNU-100480), and posizolid (AZD-5847), EMB analogue SQ109, a benzothiazinone, a dinitrobenzamide and an antiviral agent including an antiretroviral agent, or any TB agent being developed for the treatment of TB with a positive response in Phase IIa EBA trials, or any TB agent under development by the Global Alliance for Tuberculosis.

When a compound whose structure comprises Formula III or Formula IIIa, or a pharmaceutically acceptable salt or solvate thereof is used in combination with one or more additional therapeutic agents, the dose of the compound or agent may differ from that when the compound or agent is used alone. Appropriate doses will be readily appreciated by those skilled in the art. It will be appreciated that the amount of a compound described herein and the one or more additional therapeutic agents required for use in treatment will vary with the nature of the condition being treated and the age and the condition of the patient and will be ultimately at the discretion of the attendant physician or veterinarian.

The combinations may conveniently be presented for use in the form of a pharmaceutical Formulation. In a further aspect of the present invention there is provided a pharmaceutical combination comprising a compound whose structure comprises Formula III of Formula IIIa, or a pharmaceutically acceptable salt or solvate thereof, together with one or more additional therapeutic agents, and one or more pharmaceutically acceptable carriers, excipients or diluents. The individual components of such combinations may be administered either sequentially or simultaneously in separate or combined pharmaceutical Formulations by any convenient route.

When administration is sequential, either the compound of the present invention or one or more additional therapeutic agent may be administered first. When administration is simultaneous, the combination may be administered either in the same or different pharmaceutical composition. When combined in the same Formulation it will be appreciated that the compound and agents must be stable and compatible with each other and the other components of the Formulation. When formulated separately they may be provided in any convenient formulation, conveniently in such manner as are known for such compounds in the art.

Methods of Inhibiting Bacterial Growth or Killing Bacteria

The compounds exemplified and described herein and combinations thereof are expected to exhibit potency against mycobacteria and therefore have the potential to kill mycobacteria and/or inhibit the replication of mycobacteria. The combinations as described herein are expected to exhibit potency against mycobacteria possessing resistance to standard-of-care anti-mycobacterial agents, and thus have the potential to kill mycobacteria and/or inhibit the replication of such "resistant" mycobacteria. In aspects of the invention, compounds as described herein possess a remarkable activity against a selection of drug sensitive mycobacterial isolates, including, MDR-TB (multidrug resistant TB) and XDR-TB (extensively-drug resistant TB) clinical isolates, exhibiting MIC values of <0.32 µM and the majority have MIC values at between 0.04-0.08 µM in 96 isolates investigated.

A compound as described herein may be used for inhibiting or killing mycobacteria. In a further aspect, the invention provides a method of killing mycobacteria and/or inhibiting replication of mycobactera or a method of treating a mycobacterial infection in an animal such as livestock and pets, including cattle, sheep, goats, dogs and cats, or a human, including an immune-suppressed human said method comprising: contacting the mycobactera with an effective amount of a compound as described herein, thereby killing the mycobacteria and/or inhibiting replication of the mycobacteria, or said method comprising administering to the animal with the mycobacterial infection a therapeutically effective amount of a pharmaceutical composition of the invention, wherein the pharmaceutical composition comprises a compound whose structure comprises Formula III or a compound whose structure comprises Formula IIIa, or a pharmaceutically acceptable salt thereof. In an exemplary embodiment, the combination is part of a pharmaceutical formulation described herein. In another exemplary embodiment, the contacting occurs under conditions which permit entry of the combination into the mycobacterium.

In a further aspect, the invention provides a method of killing mycobacteria and/or inhibiting replication of mycobactera or a method of treating a mycobacterial infection in an animal such as livestock and pets, including cattle, sheep, goats, dogs and cats, or a human, including an immune-suppressed human said method comprising: contacting the mycobactera with an effective amount of a compound or combination as described herein, thereby killing the mycobacteria and/or inhibiting replication of the mycobacteria, or said method comprising administering to the animal with the mycobacterial infection a therapeutically effective amount of a pharmaceutical composition of compound or a combination as described herein, wherein the pharmaceutical composition comprises a compound whose structure comprises Formula III or a compound whose structure comprises Formula IIIa, or a pharmaceutically acceptable salt thereof. In an exemplary embodiment, the combination is part of a pharmaceutical formulation described herein. In another exemplary embodiment, the contacting occurs under conditions which permit entry of the combination into the mycobacterium.

In an exemplary embodiment, the mycobacteria is killed or its replication is inhibited, or the mycobacterial infection is treated, through oral administration of a combination as described herein. In an exemplary embodiment, the mycobacteriais killed or its replication is inhibited, or the mycobacterial infection is treated, through intravenous administration of a combination as described herein. In an exemplary embodiment, the mycobacterium is killed or its replication is inhibited, or the mycobacterial infection is treated, through subcutaneous administration of a combination as described herein, wherein the combination comprises a compound whose structure comprises Formula III or a compound whose structure comprises Formula IIIa, or a pharmaceutically acceptable salt thereof.

In exemplary embodiments, the mycobacteria is contacted or the mycobacterial infection is treated with a combination as described herein comprising a first therapeutic agent that is a compound whose structure comprises Formula III or a compound whose structure comprises Formula IIIa, or salt thereof, and optionally comprising a second, third, fourth, fifth and sixth therapeutic agent in a population of mycobacteria comprising a resistant mycobacterium with a mutation conferring resistance to any one or more of the optional second, third, fourth, fifth and sixth therapeutic agent. In related embodiments, the optional second, third, fourth, fifth and sixth therapeutic agent, or a salt thereof, is an anti-mycobacterial agent, particularly a known anti-mycobacterial agent, more preferably a standard-of-care anti-mycobacterial agent.

In another exemplary embodiment, there is provided a method of killing and/or inhibiting replication of mycobacteria that causes or is associated with a disease in an animal, or a method of treating a mycobacterial infection in an animal, the method comprising contacting the mycobacteria with an effective amount of a compound whose structure comprises Formula III or Formula IIIa or a salt thereof, so as to kill and/or prevent replication of the mycobacterium, or administering to the animal a therapeutically effective amount of a compound whose structure comprises Formula III or Formula IIIa or a salt thereof, wherein the mycobacteria is selected from *Mycobacterium tuberculosis*, *Mycobacterium avium* including subspecies (subsp.) *Mycobacterium avium* subsp. *avium*, *Mycobacterium avium* subsp. *hominissuis*, *Mycobacterium avium* subsp. *silvaticum*, and *Mycobacterium avium* subsp. *paratuberculosis*; *Mycobacterium balnei*, *Mycobacterium sherrisii*, *Mycobacterium africanum*, *Mycobacterium microti*, *Mycobacterium silvaticum*, *Mycobacterium colombiense*, *Mycobacterium indicus pranii*, *Mycobacterium gastri*, *Mycobacterium gordonae*, *Mycobacterium hiberniae*, *Mycobacterium nonchromogenicum*, *Mycobacterium terrae*, *Mycobacterium trivial*, *Mycobacterium kansasii*; *Mycobacterium malmoense*; *Mycobacterium simiae*; *Mycobacterium triplex*, *Mycobacterium genavense*, *Mycobacterium florentinum*, *Mycobacterium lentiflavum*, *Mycobacterium palustre*, *Mycobacterium kubicae*, *Mycobacterium parascrofulaceum*, *Mycobacterium heidelbergense*, *Mycobacterium interjectum*, *Mycobacterium szulgai*; *Mycobacterium branderi*, *Mycobacterium cookie*, *Mycobacterium celatum*, *Mycobacterium bohemicum*, *Mycobacterium haemophilum*, *Mycobacterium lepraemurium*, *Mycobacterium lepromatosis*, *Mycobacterium botniense*, *Mycobacterium chimaera*, *Mycobacterium conspicuum*, *Mycobacterium doricum*, *Mycobacterium forcinogenes*, *Mycobacterium heckeshornense*, *Mycobacterium lacus*, *Mycobacterium monacense*, *Mycobacterium montefiorense*, *Mycobacterium murale*, *Mycobacterium nebraskense*, *Mycobacterium saskatchewanense*, *Mycobacterium scrofulaceum*, *Mycobacterium shimoidel*, *Mycobacterium tusciae*, *Mycobacterium xenopi*, *Mycobacterium intermedium*, *Mycobacterium bolletii*, *Mycobacterium fortuitum*, *Mycobacterium foruitum* subsp. *acetamidolyticum*, *Mycobacterium boenickei*, *Mycobacterium perigrinum*, *Mycobacterium porcinum*, *Mycobacterium senegalense*, *Mycobacterium septicum*, *Mycobacterium neworleansense*, *Mycobacterium houstonense*, *Mycobacterium mucogenicum*, *Mycobacterium mageritense*, *Mycobacterium brisbanense*, *Mycobacterium cosmeticum*, *Mycobacterium parafortuitum*, *Mycobacterium austroafricanum*, *Mycobacterium diernhoferi*, *Mycobacterium hodieri*, *Mycobacterium neoaurum*, *Mycobacterium prederkisbergense*, *Mycobacterium aurum*, *Mycobacterium vaccae*, *Mycobacterium chitae*, *Mycobacterium fallax*, *Mycobacterium confluentis*, *Mycobacterium flavenscens*, *Mycobacterium madagascariense*, *Mycobacterium phlei*, *Mycobacterium smegmatis*, *Mycobacterium goodie*, *Mycobacterium colinskui*, *Mycobacterium thermoresistbile*, *Mycobacterium gadium*, *Mycobacterium kormossense*, *Mycobacterium obuense*, *Mycobacterium sphagni*, *Mycobacterium agri*, *Mycobacterium aichiense*, *Mycobacterium alvei*, *Mycobacterium arupense*, *Mycobacterium brumae*, *Mycobacterium canariasense*, *Mycobacterium chubuense*, *Mycobacterium conceptionense*, *Mycobacterium duvalii*, *Mycobacterium elephantis*, *Mycobacterium gilvum*, *Mycobacterium hassiacum*, *Mycobacterium holsaticum*, *Mycobacterium immunogenum*, *Mycobacterium massiliense*, *Mycobacterium moriokaense*, *Mycobacterium psychrotoleranse*, *Mycobacterium pyrenivorans*, *Mycobacterium vanbaalenii*, *Mycobacterium pulveris*, *Mycobacterium arosiense*, *Mycobacterium aubagnense*, *Mycobacterium caprae*, *Mycobacterium chlorophenolicum*, *Mycobacterium fluoroanthenivorans*, *Mycobacterium kumamotonense*, *Mycobacterium novocastrense*, *Mycobacterium parmense*, *Mycobacterium phocaicum*, *Mycobacterium poriferae*, *Mycobacterium rhodesiae*, *Mycobacterium seolense*, *Mycobacterium tokalense*, *Mycobacterium xenopi*; *Mycobacterium scrofulaceum*; *Mycobacterium abscessus*; *Mycobacterium chelonae*; *Mycobacterium haemophilum*; *Mycobacterium leprae*; *Mycobacterium marinum*; *Mycobacterium fortuitum*; *Mycobacterium bovis*; *Mycobacterium ulcerans*; *Mycobacterium pseudoshottsii*, *Mycobacterium shottsii*, *Mycobacterium intracellulare*; *Mycobacterium tuberculosis* complex (MTC); *Mycobacterium avian-intracellulare* complex (MAIC) member and *Mycobacterium avium* complex (MAC) member.

In related aspects, the mycobacterium is *Mycobacterium tuberculosis*. In other aspects, the mycobacterium is *Mycobacterium avium*, *Mycobacterium kansasii*, *Mycobacterium malmoense*, *Mycobacterium simiae*, *Mycobacterium szulgai*, *Mycobacterium xenopi*, *Mycobacterium scrofulaceum*, *Mycobacterium abscessus*, *Mycobacterium chelonae*, *Mycobacterium haemophilum*, *Mycobacterium leprae*, *Mycobacterium marinum*, *M. fortuitum*, *Mycobacterium bovis*, *M. bovis* BCG, *M. africanum*, *M. canetti*, *M. caprae*, *M. microti*, *M. pinnipedi*, *M. leprae* or *Mycobacterium ulcerans*. In related embodiments, the mycobacterium is a subspecies (subsp.) of *Mycobacterium avium*, including *Mycobacterium avium* subsp. *avium*, *Mycobacterium avium* subsp. *hominissuis*, *Mycobacterium avium* subsp. *silvaticum*, and *Mycobacterium avium* subsp. *paratuberculosis*. In another related embodiment, the mycobacterium is *Mycobacterium intracellulare*. In further related embodiments, the mycobacterium is a member of the *Mycobacterium* tuberculosis complex. (MTC) the *Mycobacterium avium* complex (MAC) or the *Mycobacterium* avian-*intracellulare* complex (MAIC). In related embodiments, the mycobacterium is a non-tuberculosis complex or clade, including: *Mycobacterium avium* complex; *Mycobacterium gordonae* clade; *Mycobacterium kansasii* clade; *Mycobacterium chelonae* clade; *Mycobacterium fortuitum* clade; *Mycobacterium parafortuitum* clade; and *Mycobacterium vaccae* clade. In a related embodiment, the mycobacteria is a *Mycobacterium tuberculosis*.

In an exemplary embodiment, the mycobacteria in the methods described herein comprises a resistant mycobacterium, particularly a resistant or multiresistance *Mycobacterium tuberculosis*. In an exemplary embodiment, the resistant mycobacterium is a mutation of a mycobacteria described herein.

Methods of Treating and/or Preventing Disease

The combinations of the present invention exhibit potency against mycobacteria, and therefore have the potential to achieve therapeutic efficacy in animals, including humans.

The compounds described herein, and/or the formulations described herein exhibit potency against mycobacteria, and therefore have the potential to achieve therapeutic efficacy in animals, including humans.

In another aspect, the invention provides a method of treating and/or preventing a disease. The method includes administering to the animal a therapeutically effective amount of a combination of the invention, sufficient to treat and/or prevent the disease. In an exemplary embodiment, the combination of the invention can be used in human or veterinary medical therapy, particularly in the treatment or prophylaxis of mycobacterial-associated disease. In an exemplary embodiment, the combination is described herein.

In another aspect, the invention provides a method of treating and/or preventing a disease. The method includes administering to the animal a therapeutically effective amount of a compound as descrbed herein, or a formulation as described herein, sufficient to treat and/or prevent the disease. In an exemplary embodiment, the combination of the invention can be used in human or veterinary medical therapy, particularly in the treatment or prophylaxis of mycobacterial-associated disease. In an exemplary embodiment, the combination is described herein.

In another exemplary embodiment, the animal is as defined herein. In another exemplary embodiment, the disease a systemic disease or a cutaneous disease. In another exemplary embodiment, the disease is a respiratory disease.

Abbreviations

In describing the invention, chemical elements are identified in accordance with the Periodic Table of the Elements. Abbreviations and symbols utilized herein are in accordance with the common usage of such abbreviations and symbols by those skilled in the chemical arts. The following abbreviations are used herein:

AcOH acetic acid
Ac$_2$O acetic anhydride
AIBN 2-2'-Azoisobutyronitrile
BOC N-tert-butoxycarbonyl
BOC anhydride di-tert-butyl dicarbonate
B$_2$pin$_2$ bis(pinacolato)diboron diboron, also known as 4,4,4',4',5,5,5',5'-octamethyl-2,2'-bi(1,3,2-dioxaborolane
Celite® a filter aid composed of acid-washed diatomaceous silica, (a trademark of Manville Corp., Denver, Colo.)
CTAB cetyltrimethylammonium bromide
CD$_3$OD deuterated methanol
DCM dichloromethane
DIAD diisopropyl azodicarboxylate
DIBAL-H diisobutyl aluminium hydride
DME dimethoxyethane
DCE dichloroethane
DMF dimethylformamide
DMSO-d6 deuterated dimethylsulfoxide
DMSO dimethylsulfoxide
ESI Electrospray ionization
ES MS Electrospray mass spectrometry
Et$_2$O diethyl ether
EtOH ethanol
EtOAc, EA ethyl acetate
h hours
HPLC high performance liquid chromatography
KOAc potassium acetate
LCMS Liquid chromatography mass spectroscopy
mCPBA meta-chloro perbenzoic acid
MeNO$_2$ nitromethane
MeOH methanol
NBS N-bromosuccinimide
NCS N-chlorosuccinimide
NIS N-iodosuccinimide
NXS N-halosuccinimide
NaBH(OAc)$_3$ sodium triacetoxyborohydride
NMR Nuclear Magnetic Resonance spectroscopy
PE petroleum ether
PPh$_3$ triphenylphosphine
rt or r.t. room temperature
RT retention time
SFC supercritical fluid chromatography
t-BuOMe methyl t-butyl ether
TFA trifluoroacetic acid
THF tetrahydrofuran
uv ultraviolet

EXAMPLES

The following examples illustrate the invention. These Examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made. References to preparations carried out in a similar manner to, or by the general method of, other preparations, may encompass variations in routine parameters such as time, temperature, workup conditions, minor changes in reagent amounts etc.

Proton nuclear magnetic resonance ($^1$H NMR) spectra were recorded, and chemical shifts are reported in parts per million (δ) downfield relative the proton signal for tetramethylsilane (TMS) using the residual non-fully deuterated solvent as a reference Abbreviations for NMR data are as follows: s=singlet, d=doublet, t=triplet, q=quartet, m=multiplet, dd=doublet of doublets, dt=doublet of triplets, app=apparent, br=broad. Mass spectra were obtained using electrospray (ES) ionization techniques. All temperatures are reported in degrees centigrade.

Structure Determination
Open Form

Solution phase NMR was performed on G26-CH$_3$ using $^{13}$C NMR and $^1$H NMR. $^1$H spectrum with homonuclear decoupling (100 kHz DUMBO) Spectrum corrected for chemical shiftscaling.

Figure 3:
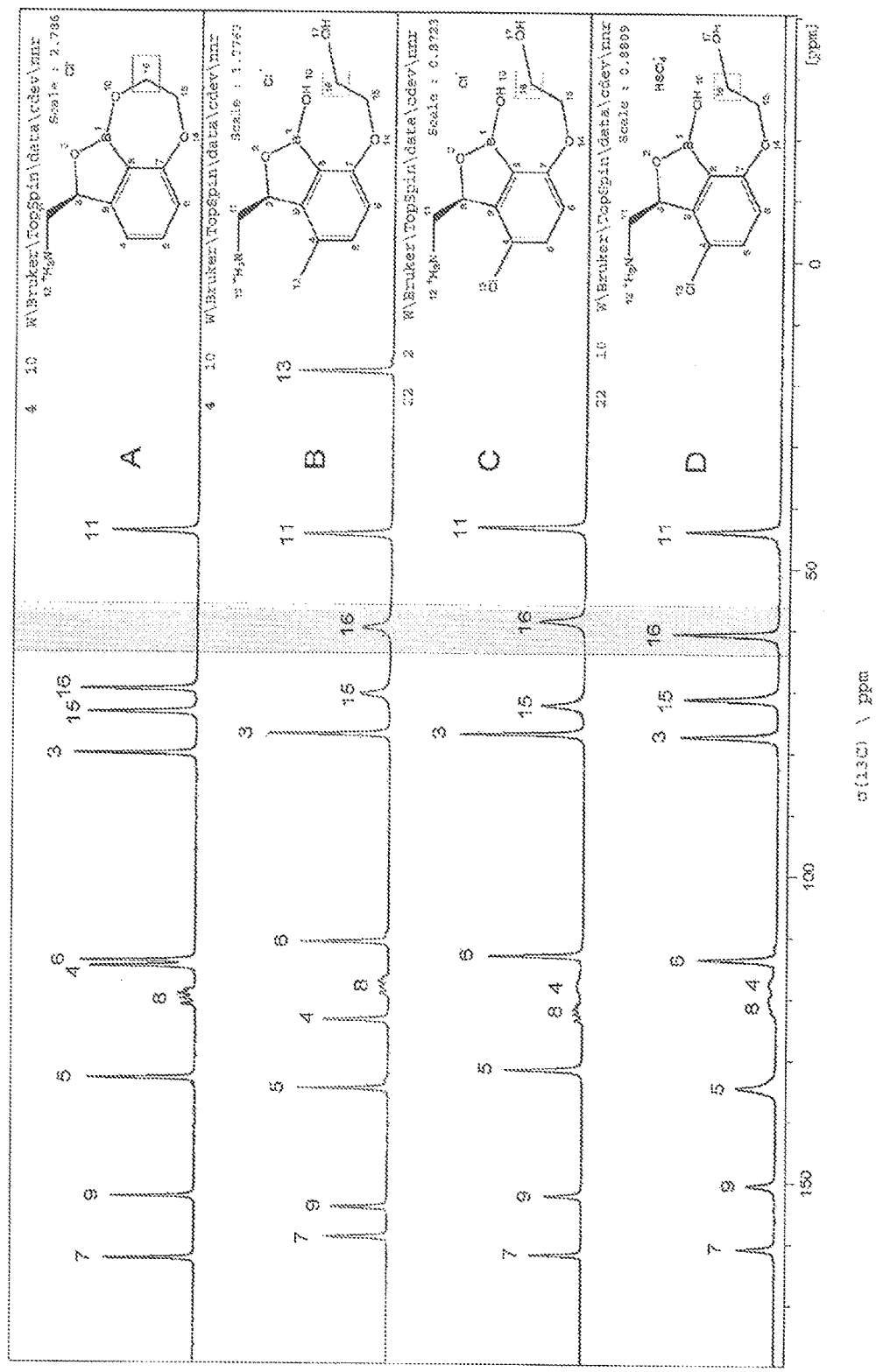
FIG. 3A shows the $^{13}$C solution NMR spectrum for the closed form structure of C2-H.
FIG. 3B shows the $^{13}$C solution NMR spectrum for the closed form structure of G26-CH3.
FIGS. 3C and 3D show the $^{13}$C solution NMR spectrum for the closed form structure of G4-CI.

Assignments of $^{13}C$ resonances were confirmed by other NMR data of the analog compound G4-Cl. The resonance of C8 showed J coupling to the neighboring quadrupolar 11B nucleus, observed as 4 lines. Chemical shift of C16 at 59.9 ppm is consistent with a ring open form. The closed ring form of G26-CH3 is expected to give a chemical shift of about 69 ppm for C16. This can be seen by comparing the C4H analog in FIG. 3B to that shown for C16 for G26-CH$_3$ in FIG. 3A. This same chemical shift (FIGS. 3C and 3D) was also experimentally observed in solution state NMR spectra of the G4-Cl analog having a Cl at position 4 of the benzoxaborole ring rather than a CH$_3$ as in G26-CH$_3$ (compare shaded peak in the spectra in FIGS. 3A, 3B, 3C and 3D).

Solid State NMR was Performed was Also Performed on G26-CH$_3$.

Figure 5:
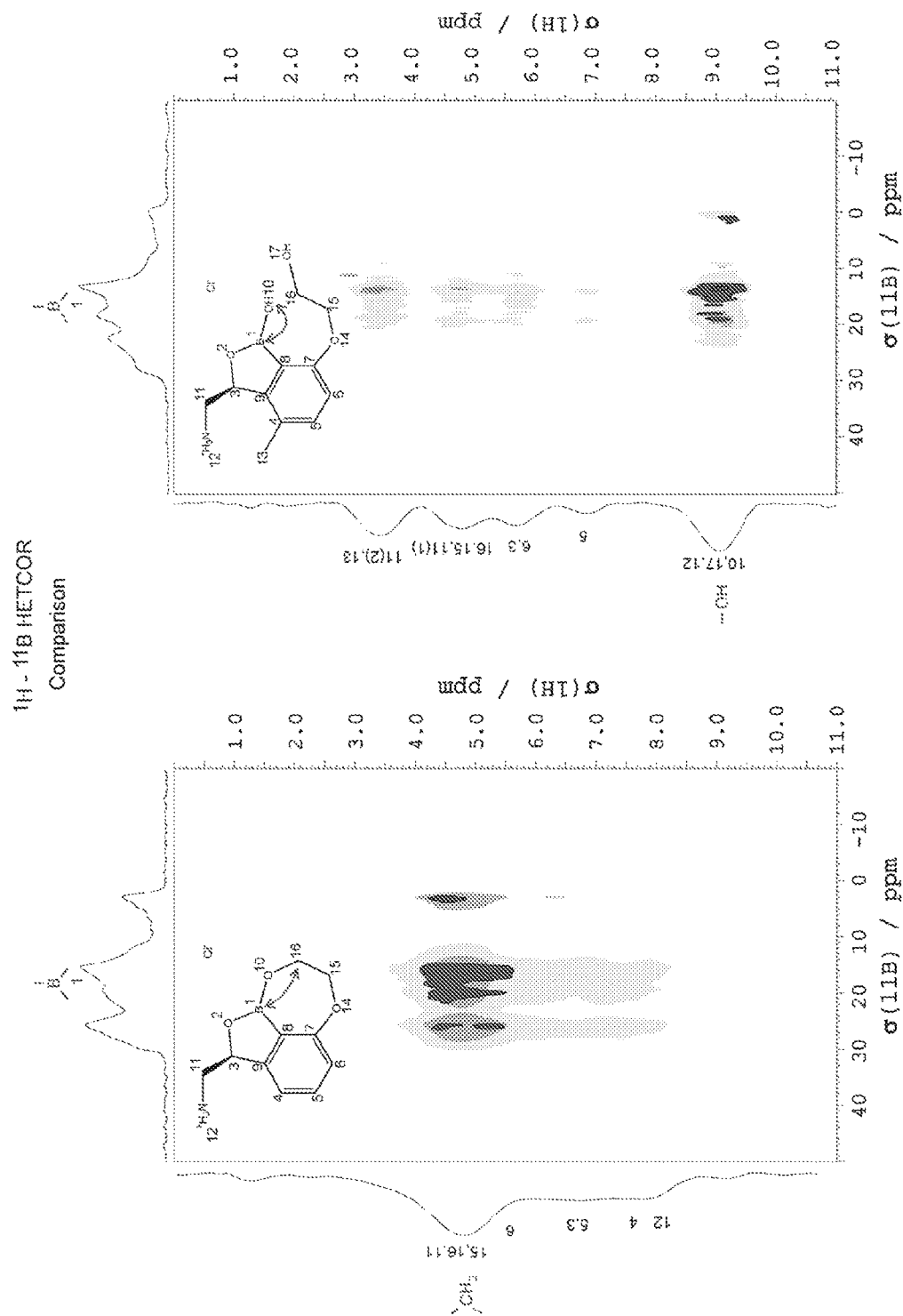
FIGS. 5A and 5B are ssNMR spectra showing $^1$H-$^{11}$B HETCOR coupling for C2-H, a ring closed compound (5A) and G26-CH$_3$, a ring open compound (5B).

Solid-state NMR data (see FIG. 4) point to a ring-open structure. In the $^{13}C$ CP spectrum the carbon C16 resonance has a chemical shift value of ca. 60 ppm, which is consistent with a ring-open structure. Additionally acquired $^1H$-11B HETCOR spectra (see FIG. 5) show strong correlations between B1 and OH protons at high ppm-values. This is also consistent with a ring-open structure with an —OH proton in proximity to B1. Fit of the second-order quadrupolar lineshape of the 11B spectrum led to values which are similar to literature values for similar ring-open structures.

Reactions involving metal hydrides including lithium hydride, lithium aluminium hydride, di-isobutylaluminium hydride, sodium hydride, sodium borohydride and sodium triacetoxyborohydride are carried out under argon unless otherwise specified.

Synthesis

Intermediate 1

(S)-tert-butyl ((7,8-dihydro-2H-1,6,9-trioxa-9a-borabenzo[cd]azulen-2-yl)methyl)carbamate a) (Z)-1-(pyridin-2-yl)-N-((1R)-1,7,7-trimethylbicyclo[2.2.1]heptan-2-ylidene)methanamine

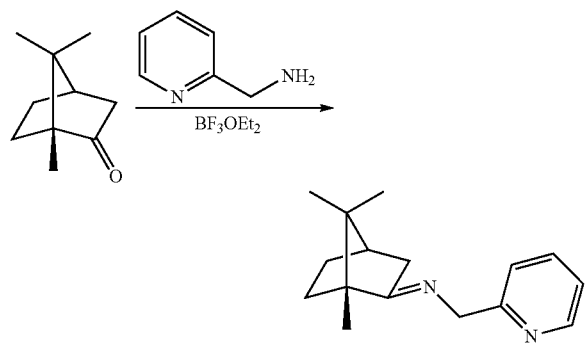

A mixture of (+)-camphor (371 g, 2.44 mol), pyridin-2-ylmethanamine (277 g, 2.56 mol) and BF$_3$.Et$_2$O (17 g, 0.12 mol) in toluene (3.7 L) was charged into a 5 L round bottom flask equipped with a Dean Stark trap, reflux condenser, thermometer and nitrogen inlet. The mixture was heated to reflux with azeotropic removal of water for 20 h. The mixture was cooled to 15° C. and quenched with 5% aqueous sodium bicarbonate (2.5 L), the organic phase was separated and washed with water (1.25 L×2), then the mixture was concentrated down to 2 L under vacuum. The residue was used in next step without purification. $^1H$ NMR (400 MHz, DMSO-d$_6$): 8.47-8.48 (d, J=4.4 Hz, 1H), 8.77-8.74 (t, J=7.6 Hz, 1H), 7.43-7.41 (d, J=8.0 Hz, 1H), 7.25-7.22 (dd, J=4.8 Hz, 1H), 4.49-4.38 (dd, J=16.4 Hz, 2H), 2.46-2.42 (m, 1H), 1.97-1.93 (m, 2H), 1.84-1.79 (m, 1H), 1.71-1.64 (m, 1H), 1.33-1.22 (m, 2H), 0.93 (s, 3H), 0.92 (s, 3H), 0.73 (s, 3H). LCMS: [M+H]$^+$=243.

b) (1R)-1,7,7-trimethyl-N-(pyridin-2-ylmethyl)bicyclo[2.2.1]heptan-2-amine

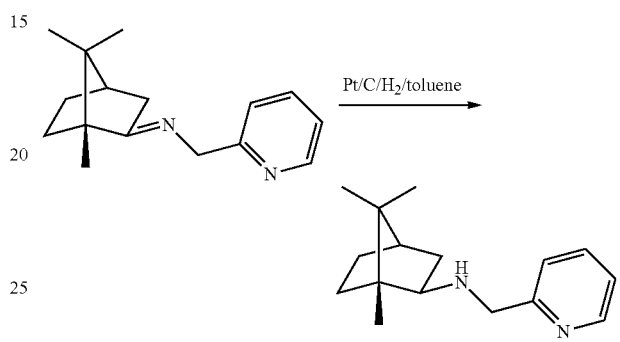

5% Pt/C (40 g) was charged into a 5 L pressure vessel, followed by a solution of (Z)-1-(pyridin-2-yl)-N-((1R)-1,7,7-trimethylbicyclo[2.2.1]heptan-2-ylidene)methanamine (2.44 mol) in toluene (2 L). The vessel was pressurized with 100 psi hydrogen for a period of 12 h. The solid was filtered through Celite® and the cake was washed with toluene (1 L). The filtrate was concentrated under vacuum to obtain the desired product (435 g obtained, total yield: 73%, over two steps) as a pale yellow oil. $^1H$ NMR (400 MHz, DMSO-d$_6$): 8.49-8.48 (d, J=4.8 Hz, 1H), 7.75-7.71 (t, J=7.6 Hz, 1H), 7.40-7.38 (d, J=7.6 Hz, 1H), 7.24-7.21 (dd, J=5.2 Hz, 1H), 3.79-3.64 (dd, J=14.4 Hz, 2H), 2.53-2.49 (m, 1H), 1.99 (s, 1H), 1.68-1.42 (m, 5H), 1.05 (s, 3H), 0.87 (s, 3H), 0.78 (s, 3H), LCMS: [M+H]$^+$=245.

c) 3-(2-(benzyloxy)ethoxy)benzaldehyde

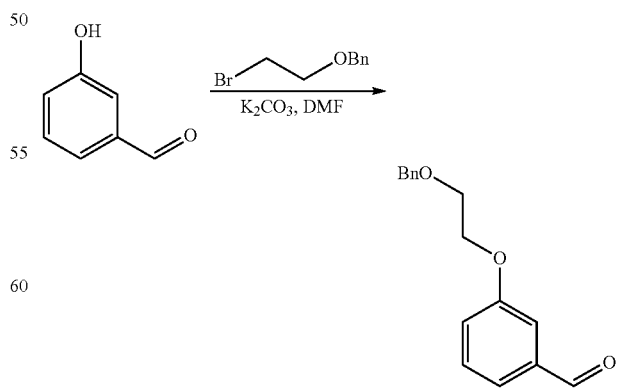

To a solution of 3-hydroxybenzaldehyde (2.90 kg, 23.75 mol), and ((2-bromoethoxy)methyl)benzene (4.26 kg, 19.79 mol) in DMF (9.3 L) was added K$_2$CO$_3$ (3.83 kg, 27.70 mol). The reaction mixture was stirred at r.t. for 24 h. Water (15 L) and tert-butyl methyl ether (23 L) were added to the reaction mixture. The organic phase was separated and washed with 1N NaOH (2×15 L) and water (15 L) sequentially, and then concentrated to a minimum. Ethanol (23 L) was added and the solution was concentrated under vacuum to afford the desired product (4.7 kg, 93%) as a colourless oil. $^1$H NMR (400 MHz, DMSO-d$_6$): 9.98 (s, 1H), 7.55-7.52 (m, 2H), 7.46 (s, 1H), 7.36-7.34 (m, 4H), 7.32-7.26 (m, 2H), 4.57 (s, 2H), 4.25-4.22 (t, J=4.4 Hz, 2H), 3.80-3.78 (t, J=4.4 Hz, 2H). LCMS: [M+Na]$^+$=279.

d) (S)-1-(3-(2-(benzyloxy)ethoxy)phenyl)-2-nitroethanol

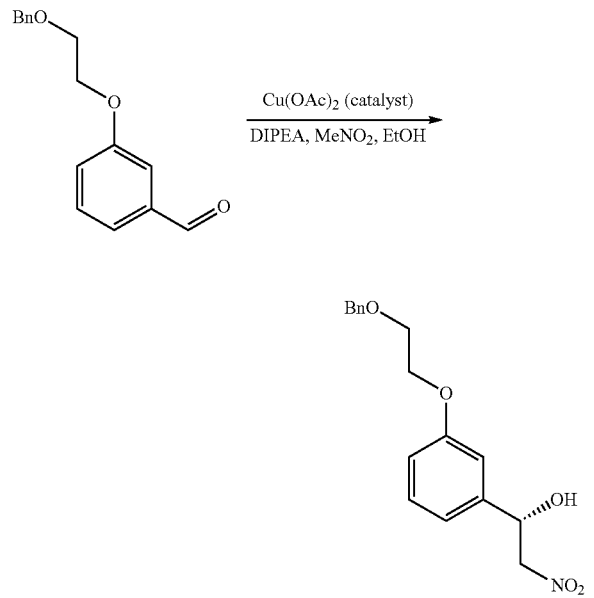

A mixture of copper (II) acetate (167 g, 0.92 mol), (1R)-1,7,7-trimethyl-N-(pyridin-2-ylmethyl)bicyclo[2.2.1]heptan-2-amine (269 g, 1.10 mol) in ethanol (19 L) was stirred at r.t. for 1 h, then a solution of 3-(2-(benzyloxy)ethoxy)benzaldehyde (4.70 kg, 18.34 mol) in ethanol (5 L) was added. The reaction mixture was cooled to a temperature range between −30° C. and −40° C., and then nitromethane (9.9 L, 183.40 mol) was added dropwise, keeping the temperature below −30° C., followed by the addition of diisopropylethylamine (285 g, 2.20 mol). The reaction was stirred at −30° C. for 24 h, and then quenched with trifluoroacetic acid (314 g, 2.75 mol). 1 N HCl (24 L) and TBME (47 L) were added to the resulting solution. The separated organic phase was washed with water (24 L) and then concentrated under vacuum. The residue was added to a mixture of petroleum ether/ethyl acetate=5:1 (10 L). Then the yellow solid was precipitated, and collected by filtration with Buchner funnel and dried under vacuum at 40° C. for 6 h to afford the desired product (5.00 kg, 86%) as a white solid. $^1$H NMR (400 MHz, DMSO-d$_6$): 7.38-7.25 (m, 6H), 7.03 (s, 1H), 7.01-6.99 (d, J=7.6 Hz, 1H), 6.90-6.87 (dd, J=8.0 Hz, 1H), 6.09-6.08 (d, J=5.2 Hz, 1H), 5.26-5.22 (m, 1H), 4.86-4.82 (dd, J=12.4 Hz, 1H), 4.57-4.51 (m, 3H), 4.15-4.13 (m, 2H), 3.78-3.76 (t, J=4.8 Hz, 2H). LC-MS: [M+Na]$^+$=340.

e) (S)-1-(3-(2-(benzyloxy)ethoxy)phenyl)-2-(dibenzylamino)ethanol hydrochloride

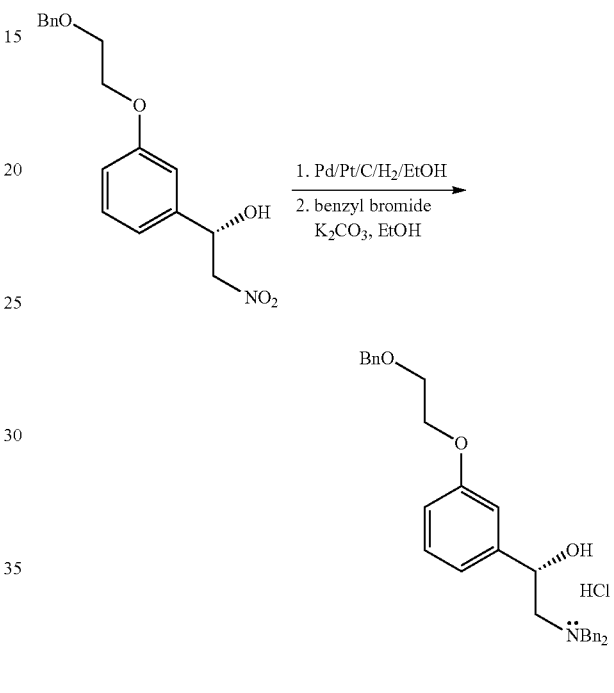

10% Pd/C (800 g) and 10% Pt/C (200 g) were charged to a pressure vessel, followed by a solution of (S)-1-(3-(2-(benzyloxy)ethoxy)phenyl)-2-nitroethanol (5.00 kg, 15.76 mol) in ethanol (50 L). The vessel was pressurized with 100 psi hydrogen for 12 h at r.t. The solid was filtered through Celite® and the cake was washed with ethanol (5 L). To the filtrate, K$_2$CO$_3$ (4.80 kg, 34.67 mol) and benzyl bromide (5.93 kg, 34.67 mol) were added sequentially. The reaction mixture was stirred at r.t. for 24 h. The solid was filtered and washed with ethanol (1 L). The filtrate was diluted with water (20 L) and then heated to 50° C. The solution was stirred at 50° C. for 30 min and then conc. HCl (1.5 L) was added dropwise over 1 h. The mixture was cooled to 0° C. and held at 0° C. for additional 30 min. The product was filtered and washed with 20% aqueous ethanol (1 L) to afford the hydrochloric salt of desired product (5.00 kg, 63% over two steps) as a colourless solid. $^1$H NMR (400 MHz, DMSO-d$_6$): 10.67 (s, 1H), 7.72-7.68 (m, 4H), 7.47-7.45 (m, 6H), 7.38-7.26 (m, 5H), 7.25-7.21 (t, J=7.6 Hz, 1H), 6.86-6.84 (d, J=8.0 Hz, 1H), 6.77 (s, 1H), 6.77-6.75 (d, J=7.2 Hz, 1H), 6.36 (s, 1H), 5.04-5.02 (d, J=9.2 Hz, 1H), 4.58 (s, 2H), 4.51-4.38 (m, 4H), 4.09-4.07 (t, J=4.0 Hz, 2H), 3.77-3.75 (t, J=3.2 Hz, 2H), 3.13-2.96 (m, 2H). LC-MS: [M+H]$^+$=468.

f) (S)-7-(2-(benzyloxy)ethoxy)-3-((dibenzylamino)methyl)benzo[c][1,2]oxaborol-1(3H)-ol

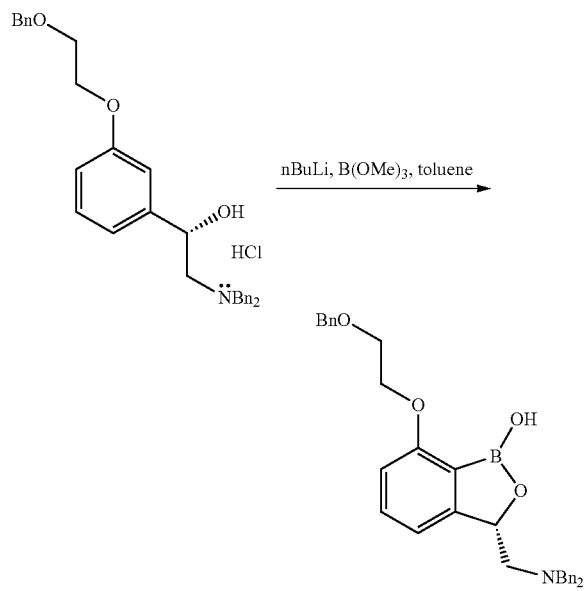

To a −30° C. solution of (S)-1-(3-(2-(benzyloxy)ethoxy)phenyl)-2-(dibenzylamino)ethanol hydrochloride (3.85 kg, 7.64 mol) in dry toluene (39 L) under N₂ atmosphere was added n-BuLi (15.3 L, 38.20 mol) dropwise over 6 h. After addition, the mixture was stirred at −30° C. for another 1 h, and then cooled to −70° C.; trimethyl borate (3.97 kg, 38.20 mol) was added dropwise keeping the temperature below −60° C. After addition, the reaction mixture was allowed to warm to r.t. and stirred overnight. The reaction was quenched with 5% aqueous NaHCO₃ (20 L) and stirred vigorously for 15 min, the resulting suspension was filtered and the filtrate was separated. The organic layer was washed with water (20 L×3) and concentrated under vacuum and the residue was purified by gel chromatography eluting with petroleum ether/ethyl acetate=5:1 to afford desired product (1.80 kg, 48%) as a yellow solid. ¹H NMR (400 MHz, DMSO-d₆): 8.81 (s, 1H), 7.39-7.22 (m, 16H), 6.82-6.80 (d, J=7.6 Hz, 1H), 6.72-6.70 (d, J=7.6 Hz, 1H), 5.34-5.31 (dd, J=7.6 Hz, 1H), 4.60 (s, 2H), 4.22-4.19 (t, J=4.4 Hz, 2H), 3.80-3.72 (m, 6H), 2.88-2.84 (dd, J=13.6 Hz, 1H), 2.47-2.45 (dd, J=10 Hz, 1H). LC-MS: [M+H]⁺=494.

g) (S)-(7,8-dihydro-2H-1,6,9-trioxa-9a-borabenzo[cd]azulen-2-yl)methanamine hydrochloride

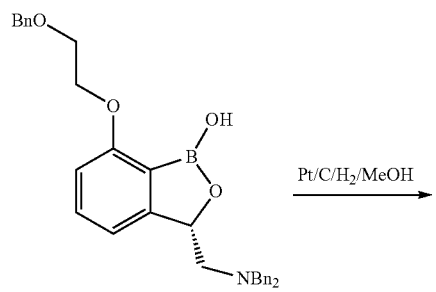

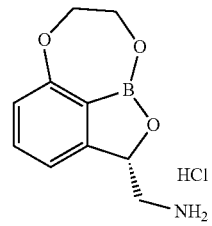

10% Pd/C (180 g) was charged to a pressure vessel, followed by a solution of (S)-7-(2-(benzyloxy)ethoxy)-3-((dibenzylamino)methyl)benzo[c][1,2]oxaborol-1(3H)-ol (1.80 kg, 3.65 mol) in methanol (18 L), toluene (3.6 L) and 1 N HCl (4 L). The vessel was pressurized with 100 psi hydrogen for a period of 12 h at 50° C. The solid was filtered through Celite and the cake was washed with methanol (1 L). The filtrate was concentrated under vacuum and the residue was treated with 2-propanol (3.6 L), stirred at r.t. for 30 min. The resulting solid was collected by filtration and washed with 2-propanol (500 mL), dried under vacuum at 50° C. for 6 h to afford the desired product (680 g, 77%) as a pale yellow powder. ¹H NMR (400 MHz, DMSO-d₆): 8.38 (s, 3H), 7.52-7.48 (t, J=8.0 Hz, 1H), 7.17-7.15 (d, J=7.6 Hz, 1H), 6.92-6.90 (d, J=7.6 Hz, 1H), 5.55 (m, 1H), 4.71-4.68 (m, 1H), 4.38-4.22 (m, 3H), 3.53-3.50 (m, 1H), 2.91-2.86 (m, 1H). LC-MS: [M+H]⁺=206.

h) (S)-tert-butyl ((7,8-dihydro-2H-1,6,9-trioxa-9a-borabenzo[cd]azulen-2-yl)methyl)carbamate

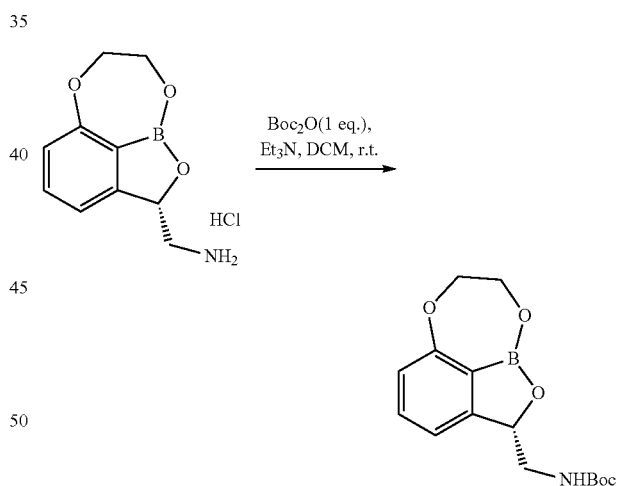

To a solution of (S)-(7,8-dihydro-2H-1,6,9-trioxa-9a-borabenzo[cd]azulen-2-yl)methanamine hydrochloride (390 g, 1.62 mol) and Et₃N (163.4 g, 4.85 mol) in DCM (4.6 L) was added (Boc)₂O (353.0 g 1.62 mol) dropwise over 2 h at r.t. After addition, the reaction mixture was stirred at r.t. for another 3 h. The reaction was quenched with 1N HCl (4 L) and the organic phase was separated and washed with water (4 L), concentrated under vacuum to obtain desired product (460 g, 93%) as a pale white solid. ¹H NMR (400 MHz, DMSO-d₆): 7.46-7.42 (t, J=7.6 Hz, 1H), 7.07 (s, 1H), 7.02-7.00 (d, J=7.2 Hz, 1H), 6.87-6.85 (d, J=8.0 Hz, 1H), 5.27 (m, 1H), 4.68-4.65 (m, 1H), 4.34-4.18 (m, 3H), 3.41 (s, 1H), 3.14-3.08 (m, 1H), 1.38 (s, 9H). LC-MS: [M-55]=250.

Example 2

(S)-(3-methyl-7,8-dihydro-2H-1,6,9-trioxa-9a-borabenzo[cd]azulen-2-yl)methanamine (G26-CH₃)

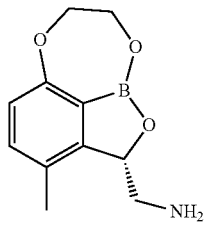 [SMILES: Cc1ccc2c3c1[C@@H](CN)OB3OCCO2]

a) (S)-tert-butyl ((3-bromo-7,8-dihydro-2H-1,6,9-trioxa-9a-borabenzo[cd]azulen-2-yl)methyl)carbamate

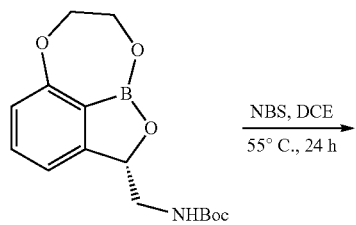

A solution of (S)-tert-butyl ((7,8-dihydro-2H-1,6,9-trioxa-9a-borabenzo[cd]azulen-2-yl)methyl)carbamate (3 g, 9.81 mmol) and NBS (1.92 g, 10.8 mmol) in 50 mL of dichloroethane was stirred at 55° C. for 24 hours. Then the mixture was poured into 150 mL of water, extracted with ethyl acetate (150 mL), washed with water (100 mL) and brine (100 mL). The organic layer was dried over anhydrous sodium sulfate, filtered and concentrated in vacuo. The residue was purified by silica gel chromatography eluting with a mixture of ethyl acetate and petroleum ether (1:4) to give the title compound (3.5 g, 93%) as light yellow oil. LC-MS: 384 [M+H]+.

b) (S)-tert-butyl ((3-methyl-7,8-dihydro-2H-1,6,9-trioxa-9a-borabenzo[cd]azulen-2-yl)methyl)carbamate

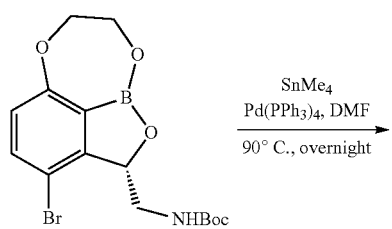

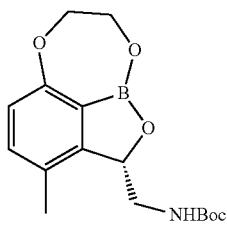

A solution of (S)-tert-butyl ((3-bromo-7,8-dihydro-2H-1,6,9-trioxa-9a-borabenzo[cd]azulen-2-yl)methyl)carbamate (500 mg, 1.31 mmol), tetramethylstannane (0.822 g, 4.57 mmol) and Pd(Ph₃)₄(151 mg, 0.131 mmol) in 10 mL of DMF was degassed with N₂ for six times. Then the mixture was heated at 90° C. for 16 hours. The reaction mixture was cooled to room temperature, and then the mixture was poured into 25 mL of water, extracted with ethyl acetate (25 mL), washed with water (15 mL) and brine (15 mL). The organic layer was dried over anhydrous sodium sulfate, filtered and concentrated in vacuo. The residue was purified by silica gel chromatography eluting with a mixture of ethyl acetate and petroleum ether (1:6) to give the title compound (150 mg, 36%) as light yellow oil. LC-MS: 320 [M+H]+.

c) (S)-(3-methyl-7,8-dihydro-2H-1,6,9-trioxa-9a-borabenzo[cd]azulen-2-yl)methanamine hydrochloride

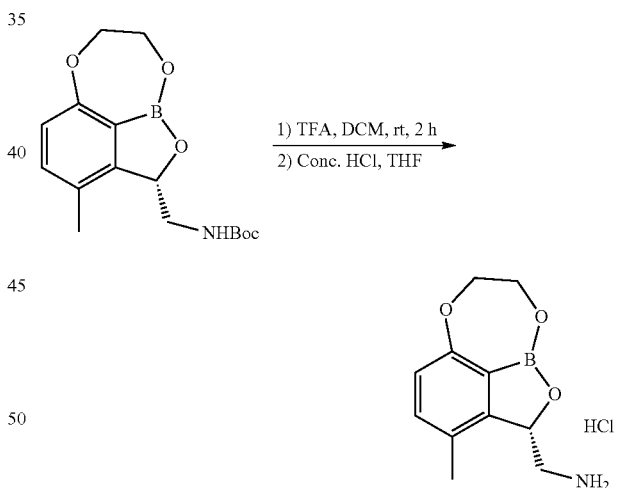

A solution of compound (S)-tert-butyl ((3-methyl-7,8-dihydro-2H-1,6,9-trioxa-9a-borabenzo[cd]azulen-2-yl)methyl)carbamate (150 mg, 0.47 mmol) and TFA (0.6 mL) in 5 mL of DCM was stirred at room temperature for 2 hours. The solvent was evaporated at 40° C. at reduced pressure and the residue was treated with 2 M HCl in Et₂O, then washed with Et₂O (10 mL) to give the title compound (13.6 mg, 11%) as white solid. LC-MS: 220.1 [M+H]+. 1H NMR (400 MHz, CD₃OD): δ 7.30 (d, 1H, J=8), 6.87 (d, 1H, J=8), 5.54 (brs, 1H), 4.67 (brs, 1H), 4.46-4.17 (m, 3H), 3.68 (brs, 1H), 2.99-2.98 (m, 1H), 2.33 (s, 3H).

Example 3

(S)-(3-methyl-7,8-dihydro-2H-1,6,9-trioxa-9a-borabenzo[cd]azulen-2-yl)methanamine (G27-phenyl)

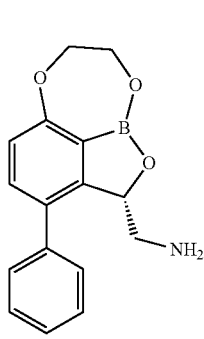 [SMILES: NC[C@H]1OB2OCCOc3ccc(-c4ccccc4)c1c32]

a) (S)-tert-butyl ((3-phenyl-7,8-dihydro-2H-1,6,9-trioxa-9a-borabenzo[cd]azulen-2-yl)methyl)carbamates

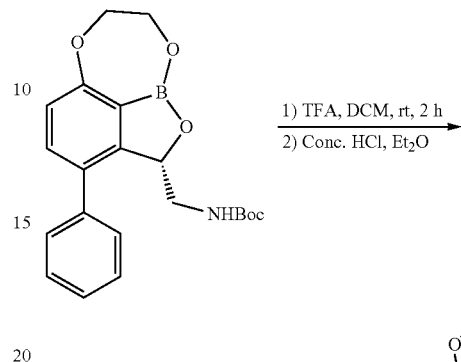

A solution of compound (S)-tert-butyl ((3-bromo-7,8-dihydro-2H-1,6,9-trioxa-9a-borabenzo[cd]azulen-2-yl)methyl)carbamate (400 mg, 1.04 mmol), tributyl (phenyl) stannane (1.68 g, 4.58 mmol) and Pd(Ph$_3$)$_4$(151 mg, 0.131 mmol) in 10 mL of DMF was degassed with N$_2$ for six times. Then the mixture was heated at 90° C. for 16 hours. The reaction mixture was cooled to room temperature, and then the mixture was poured into 20 mL of water, extracted with ethyl acetate (15 mL), washed with water (10 mL) and brine (10 mL). The organic layer was dried over anhydrous sodium sulfate, filtered and concentrated in vacuo. The residue was purified by silica gel chromatography eluting with a mixture of ethyl acetate and petroleum ether (1:6) to give the title compound (140 mg, 35%) as light yellow oil. LC-MS: 382 [M+H]+.

b) (S)-(3-phenyl-7,8-dihydro-2H-1,6,9-trioxa-9a-borabenzo[cd]azulen-2-yl)methanamine hydrochloride

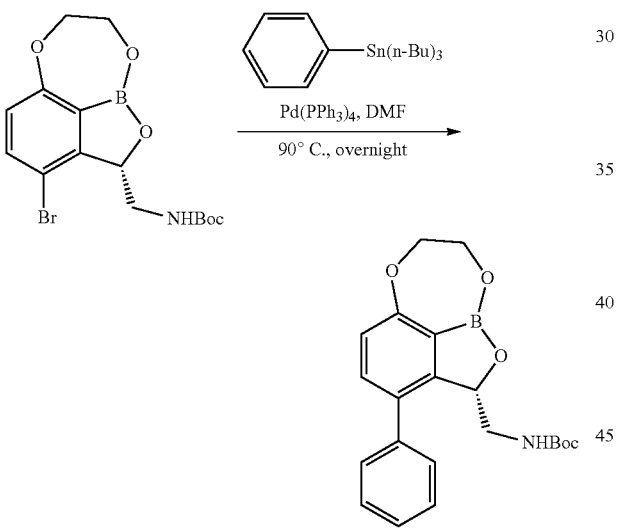

A solution of compound (S)-tert-butyl ((3-phenyl-7,8-dihydro-2H-1,6,9-trioxa-9a-borabenzo[cd]azulen-2-yl) methyl)carbamate (140 mg, 0.37 mmol) and TFA (0.5 mL) in 5 mL of DCM was stirred at room temperature for 2 hours. The solvent was evaporated at 40° C. at reduced pressure and the residue was treated with 2 M HCl in Et$_2$O, then washed with Et$_2$O (10 mL) to give the title compound (45 mg, 39%) as white solid. LC-MS: 282.1 [M+H]+. 1H NMR (400 MHz, DMSO-d6): δ 8.17-7.86 (m, 3H), 7.49-7.38 (m, 5H), 7.05 (d, 1H, J=8), 6.01 (brs, 1H), 4.78-4.68 (m, 1H), 4.46-4.24 (m, 3H), 3.32 (brs, 1H), 3.01-2.84 (m, 1H).

Example 4

(S)-(3-(thiophen-2-yl)-7,8-dihydro-2H-1,6,9-trioxa-9a-borabenzo[cd]azulen-2-yl)methanamine (G28-thienyl)

51 a) (S)-tert-butyl ((3-(thiophen-2-yl)-7,8-dihydro-2H-1,6,9-trioxa-9a-borabenzo[cd]azulen-2-yl)methyl)carbamate

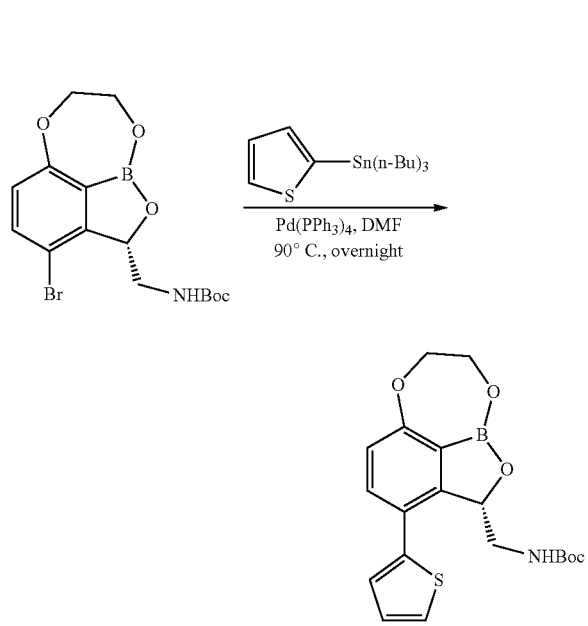

A solution of compound (S)-tert-butyl ((3-bromo-7,8-dihydro-2H-1,6,9-trioxa-9a-borabenzo[cd]azulen-2-yl)methyl)carbamate (400 mg, 1.04 mmol), tributyl(thiophen-2-yl)stannane (1.37 g, 3.66 mmol) and Pd(Ph₃)₄ (120 mg, 0.104 mmol) in 10 mL of DMF was degassed with $N_2$ for six times. Then the mixture was heated at 90° C. for 16 hours. The reaction mixture was cooled to room temperature, and then the mixture was poured into 20 mL of water, extracted with ethyl acetate (12 mL), washed with water (10 mL) and brine (10 mL). The organic layer was dried over anhydrous sodium sulfate, filtered and concentrated in vacuo. The residue was purified by silica gel chromatography eluting with a mixture of ethyl acetate and petroleum ether (1:5) to give the title compound (160 mg, 40%) as light yellow oil. LC-MS: 388 [M+H]+.

b) (S)-(3-(thiophen-2-yl)-7,8-dihydro-2H-1,6,9-trioxa-9a-borabenzo[cd]azulen-2-yl)methanamine hydrochloride

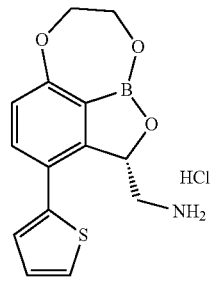

A solution of compound (S)-tert-butyl ((3-(thiophen-2-yl)-7,8-dihydro-2H-1,6,9-trioxa-9a-borabenzo[cd]azulen-2-yl)methyl)carbamate (160 mg, 0.41 mmol) and TFA (0.6 mL) in 5 mL of DCM was stirred at room temperature for 2 hours. The solvent was evaporated at 40° C. at reduced pressure and the residue was treated with 2 M HCl in Et₂O, then washed with Et₂O (10 mL) to give the title compound (38.2 mg, 29%) as white solid. LC-MS: 288.1 [M+H]+. 1H NMR (400 MHz, DMSO-d6): δ 7.99 (brs, 3H), 7.67 (d, 1H, J=8), 7.57 (d, 1H, J=8), 7.29 (d, 1H, J=4), 7.18 (d, 1H, J=4), 7.03 (d, 1H, J=12), 6.02-5.96 (m, 1H), 4.72-4.68 (m, 1H), 4.41 (brs, 2H), 4.29-4.18 (m, 1H), 3.00-2.93 (m, 1H), 2.65-2.52 (m, 1H).

Example 5

((2S)-3,8-dimethyl-7,8-dihydro-2H-1,6,9-trioxa-9a-borabenzo[cd]azulen-2-yl)methanamine a) 2-bromo-3-(2-hydroxypropoxy)benzaldehyde

A solution of 2-bromo-3-hydroxybenzaldehyde (6.0 g, 29.85 mmol), 1-chloropropan-2-ol (8.46 g, 89.55 mmol) and K₂CO₃ (8.24, 59.7 mmol) in DMF (100 mL) was stirred at 100° C. overnight. Then the reaction mixture was quenched by adding water (4 L) and then extracted with EtOAc (3×1.5 L). The combined organic layers were washed with brine (250 mL), dried over anhydrous Na₂SO₄ and concentrated to dryness in vacuo. The residue was purified by column chromatography on silica gel (petroleum ether:ethyl acetate=5:1 to 2:1) to give the target crude compound (8.77 g). MS (ESI) m/z=259/261 [M+H]+.

b) 3-(2-hydroxypropoxy)-2-(4,4,5,5-tetramethyl-1,3,2-dioxaborolan-2-yl)benzaldehyde

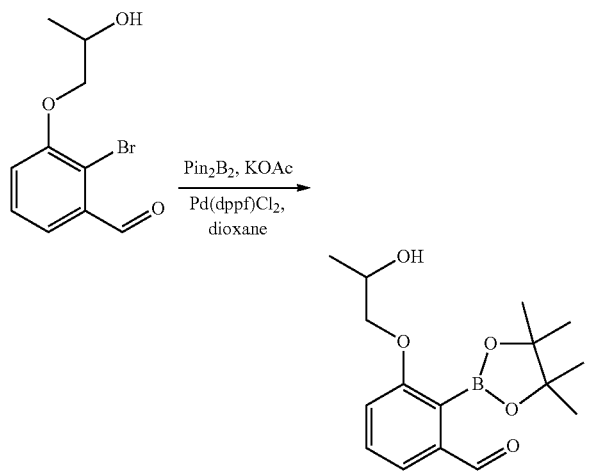

A solution of 2-bromo-3-(2-hydroxypropoxy)benzaldehyde (8.77 g, 34 mmol) 4,4,4',4',5,5,5',5'-octamethyl-2,2'-bi(1,3,2-dioxaborolane) (17.27 g, 68 mmol), Pd(dppf)Cl₂ (2.49 g, 3.4 mmol) and KOAc (9.99 g, 102 mmol) in dioxane (200 mL) was stirred at 100° C. overnight. Then the reaction mixture was quenched by adding water (200 mL) and then extracted with EtOAc (3×200 mL). The combined organic layers were washed with brine (250 mL), dried over anhydrous Na₂SO₄ and concentrated to dryness in vacuo. The residue was purified by column chromatography on silica gel (petroleum ether:ethyl acetate=5:1 to 1:1) to give the target crude compound (6 g). MS (ESI) m/z=307 [M+H]+.

c) 8-methyl-2-(nitromethyl)-7,8-dihydro-2H-1,6,9-trioxa-9a-borabenzo[cd]azulene

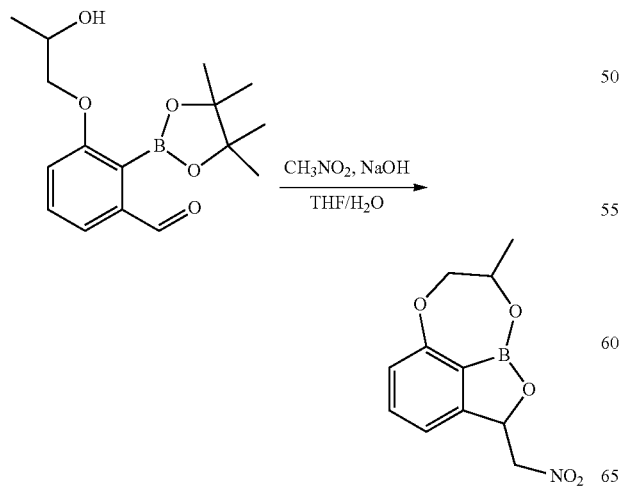

To a solution of NaOH (261.4 mg, 6.54 mmol) in water (8 mL) was added nitromethane (1.2 g, 19.6 mmol) at 5-10° C. After stirring for 15 min at 5-10° C., CTAB (0.19 g, 0.52 mmol) was added to the reaction mixture and followed by the addition of 3-(2-hydroxypropoxy)-2-(4,4,5,5-tetramethyl-1,3,2-dioxaborolan-2-yl)benzaldehyde (2.0 g, 6.54 mmol) at 5-10° C. The reaction mixture was stirred at rt for 5 h. The reaction mixture was acidified to pH=1 using diluted hydrochloric acid and stirred at rt overnight. The reaction mixture was filtered to give the target compound (541 mg, 33%).

d) (8-methyl-7,8-dihydro-2H-1,6,9-trioxa-9a-borabenzo[cd]azulen-2-yl)methanamine acetate

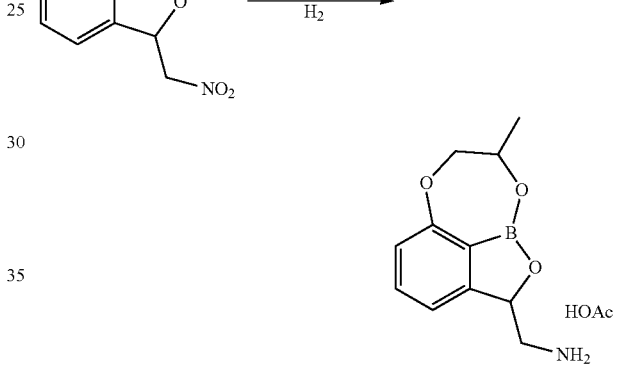

A solution of 8-methyl-2-(nitromethyl)-7,8-dihydro-2H-1,6,9-trioxa-9a-borabenzo[cd]azulene (541 mg, 2.173 mmol) and palladium hydroxide (300 mg) in acetic acid (10 mL) was shaken under an atmosphere of H₂ overnight at room temperature. The mixture was filtered through a bed of Celite and the filtrate was concentrated in vacuo to give the crude compound (350 mg). MS (ESI) m/z=220 [M+H]+.

e) tert-butyl ((8-methyl-7,8-dihydro-2H-1,6,9-trioxa-9a-borabenzo[cd]azulen-2-yl)methyl)carbamate

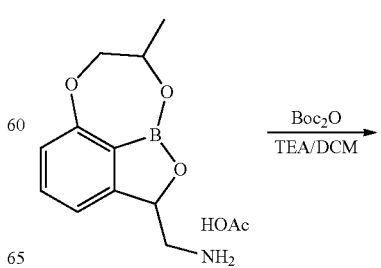

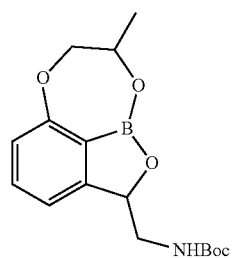

To the mixture of crude compound (8-methyl-7,8-dihydro-2H-1,6,9-trioxa-9a-borabenzo[cd]azulen-2-yl)methanamine acetate (3.0 g, 10.75 mmol) and triethylamine (6.5 g, 64.5 mmol) in dichloromethane (100 mL) at 0° C. was added di-tert-butyl dicarbonate (3.5 g, 16.13 mmol) and the mixture was stirred for 2 h at room temperature. The reaction was quenched with sat. NaHCO$_3$ (15 mL) and the resulting mixture was extracted with EtOAc (3×80 mL), the combined organic layers were dried over anhydrous Na$_2$SO$_4$ and concentrated in vacuo. The residue was purified by preparative-HPLC using a Daisogel 10μ C18 column (250×50 mm), eluted with gradient water/acetonitrile (0.05% TFA) to give the product (700 mg). MS (ESI) m/z=264 [M-56]$^+$. $^1$H NMR (300 MHz, DMSO-d$_6$): δ 7.44-7.39 (m, 1H), 7.01-6.98 (m, 2H), 6.88-6.85 (m, 1H), 5.24 (m, 1H), 4.52-4.44 (m, 2H) 4.18-4.00 (m, 1H), 3.39-3.36 (m, 1H), 3.15-3.06 (m, 1H), 1.42-1.09 (m, 15H).

f) tert-butyl ((3-bromo-8-methyl-7,8-dihydro-2H-1,6,9-trioxa-9a-borabenzo[cd]azulen-2-yl)methyl)carbamate

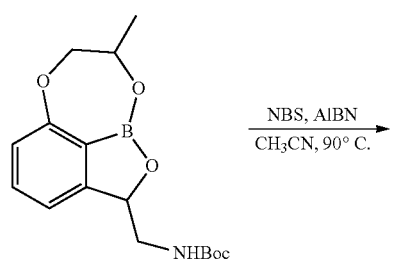

To a solution of tert-butyl ((8-methyl-7,8-dihydro-2H-1,6,9-trioxa-9a-borabenzo[cd]azulen-2-yl)methyl)carbamate (180 mg, 0.564 mmol) and 1-bromopyrrolidine-2,5-dione (120 mg, 0.677 mmol) in CH$_3$CN (20 mL) was added 2,2'-Azobis(2-methylpropionitrile) (9.2 mg, 0.056 mmol) and the mixture was stirred for 2 h at 90° C. The reaction mixture was then concentrated in high vacuo and the residue was purified by preparative-HPLC using a Gemini® 5 u C18 column (150×21.2 mm) eluted with gradient water/acetonitrile (0.05% TFA) to give the product (60 mg). MS (ESI) m/z=342/344 [M-56]$^+$.

g) tert-butyl ((3,8-dimethyl-7,8-dihydro-2H-1,6,9-trioxa-9a-borabenzo[cd]azulen-2-yl)methyl)carbamate

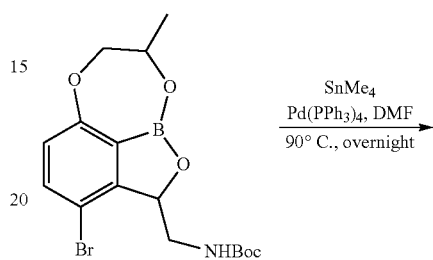

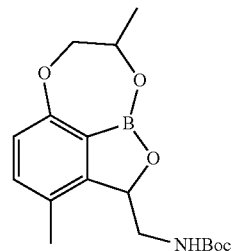

A solution of tert-butyl ((3-bromo-8-methyl-7,8-dihydro-2H-1,6,9-trioxa-9a-borabenzo[cd]azulen-2-yl)methyl)carbamate (1 eq.), tetramethylstannane (approx. 3.5-4.5 eq., approx. 3.9 eq.) and Pd(Ph$_3$)$_4$(approx. 0.01 to 0.5 eq., approx. 0.1 eq.) in DMF can be degassed with N$_2$. Then the mixture can be heated at between about 50° C. and 150° C. (about 90° C. for example) for between about 4 hours and 24 hours (about 16 hours for example). The reaction mixture can be cooled to room temperature, and then the mixture can be poured into water, can be extracted with ethyl acetate, and can be washed with water and brine. The organic layer can be dried over anhydrous sodium sulfate, filtered and concentrated in vacuo. The residue can be purified by silica gel chromatography eluting with a mixture of ethyl acetate and petroleum ether to give the title compound.

h) (3,8-dimethyl-7,8-dihydro-2H-1,6,9-trioxa-9a-borabenzo[cd]azulen-2-yl)methanamine hydrochloride

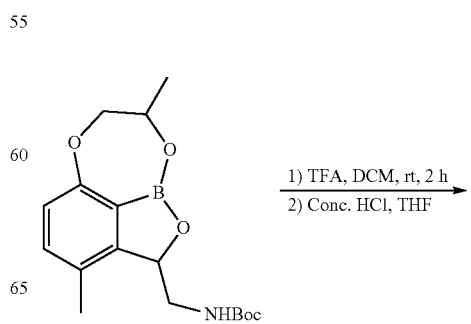

-continued

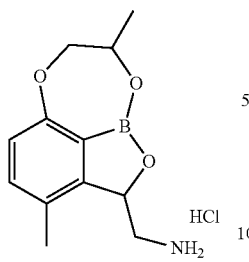

A solution of tert-butyl ((3,8-dimethyl-7,8-dihydro-2H-1,6,9-trioxa-9a-borabenzo[cd]azulen-2-yl)methyl)carbamates and TFA in 5 mL of DCM can be stirred at room temperature for 2 hours. The solvent can be evaporated at reduced pressure and the residue can be treated with 2 M HCl in ether, then can be washed with ether to give the title compound.

Example 6

(3,8,8-trimethyl-7,8-dihydro-2H-1,6,9-trioxa-9a-borabenzo[cd]azulen-2-yl)methanamine

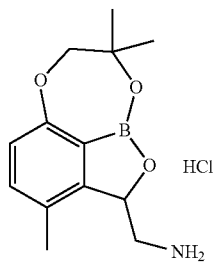 [SMILES: Cc1ccc2c3c1C(CN)OB3OC(C)(C)CO2 ; Cl]

a) 2-bromo-3-(2-hydroxy-2-methylpropoxy)benzaldehyde

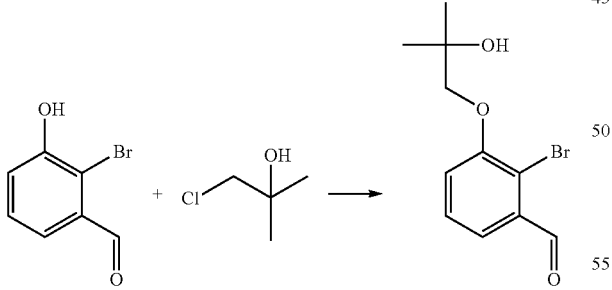

A solution of 2-bromo-3-hydroxybenzaldehyde (7.5 g, 37.3 mmol), 1-chloro-2-methylpropan-2-ol (9.4 g, 85.6 mmol) and Na$_2$CO$_3$ (6.7 g, 63.2 mmol) in 70 mL of DMSO was stirred at 140° C. for 3 hours. Then the mixture was cooled to room temperature, poured into 300 mL of water, extracted with ethyl acetate (600 mL), washed with water (300 mL), brine (50 mL), dried over anhydrous sodium sulfate. The solvent was evaporated at 40° C. under reduced pressure and the residue was purified by silica gel chromatography, eluting with a mixture of ethyl acetate and petroleum ether (1:3) to give the title compound (9.2 g, 90.3%) as a colorless oil. $^1$H NMR (300 MHz, CDCl$_3$): δ 10.43 (s, 1H), 7.54 (dd, 1H, J1=3.0, J2=7.5), 7.40~7.34 (m, 1H), 7.54 (dd, 1H, J1=3, J2=7.5), 3.90 (s, 2H), 1.42 (s, 6H).

b) 3-(2-hydroxy-2-methylpropoxy)-2-(4,4,5,5-tetramethyl-1,3,2-dioxaborolan-2-yl)benzaldehyde

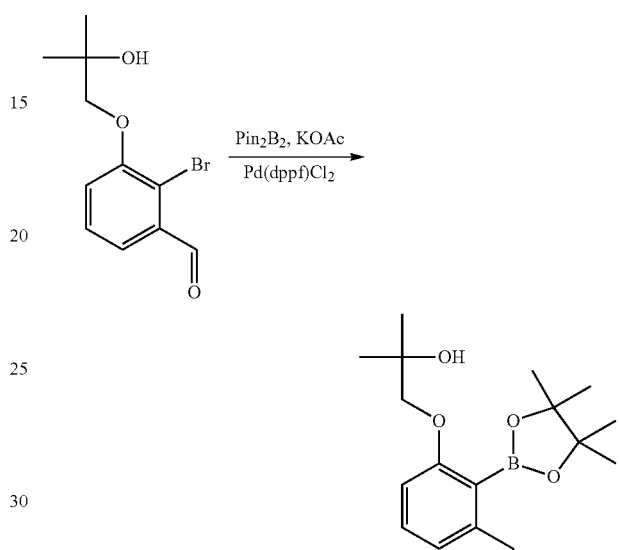

A solution of 2-bromo-3-(2-hydroxy-2-methylpropoxy)benzaldehyde (9.2 g, 33.7 mmol), Pin$_2$B$_2$ (17.1 g, 67.4 mmol), KOAc (9.9 g, 101.1 mmol) and Pd(dppf)Cl$_2$ (2.5 g) in 240 mL of 1,4-dioxane was degassed with N$_2$ for six times. Then the reaction was stirred at 99° C. under nitrogen for 16 hours. The reaction was cooled, filtered, then evaporated at 40° C. under reduced pressure and the residue was purified by silica gel chromatography, eluting with a mixture of ethyl acetate and petroleum ether (1:5) to give the title compound (10 g, crude) including de-Br by-product (used directly in the next step without further purification).

c) 8,8-dimethyl-2-(nitromethyl)-7,8-dihydro-2H-1,6,9-trioxa-9a-borabenzo[cd]azulene

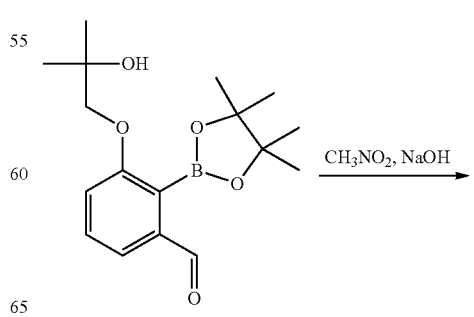

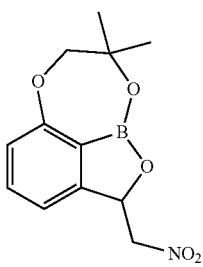

To a stirred solution of 3-(2-hydroxy-2-methylpropoxy)-2-(4,4,5,5-tetramethyl-1,3,2-dioxaborolan-2-yl)benzaldehyde (10 g, 31.3 mmol) and $CH_3NO_2$ (5.7 g, 93.8 mmol) in 100 mL of THF was added a solution of NaOH (1.25 g, 31.3 mmol) in 60 mL of water at room temperature. Then the reaction was stirred at room temperature for 16 hours. Then the reaction was acidified by conc. HCl to pH=1 at 0° C. and stirred at room temperature for 1 hour. The mixture was extracted with ethyl acetate (100 mL), washed with water (30 mL), then brine (30 mL), dried over anhydrous sodium sulphate. The solvent was evaporated at 40° C. under reduced pressure and the residue was purified by silica gel chromatography eluting with a mixture of ethyl acetate and petroleum ether (1:10) to give the title compound (3 g, 36.5%) as a colourless oil.

d) (8,8-dimethyl-7,8-dihydro-2H-1,6,9-trioxa-9a-borabenzo[cd]azulen-2-yl)methanamine acetate A solution of 8,8-dimethyl-2-(nitromethyl)-7,8-dihydro-2H-1,6,9-trioxa-9a-borabenzo[cd]azulene (1 g, 3.8 mmol) and $Pd(OH)_2$ (10%, 0.2 g) in 20 mL of acetic acid was hydrogenated at 1 atm of $H_2$ at rt for 16 hours. Then the mixture was filtered and the solvent was evaporated at 40° C. under reduced pressure to give the title compound (0.9 g, crude) as an oil (acetate salt). LC-MS: 234.1 $[M+H]^+$.

e) tert-butyl ((8,8-dimethyl-7,8-dihydro-2H-1,6,9-trioxa-9a-borabenzo[cd]azulen-2-yl)methyl)carbamate

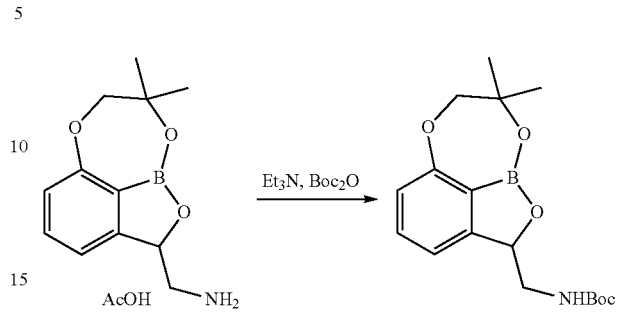

To a stirred solution of (8,8-dimethyl-7,8-dihydro-2H-1,6,9-trioxa-9a-borabenzo[cd]azulen-2-yl)methanamine acetate (0.7 g, 2.39 mmol) in 70 mL of $CH_2Cl_2$ cooled to 0° C. was added $Et_3N$ (0.61 g, 6.0 mmol). Then $Boc_2O$ (0.98 g, 4.5 mmol) was added in one portion, and the reaction was stirred at room temperature for 16 hours. The mixture was washed with 0.3 N HCl (30 mL), water (30 mL) and dried over anhydrous sodium sulphate. The solvent was evaporated at 40° C. at reduced pressure and the residue was purified by silica gel chromatography eluting with a mixture of ethyl acetate and petroleum ether (1:4) to give the title compound (0.63 g, 79%) as an oil. LC-MS: 234.1 $[M+H-100]^+$.

f) tert-butyl ((3-bromo-8,8-dimethyl-7,8-dihydro-2H-1,6,9-trioxa-9a-borabenzo[cd]azulen-2-yl)methyl)carbamate

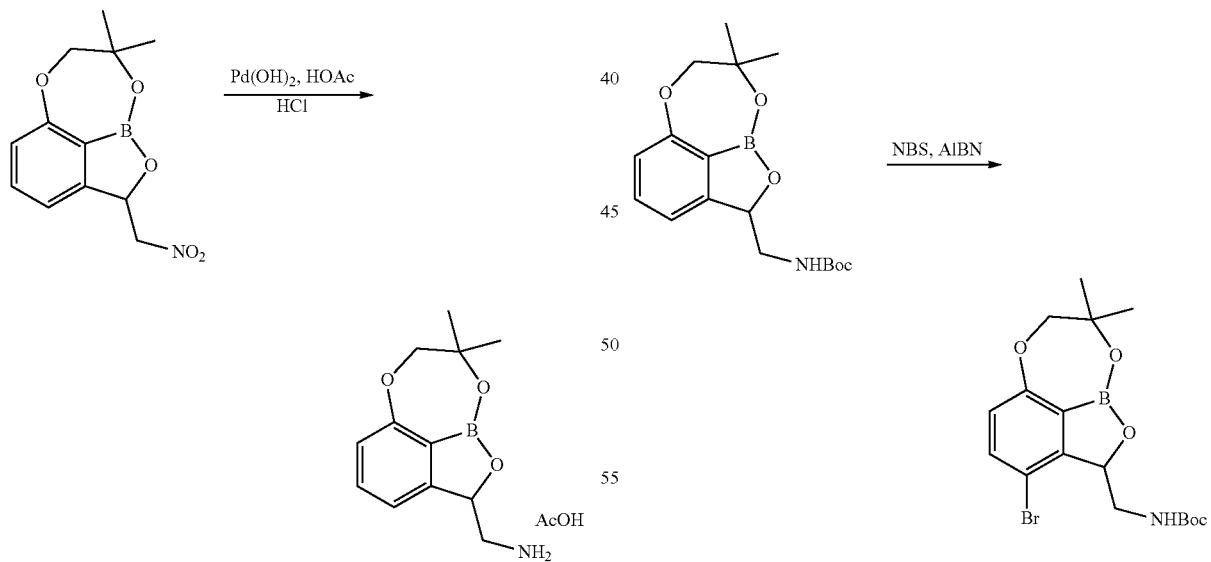

A solution of tert-butyl ((8,8-dimethyl-7,8-dihydro-2H-1,6,9-trioxa-9a-borabenzo[cd]azulen-2-yl)methyl)carbamate (232 g, 0.70 mmol), NBS (143 mg, 0.80 mmol) and AIBN (20 mg) in 30 mL of acetonitrile was stirred at reflux for 1 hour. The solvent was evaporated at 40° C. at reduced pressure and the residue was purified by silica gel chromatography eluting with a mixture of ethyl acetate and petroleum ether (1:4) to give the title compound (260 mg, 88.6%) as a solid. LC-MS: 312.0/314.0 $[M+H-100]^+$.

g) tert-butyl ((3,8,8-trimethyl-7,8-dihydro-2H-1,6,9-trioxa-9a-borabenzo[cd]azulen-2-yl)methyl)carbamate

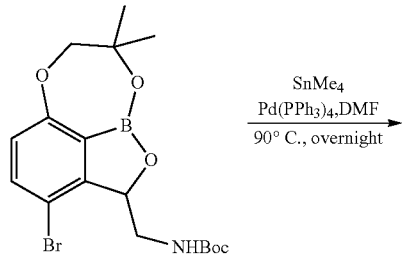

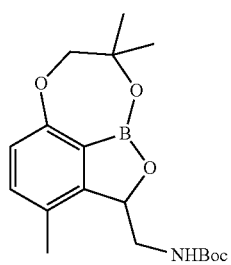

A solution of tert-butyl ((3-bromo-8,8-dimethyl-7,8-dihydro-2H-1,6,9-trioxa-9a-borabenzo[cd]azulen-2-yl)methyl)carbamate (1 eq.), tetramethylstannane (approx. 3.5-4.5 eq., approx. 3.9 eq.) and Pd(Ph$_3$)$_4$(approx. 0.01 to 0.5 eq., approx. 0.1 eq.) in DMF can be degassed with N$_2$. Then the mixture can be heated at between about 50° C. and 150° C. (about 90° C. for example) for between about 4 hours and 24 hours (about 16 hours for example). The reaction mixture can be cooled to room temperature, and then the mixture can be poured into water, can be extracted with ethyl acetate, and can be washed with water and brine. The organic layer can be dried over anhydrous sodium sulfate, filtered and concentrated in vacuo. The residue can be purified by silica gel chromatography eluting with a mixture of ethyl acetate and petroleum ether to give the title compound.

h) (3,8,8-trimethyl-7,8-dihydro-2H-1,6,9-trioxa-9a-borabenzo[cd]azulen-2-yl)methanamine hydrochloride

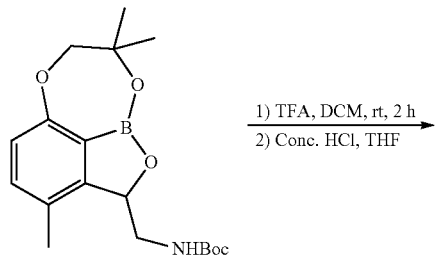

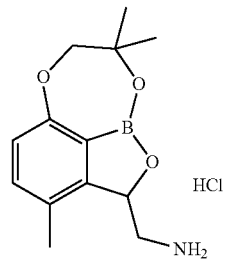

A solution of tert-butyl ((3,8,8-trimethyl-7,8-dihydro-2H-1,6,9-trioxa-9a-borabenzo[cd]azulen-2-yl)methyl)carbamate and TFA in DCM can be stirred at room temperature for 2 hours. The solvent can be evaporated at reduced pressure and the residue can be treated with 2 M HCl in ether, then can be washed with ether to give the title compound.

Example 7

(S)-(3,8,8-trimethyl-7,8-dihydro-2H-1,6,9-trioxa-9a-borabenzo[cd]azulen-2-yl)methanamine

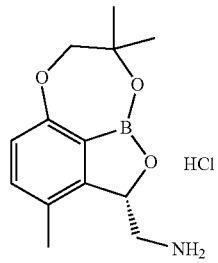 [SMILES: Cc1ccc2c3c1[C@@H](CN)OB3OC(C)(C)CO2 ; Cl]

a) (S)-tert-butyl ((3-bromo-8,8-dimethyl-7,8-dihydro-2H-1,6,9-trioxa-9a-borabenzo[cd]azulen-2-yl)methyl)carbamate

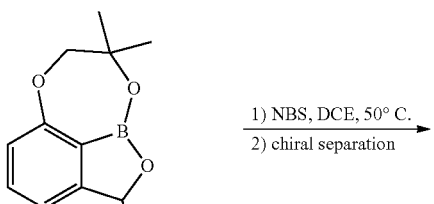

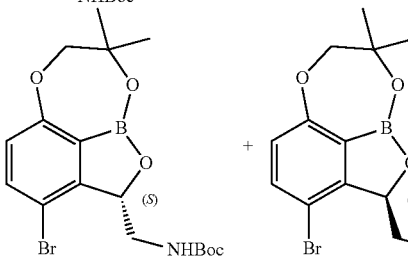

A solution of tert-butyl ((8,8-dimethyl-7,8-dihydro-2H-1,6,9-trioxa-9a-borabenzo[cd]azulen-2-yl)methyl)carbamate (5.5 g, 16.5 mmol) and NBS (3.2 g, 18.2 mmol) in 100 mL of dichloroethane was stirred at 50° C. for 18 hours. The solvent was evaporated at 40° C. under reduced pressure and the residue was purified by silica gel chromatography eluting with a mixture of ethyl acetate and petroleum ether (1:10) to give the title compound (5.9 g, 86.5%) as an oil. The racemic compound separated via SFC (chiral column CHIRALPAK AD-H, eluted with EtOH (20%) and CO$_2$ (80%)) to give 2.2 g of (S)-isomer (first eluting isomer, RT=3.0 min) and 2.2 g of (R)-isomer (second eluting isomer, RT=4.1 min). LC-MS: 312.0/314.0 [M+H-100]$^+$.

b) tert-butyl (S)-((3,8,8-trimethyl-7,8-dihydro-2H-1,6,9-trioxa-9a-borabenzo[cd]azulen-2-yl)methyl)carbamate

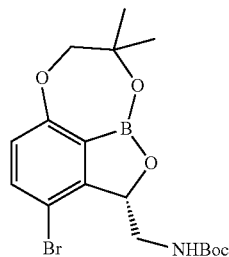

A solution of tert-butyl (S)-((3-bromo-8,8-dimethyl-7,8-dihydro-2H-1,6,9-trioxa-9a-borabenzo[cd]azulen-2-yl)methyl)carbamate (1 eq.), tetramethylstannane (approx. 3.5-4.5 eq., approx. 3.9 eq.) and Pd(Ph$_3$)$_4$ (approx. 0.01 to 0.5 eq., approx. 0.1 eq.) in DMF can be degassed with N$_2$. Then the mixture can be heated at between about 50° C. and 150° C. (about 90° C. for example) for between about 4 hours and 24 hours (about 16 hours for example). The reaction mixture can be cooled to room temperature, and then the mixture can be poured into water, can be extracted with ethyl acetate, and can be washed with water and brine. The organic layer can be dried over anhydrous sodium sulfate, filtered and concentrated in vacuo. The residue can be purified by silica gel chromatography eluting with a mixture of ethyl acetate and petroleum ether to give the title compound.

c) (S)-(3,8,8-trimethyl-7,8-dihydro-2H-1,6,9-trioxa-9a-borabenzo[cd]azulen-2-yl)methanamine hydrochloride

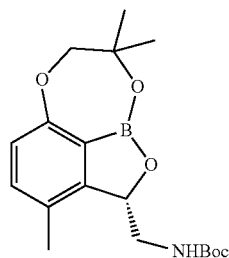

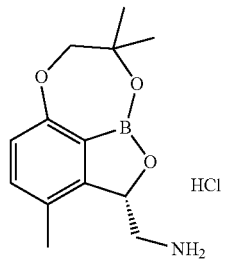

A solution of tert-butyl (S)-((3,8,8-trimethyl-7,8-dihydro-2H-1,6,9-trioxa-9a-borabenzo[cd]azulen-2-yl)methyl)carbamate and TFA in DCM can be stirred at room temperature for between about 10 minutes and 10 hours, for example, about 2 hours. The solvent can be evaporated at reduced pressure and the residue can be treated with 2 M HCl in ether, then can be washed with ether to give the title compound.

Example 8

(S)-(3-ethyl-7,8-dihydro-2H-1,6,9-trioxa-9a-borabenzo[cd]azulen-2-yl)methanamine Example 9

(S)-(3-vinyl-7,8-dihydro-2H-1,6,9-trioxa-9a-borabenzo[cd]azulen-2-yl)methanamine Example 10

(S)-(3-propyl-7,8-dihydro-2H-1,6,9-trioxa-9a-borabenzo[cd]azulen-2-yl)methanamine Example 11

(S)-(3-isopropyl-7,8-dihydro-2H-1,6,9-trioxa-9a-borabenzo[cd]azulen-2-yl)methanamine Example 12

(S)-(3-allyl-7,8-dihydro-2H-1,6,9-trioxa-9a-borabenzo[cd]azulen-2-yl)methanamine Example 13

(S)-(3-cyclopropyl-7,8-dihydro-2H-1,6,9-trioxa-9a-borabenzo[cd]azulen-2-yl)methanamine

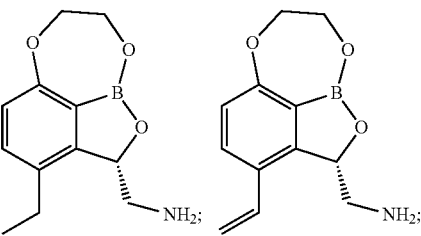

-continued

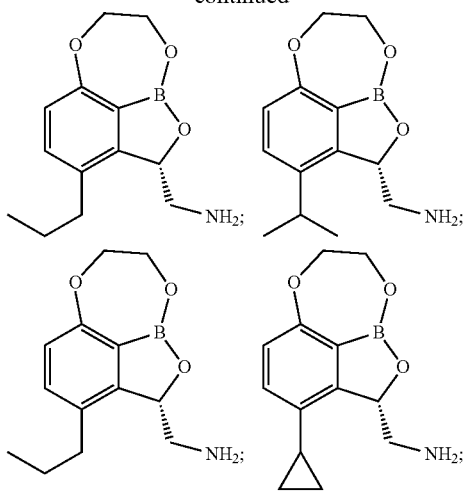

Examples 8-13 can be synthesized utilizing the process described in Example 2—(S)-(3-methyl-7,8-dihydro-2H-1,6,9-trioxa-9a-borabenzo[cd]azulen-2-yl)methanamine, substituting out the tin compound tetramethylstannane in step b) of Example 18 for the following tin compounds: Example 8—tetraethylstannane or ethyltri(n-butyl)stannane; Example 9—tetravinylstannane or vinyltri(n-butyl)stannane; Example 10—tetrapropylstannane or propyltri(n-butyl)stannane; Example 11—tetraisopropylstannane or isopropyltri(n-butyl)stannane; Example 12—tetraallylstannane or allyltri(n-butyl)stannane; and Example 13—tetracyclopropylstannane or cyclopropyltri(n-butyl)stannane.

Example 14

((2S)-3-ethyl-8-methyl-7,8-dihydro-2H-1,6,9-trioxa-9a-borabenzo[cd]azulen-2-yl)methanamine Example 15

((2S)-3-vinyl-8-methyl-7,8-dihydro-2H-1,6,9-trioxa-9a-borabenzo[cd]azulen-2-yl)methanamine Example 16

((2S)-3-propyl-8-methyl-7,8-dihydro-2H-1,6,9-trioxa-9a-borabenzo[cd]azulen-2-yl)methanamine Example 17

((2S)-3-isopropyl-8-methyl-7,8-dihydro-2H-1,6,9-trioxa-9a-borabenzo[cd]azulen-2-yl)methanamine Example 18

((2S)-3-allyl-8-methyl-7,8-dihydro-2H-1,6,9-trioxa-9a-borabenzo[cd]azulen-2-yl)methanamine Example 19

((2S)-3-cyclopropyl-8-methyl-7,8-dihydro-2H-1,6,9-trioxa-9a-borabenzo[cd]azulen-2-yl)methanamine

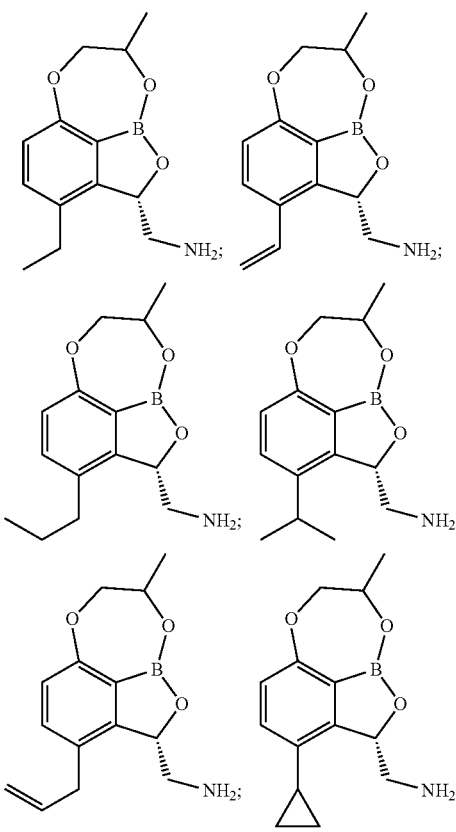

Examples 14-19 can be synthesized utilizing the process described in Example 5—((2S)-3,8-dimethyl-7,8-dihydro-2H-1,6,9-trioxa-9a-borabenzo[cd]azulen-2-yl)methanamine, substituting out the tin compound tetramethylstannane in step g) of Example 5 for the following tin compounds: Example 14—tetraethylstannane or ethyltri(n-butyl)stannane; Example 15—tetravinylstannane or vinyltri(n-butyl)stannane; Example 16—tetrapropylstannane or propyltri(n-butyl)stannane; Example 17—tetraisopropylstannane or isopropyltri(n-butyl)stannane; Example 18—tetraallylstannane or allyltri(n-butyl)stannane; and Example 19—tetracyclopropylstannane or cyclopropyltri(n-butyl)stannane.

Example 20

(S)-(3-ethyl-8,8-dimethyl-7,8-dihydro-2H-1,6,9-trioxa-9a-borabenzo[cd]azulen-2-yl)methanamine Example 21

(S)-(3-vinyl-8,8-dimethyl-7,8-dihydro-2H-1,6,9-trioxa-9a-borabenzo[cd]azulen-2-yl)methanamine

Example 22

(S)-(3-propyl-8,8-dimethyl-7,8-dihydro-2H-1,6,9-trioxa-9a-borabenzo[cd]azulen-2-yl)methanamine

Example 23

(S)-(3-isopropyl-8,8-dimethyl-7,8-dihydro-2H-1,6,9-trioxa-9a-borabenzo[cd]azulen-2-yl)methanamine

Example 24

(S)-(3-allyl-8,8-dimethyl-7,8-dihydro-2H-1,6,9-trioxa-9a-borabenzo[cd]azulen-2-yl)methanamine

Example 25

(S)-(3-cyclopropyl-8,8-dimethyl-7,8-dihydro-2H-1,6,9-trioxa-9a-borabenzo[cd]azulen-2-yl)methanamine

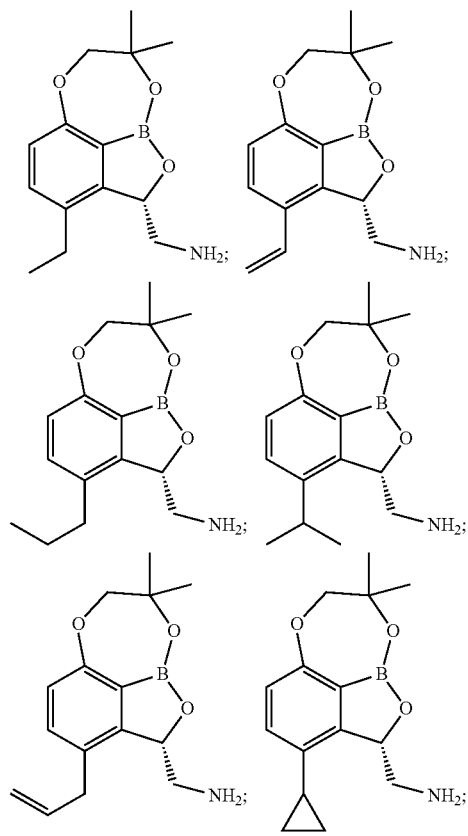

Examples 20-25 can be synthesized utilizing the process described in Example 7—(S)-(3,8,8-trimethyl-7,8-dihydro-2H-1,6,9-trioxa-9a-borabenzo[cd]azulen-2-yl)methanamine, substituting out the tin compound tetramethylstannane in step b) of Example 20 for the following tin compounds: Example 21—tetraethylstannane or ethyltri(n-butyl)stannane; Example 22—tetravinylstannane or vinyltri(n-butyl)stannane; Example 23—tetrapropylstannane or propyltri(n-butyl)stannane; Example 24—tetraisopropylstannane or isopropyltri(n-butyl)stannane; Example 25—tetraallylstannane or allyltri(n-butyl)stannane; and Example 26—tetracyclopropylstannane or cyclopropyltri(n-butyl)stannane.

Example 27

((2S,8R)-2-(aminomethyl)-3-methyl-7,8-dihydro-2H-1,6,9-trioxa-9a-borabenzo[cd]azulen-8-yl)methanol

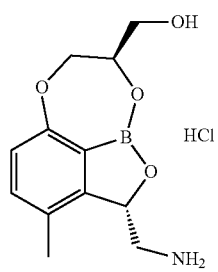 [SMILES: Cc1ccc2c3c1[C@@H](CN)OB3O[C@H](CO)CO2 ; Cl]

a) (S)-5-((2,2-dimethyl-1,3-dioxolan-4-yl)methoxy)-2-methylbenzaldehyde

A solution of 5-hydroxy-2-methylbenzaldehyde (1 eq. 13.6 mmol), (R)-(2,2-dimethyl-1,3-dioxolan-4-yl)methyl 4-methylbenzenesulfonate (approx. 1.1 eq.) and $K_2CO_3$ (approx. 1.25 eq.) in DMSO can be stirred at between about 50° C. and 150° C. (about 70° C. for example) for between about 4 hours and 24 hours (about 16 hours for example). Then the mixture can be poured into water, can be extracted with ethyl acetate, can be washed with water and brine, and can be dried over anhydrous sodium sulfate. The solvent can be evaporated under reduced pressure and the residue can be purified by silica gel chromatography eluting with ethyl acetate and petroleum ether to afford the product.

b) (S)-1-(5-(((S)-2,2-dimethyl-1,3-dioxolan-4-yl)methoxy)-2-methylphenyl)-2-nitroethan-1-ol

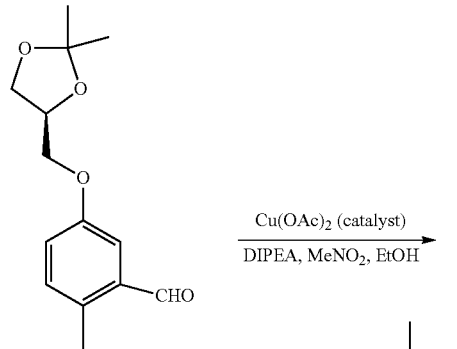

A mixture of copper (II) acetate (1 eq.), (1R)-1,7,7-trimethyl-N-(pyridin-2-ylmethyl)bicyclo[2.2.1]heptan-2-amine (1.1 eq.) in ethanol can be stirred at r.t. for approx. 1 h, then a solution of (S)-5-((2,2-dimethyl-1,3-dioxolan-4-yl)methoxy)-2-methylbenzaldehyde (10 eq.) in ethanol can be added. The reaction mixture can be cooled to between about −35° C. to about −40° C., and then nitromethane (100 eq.) was added dropwise, maintaining the temperature below about −35° C., followed by the addition of diisopropylethylamine (2.2 eq.). The reaction can be stirred at −35° C. for 24 h, and then can be quenched with trifluoroacetic acid (2.2 eq.). EtOAc can be added to the resulting solution. The separated organic phase can be washed with water and then concentrated under vacuum. The residue can be purified by silica gel chromatography eluting with ethyl acetate and petroleum ether to afford the product.

c) (S)-2-amino-1-(5-(((S)-2,2-dimethyl-1,3-dioxolan-4-yl)methoxy)-2-methylphenyl)ethan-1-ol

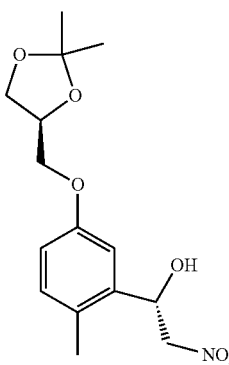

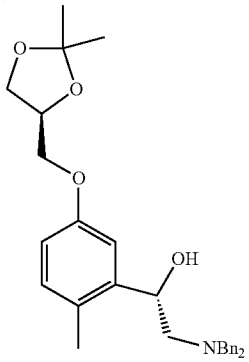

A solution of (S)-1-(5-(((S)-2,2-dimethyl-1,3-dioxolan-4-yl)methoxy)-2-methylphenyl)-2-nitroethan-1-ol and Pd/C in methanol can be hydrogenated under 1 atm of H₂ at room temperature for about 48 h. Then it can be filtered through a bed of Celite and the filtrate can be concentrated under reduced pressure to afford the crude product. It can be used directly in the next step without further purification.

d) (S)-2-(dibenzylamino)-1-(5-(((S)-2,2-dimethyl-1,3-dioxolan-4-yl)methoxy)-2-methylphenyl)ethan-1-ol

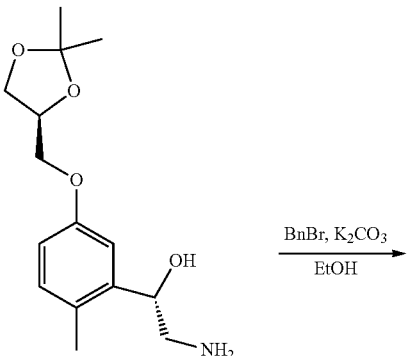

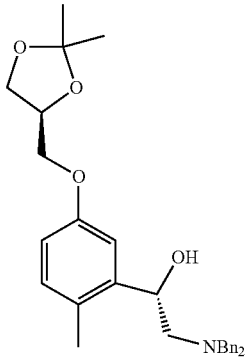

To a stirred solution of (S)-2-amino-1-(5-(((S)-2,2-dimethyl-1,3-dioxolan-4-yl)methoxy)-2-methylphenyl)ethan-1-ol (1 eq.) in EtOH can be added K₂CO₃ (2 eq.) and BnBr (2 eq.). The reaction mixture can be stirred overnight at room temperature. The solvent can be removed under reduced pressure and the residue can be purified by silica gel chromatography eluting with ethyl acetate and petroleum ether to afford the product.

e) (S)-3-((dibenzylamino)methyl)-7-(((S)-2,2-dimethyl-1,3-dioxolan-4-yl)methoxy)-4-methylbenzo[c][1,2]oxaborol-1(3H)-ol

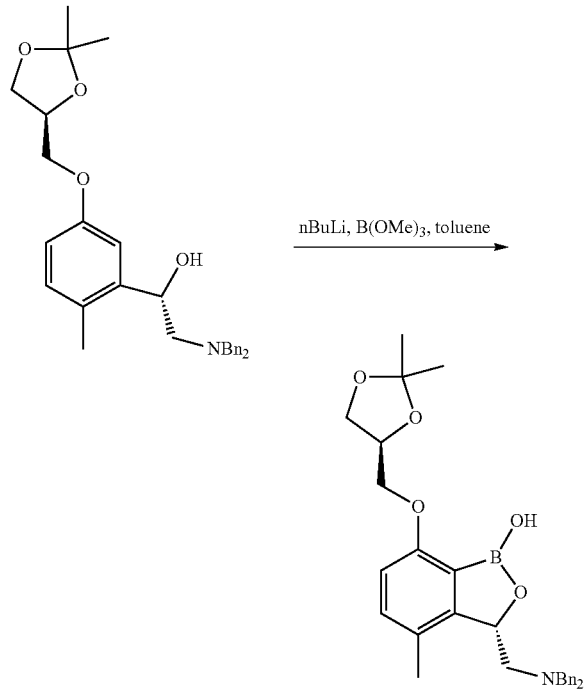

To a solution of (S)-2-(dibenzylamino)-1-(5-(((S)-2,2-dimethyl-1,3-dioxolan-4-yl)methoxy)-2-methylphenyl)ethan-1-ol (1 eq.) in dry toluene at about −30° C. under N₂ atmosphere can be added n-BuLi (2.5 M in hexane, 7 eq.) dropwise over about 30 minutes. After addition, the mixture can be stirred at about 0° C. for another about 2 h, and then cooled to about −70° C.; trimethyl borate can be added dropwise keeping the temperature below about −50° C. After addition, the reaction mixture can be allowed to warm to about −40° C. for about 3 h and then warmed to r.t. and stirred overnight. The reaction can be quenched with 5% aqueous NaHCO₃ and stirred vigorously for about 15 min, the resulting suspension can be filtered and the filtrate can be separated. The organic layer can be washed with water and can be concentrated in vacuum to afford the crude product.

f) Title Compound

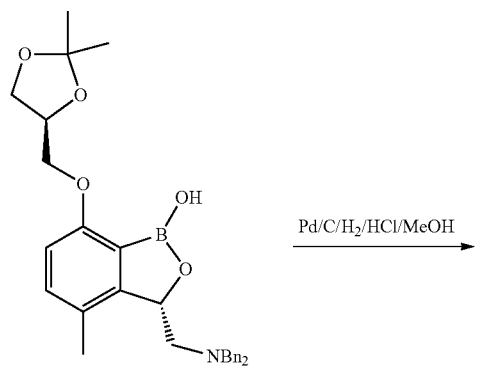

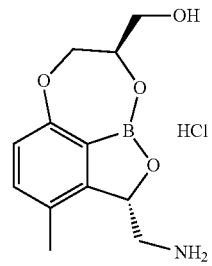

A solution of (S)-3-((dibenzylamino)methyl)-7-(((S)-2,2-dimethyl-1,3-dioxolan-4-yl)methoxy)-4-methylbenzo[c][1,2]oxaborol-1(3H)-ol (1 eq.) and Pd/C (10%) in methanol with 2 mL of conc HCl can be hydrogenated under 1 atm of H₂ at room temperature for about 48 h. Then it can be filtered through a bed of Celite and the filtrate can be concentrated at reduced pressure to give an oil. The crude product can be purified by preparative-HPLC using Daisogel 10μ C18 column (250×50 mm) and can be eluted with a gradient of water/acetonitrile (0.05% TFA). The collected fraction can be concentrated under reduced pressure. The residue can be dissolved in ether and sat. HCl (g) in ether and the mixture can be stirred at room temperature for about 1 h. The solid can be collected by filtration and washed with ether to give the title compound.

Example 28

((2S,8R)-2-(aminomethyl)-3,8-dimethyl-7,8-dihydro-2H-1,6,9-trioxa-9a-borabenzo[cd]azulen-8-yl)methanol Example 29

((2S,8S)-2-(aminomethyl)-3,8-dimethyl-7,8-dihydro-2H-1,6,9-trioxa-9a-borabenzo[cd]azulen-8-yl)methanol

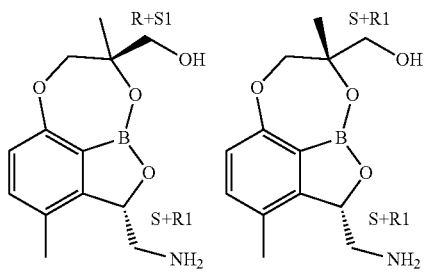 [SMILES: Cc1ccc2c3c1[C@@H](CN)OB3O[C@](C)(CO)CO2 ; Cc1ccc2c3c1[C@@H](CN)OB3O[C@@](C)(CO)CO2]

a) ((2-methylallyloxy)methyl)benzene

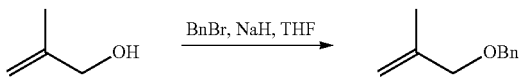

A solution of methallyl alcohol (80 g, 1.1 mol) in THF (100 mL) was added dropwise to a suspension of NaH (66 g, 1.65 mol) in THF (800 mL) at 25° C. under argon. After 1 h, a solution of benzyl bromide (207 g, 1.2 mol) in THF (100 mL) was added slowly and the reaction mixture was stirred at room temperature for 12 h. The reaction mixture was quenched with saturated NH₄Cl solution (200 mL) and extracted with ethyl acetate (3×200 mL). The combined organic layers were washed with water (100 mL) and brine (100 mL), dried over Na₂SO₄. The solvent was removed under reduced pressure. The residue was distilled to afford the desired product (134 g, 74%) as colorless oil. $^1$H NMR (400 MHz, CDCl₃): δ 7.40-7.29 (m, 5H), 5.05 (s, 1H), 4.97 (s, 1H), 4.54 (s, 2H), 3.98 (s, 2H), 1.82 (s, 3H).

b) (2-(benzyloxymethyl)-2-methyloxirane

((2-methylallyloxy)methyl)benzene (41.5 g, 256 mmol) was dissolved in DCM (1200 mL) and cooled to 0° C. m-CPBA (69.7 g, 384 mmol) was added and the mixture was stirred overnight at room temperature for 12 h. After the white precipitate was filtered off, the filtrate was washed with saturated Na₂CO₃ solution (200 mL), H₂O (200 mL), and brine. After the solvent was removed under reduced pressure, the crude reside was purified by silica gel chromatography eluting with ethyl acetate and petroleum ether (1:20) to afford the pure product (20 g, 44%) as colorless oil. $^1$H NMR (400 MHz, CDCl₃): δ 7.40-7.29 (m, 5H), 4.60 (q, J=12.0 Hz, 2H), 3.61 (d, J=11.0 Hz, 1H), 3.48 (d, J=11.0 Hz, 1H), 2.78 (d, J=4.9 Hz, 1H), 2.66 (d, J=4.9 Hz, 1H), 1.43 (s, 3H).

c) 3-(3-(benzyloxy)-2-hydroxy-2-methylpropoxy)-2-bromobenzaldehyde

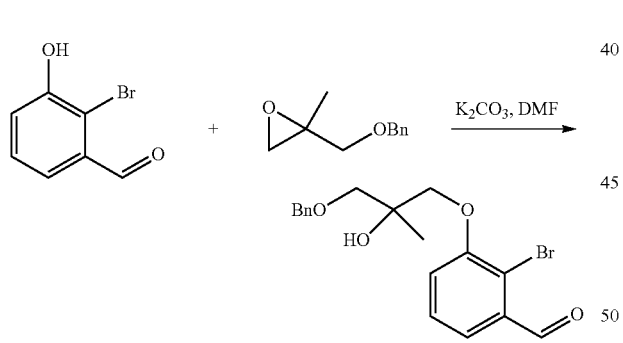

To a solution of (2-(benzyloxymethyl)-2-methyloxirane (26 g, 145.9 mmol) in DMF (700 mL) was added K₂CO₃ (42 g, 304.3 mmol), followed by 2-bromo-3-hydroxybenzaldehyde (30 g, 149.3 mmol). The suspension was stirred at 90° C. for 6 h. The mixture was cooled down to room temperature, diluted with brine and extracted with ethyl acetate (200 mL×3). The organic solvent was removed under vacuum and the residue was purified by silica gel chromatography eluting with ethyl acetate and petroleum ether (1:20) to afford the pure product (27 g, 49%) as light yellow oil. $^1$H NMR (400 MHz, DMSO-d₆): δ 10.29 (s, 1H), 7.512-7.41 (m, 3H), 7.31-7.23 (m, 5H), 4.91 (s, 1H), 4.53 (dd, $J_1$=12.4 Hz, $J_2$=17.2 Hz, 2H), 4.06 (d, J=9.2 Hz, 1H), 3.91 (d, J=9.2 Hz, 1H), 3.54 (d, J=9.3 Hz, 1H), 3.47 (d, J=9.3 Hz, 1H), 1.27 (s, 3H).

d) 3-(3-(benzyloxy)-2-hydroxy-2-methylpropoxy)-2-(4,4,5,5-tetramethyl-1,3,2-dioxaborolan-2-yl)benzaldehyde

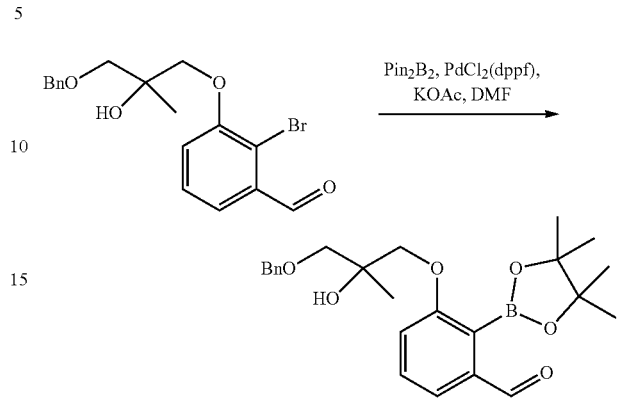

A solution of 3-(3-(benzyloxy)-2-hydroxy-2-methylpropoxy)-2-bromobenzaldehyde (21.3 g, 56.2 mmol), Pin₂B₂ (28.6 g, 112.4 mmol), KOAc (6.1 g, 61.9 mmol), PdCl₂(dppf) DCM (1.23 g, 1.7 mmol) in DMF (150 mL) was degassed for 3 times with nitrogen. The mixture was heated at 90° C. for 16 h. After the reaction was worked up with ethyl acetate and brine, the residue was purified by silica gel chromatography eluting with ethyl acetate and petroleum ether (1:20) to afford the desired product (15.3 g, 64%) as light yellow oil. LC-MS: 367.1 [344+Na]⁺ e) (3-(benzyloxy)-2-hydroxy-2-methylpropoxy)-3-(nitromethyl)benzo[c][1,2]oxaborol-1(3H)-ol

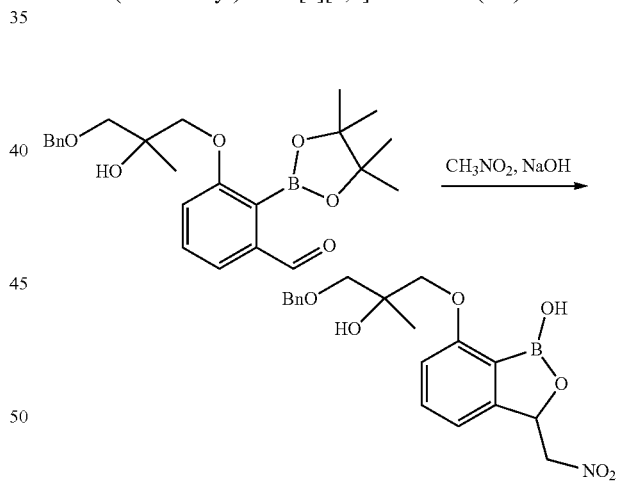

To an ice-cold solution of 3-(3-(benzyloxy)-2-hydroxy-2-methylpropoxy)-2-(4,4,5,5-tetramethyl-1,3,2-dioxaborolan-2-yl)benzaldehyde (18.8 g, 44.1 mmol) in THF was added a solution of NaOH (1.76 g, 44.1 mmol) in water (100 mL). After stirring for 15 min, CH₃NO₂ (3.3 g, 53 mmol) was added and the mixture was stirred at room temperature for 15 h. The reaction solution was acidified with AcOH to pH 3-5. The suspension was extracted with ethyl acetate (50 mL×3). The combined organic layer was evaporated under vacuum, and the residue was purified by silica gel chromatography eluting with ethyl acetate and petroleum ether (1:10) to afford the pure product (6.8 g, 40%) as colorless oil. LC-MS: 386.0 [M-1]⁻ f) (2-(aminomethyl)-8-methyl-7,8-dihydro-2H-1,6,9-trioxa-9a-borabenzo[cd]azulen-8-yl)methanol acetate

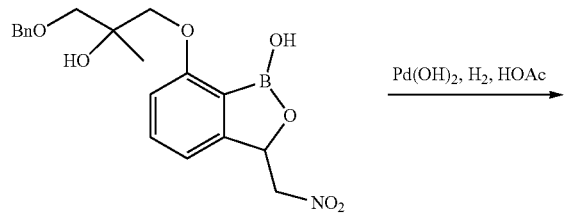

Pd(OH)$_2$/C (200 mg) was added to a solution of 7-(3-(benzyloxy)-2-hydroxy-2-methylpropoxy)-3-(nitromethyl)benzo[c][1,2]oxaborol-1(3H)-ol (1 g, crude) in AcOH (20 mL). The solution was degassed 3 times with H$_2$, and stirred at room temperature for 12 h. The reaction mixture was filtered through Celite, and the filtrate was concentrated under vacuum to afford the crude product (1 g, crude) as yellow solid.

g) tert-butyl ((8-(hydroxymethyl)-8-methyl-7,8-dihydro-2H-1,6,9-trioxa-9a-borabenzo[cd]azulen-2-yl)methyl)carbamate

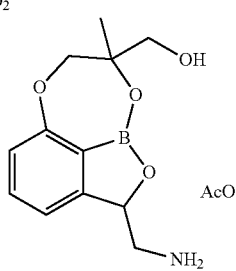

NaHCO$_3$ (437 mg, 5.2 mmol) was added to a solution of (2-(aminomethyl)-8-methyl-7,8-dihydro-2H-1,6,9-trioxa-9a-borabenzo[cd]azulen-8-yl)methanol acetate (650 mg, 2.1 mmol) in t-BuOH (10 mL) and H$_2$O (10 mL) at room temperature. After stirring for 15 min, (Boc)$_2$O (854 mg, 3.9 mmol) was added and the reaction mixture was stirred at room temperature for 2 h. The mixture was acidified with AcOH to pH 6-7 and extracted with DCM (30 mL×3). Combined organic layers were evaporated under vacuum, and the residue was purified by silica gel chromatography eluting with ethyl acetate and petroleum ether (1:3) to afford the desired product (400 mg, 55%) as courses oil. LC-MS: 294.1 [M-55]$^+$ h) tert-butyl ((3-bromo-8-(hydroxymethyl)-8-methyl-7,8-dihydro-2H-1,6,9-trioxa-9a-borabenzo[cd]azulen-2-yl)methyl)carbamate

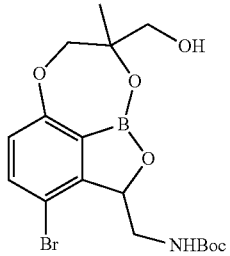

To a solution of tert-butyl ((8-(hydroxymethyl)-8-methyl-7,8-dihydro-2H-1,6,9-trioxa-9a-borabenzo[cd]azulen-2-yl)methyl)carbamate (200 mg, 0.57 mmol) in ACN (10 mL) was added NBS (102 mg, 0.57 mmol), and the solution was stirred at 90° C. for 1 h. The reaction was quenched with NH$_4$Cl solution, extracted with ethyl acetate (20 mL×3). The organic lay was washed with brine, dried over Na$_2$SO$_4$, concentrated in vacuum. The crude residue was purified by silica gel chromatography eluting with ethyl acetate and petroleum ether (1:3) to afford the product (230 mg, crude) as pale solid. LC-MS: 328.1 [M-Boc+H]$^+$.

i) tert-butyl ((8-(hydroxymethyl)-3,8-dimethyl-7,8-dihydro-2H-1,6,9-trioxa-9a-borabenzo[cd]azulen-2-yl)methyl)carbamate

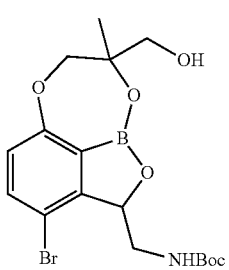

-continued

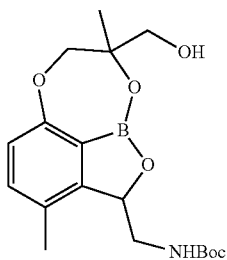

A solution of tert-butyl ((3-bromo-8,8-dimethyl-7,8-dihydro-2H-1,6,9-trioxa-9a-borabenzo[cd]azulen-2-yl)methyl)carbamate (1 eq.), tetramethylstannane (approx. 3.5-4.5 eq., approx. 3.9 eq.) and Pd(Ph$_3$)$_4$(approx. 0.01 to 0.5 eq., approx. 0.1 eq.) in DMF can be degassed with N$_2$. Then the mixture can be heated at between about 50° C. and 150° C. (about 90° C. for example) for between about 4 hours and 24 hours (about 16 hours for example). The reaction mixture can be cooled to room temperature, and then the mixture can be poured into water, can be extracted with ethyl acetate, and can be washed with water and brine. The organic layer can be dried over anhydrous sodium sulfate, filtered and concentrated in vacuo. The residue can be purified by silica gel chromatography eluting with a mixture of ethyl acetate and petroleum ether to give the title compound.

j) Title Compounds

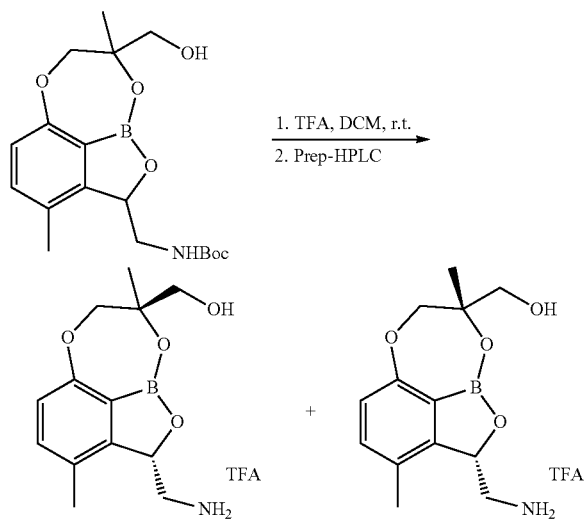

tert-butyl ((3,8,8-trimethyl-7,8-dihydro-2H-1,6,9-trioxa-9a-borabenzo[cd]azulen-2-yl)methyl)carbamate (crude) can be dissolved in a solution of TFA in DCM (approximately 1:2 to about 1:20; 1:10 for example. The solution can be stirred at room temperature for between about 10 minutes and 10 hours, 1 hour for example, and then can be concentrated in vacuum. The crude product can be purified by preparative-HPLC using Daisogel 10µ C18 column and can be eluted with a gradient of water/acetonitrile (0.05% TFA). The collected fraction can be concentrated under reduced pressure to afford the title compounds.

In Vitro Assays

Example 30

MIC Determination Against Mycobacteria

The measurement of the Minimum Inhibitory Concentration (MIC) against *M. tuberculosis* strains for each tested compound was performed in 96-well flat-bottom, polystyrene microtiter plates in a final volume of 100 uL. Ten two-fold drug dilutions in neat DMSO starting at 50 mM were performed. Drug solutions were added to Middlebrook 7H9 medium (Difco) and isoniazid (INH) (Sigma Aldrich) was used as a positive control with 2-fold dilutions of INH starting at 160 ug/mL. The inoculum was standardized to approximately 1×10$^7$ cfu/ml and diluted 1 in 100 in Middlebrook 7H9 broth (Difco). This inoculum (100 uL) was added to the entire plate but G-12 and H-12 wells were used as blank controls. All plates were placed in a sealed box to prevent drying out of the peripheral wells and incubated at 37° C. without shaking for six days. A Resazurin solution was prepared by dissolving one tablet of Resazurin (Resazurin Tablets for Milk Testing; Ref 330884Y' VWR International Ltd) in 30 mL of sterile PBS (phosphate buffered saline). Of this solution, 25 uL were added to each well. Fluorescence was measured (Spectramax M5 Molecular Devices, Excitation 530 nm, Emission 590 nm) after 48 hours to determine the MIC value.

Example 31

General Antimicrobial Activity Assay

Whole-cell antimicrobial activity was determined by broth microdilution using the Clinical and Laboratory Standards Institute (CLSI) recommended procedure, Document M7-A7, "Methods for Dilution Susceptibility Tests for Bacteria that Grow Aerobically".

Table 1 provides MIC values against bacterial strains K12; *E. coli* K12 tolC/Tn10; *A. baumannii* ATCC 17978; and *P. aeruginosa* PA01 for comparator compounds (C1-C15) shown in Table 4 and for G26-CH$_3$. As can be seen in Table 1, the comparator compounds do not generally possess significant activity across several pathogenic Gram negative bacteria, as well as an efflux pump deficient *E. coli*. Similarly, compound G26-CH$_3$ (Example 2) has poor activity against these Gram negative bacteria.

TABLE 1 provides MIC Values Against non-Mycobacterial strains for substituted benzoxaborole compounds

| Compound | MIC: *E. coli* K12 [ug/mL] | MIC: *E. coli* K12 tolC::Tn10 [ug/mL] | MIC: *A. baumannii* ATCC 17978 [ug/mL] | MIC: *P. aeruginosa* PA01 [ug/mL] | MIC: *S. pneumoniae* ATCC 6301 | MIC *S. aureus* ATCC 29213 |
|---|---|---|---|---|---|---|
| Example 2 G26-CH$_3$ | >64 | >64 | >64 | >64 | >64 | >64 |
| C1-H | — | — | — | — | | |
| C2-H | 2 | 4 | 2 | 2 | | |
| C3-H | — | — | — | — | | |

TABLE 1-continued provides MIC Values Against non-Mycobacterial strains for substituted benzoxaborole compounds

| Compound | MIC: E. coli K12 [ug/mL] | MIC: E. coli K12 tolC::Tn10 [ug/mL] | MIC: A. baumannii ATCC 17978 [ug/mL] | MIC: P. aeruginosa PA01 [ug/mL] | MIC: S. pneumoniae ATCC 6301 | MIC S. aureus ATCC 29213 |
|---|---|---|---|---|---|---|
| C4-Br | 64 | 64 | 64 | 64 | | |
| C5-H | — | — | — | — | | |
| C6-Cl | 64 | 64 | 64 | 64 | | |
| C7-Cl2 | — | — | — | — | | |
| C8-Cl | — | — | — | — | | |
| C9-Cl | — | — | — | — | | |
| C10-H | — | — | — | — | | |
| C11-H | 2 | 2 | 4 | 2 | | |
| C12-H | 4 | 2 | 4 | 16 | | |
| C13-Cl | — | — | — | — | | |
| C14-Cl2 | — | — | — | — | | |
| C15-F | — | — | — | — | | |

Example 32

LeuRS Expression and Purification

For biochemical analyses an N-terminal six histidine-tagged LeuRS was over-expressed in *Escherichia coli* which were *E. coli* codon-optimised (GenScript, Piscataway N.J., USA), from human mitochondria and cytoplasm, and *M. tuberculosis*. N-terminal six histidine-tagged LeuRS proteins were over-expressed and purified according to Novagen (Madison, Wis., USA) using an *E. coli* BL21(DE3) T7 RNA polymerase over-expression strain.

Example 34

Aminoacylation Assay

Experiments were performed in 96-well microtiter plates, using 80 μL reaction mixtures containing 50 mM HEPES-KOH (pH 8.0), 30 mM $MgCl_2$ 30 mM KCl, 13 μM L-[$^{14}$C] leucine (306 mCi/mmol, Perkin-Elmer), 15 uM total *E. coli* tRNA (Roche, Switzerland), 0.02% (w/v) BSA, 1 mM DTT, 0.2 μM LeuRS and 4 mM ATP at 30° C. Reactions were started by the addition of 4 mM ATP. After 7 minutes, reactions were quenched and tRNA was precipitated by the addition of 50 μL of 10% (w/v) TCA and transferred to 96-well nitrocellulose membrane filter plates (Millipore Multiscreen HTS, MSHAN4B50). Each well was then washed three times with 100 μL of 5% TCA. Filter plates were then dried under a heat lamp and the precipitated L-[$^{14}$C]leucine tRNALeu were quantified by liquid scintillation counting using a Wallac MicroBeta Trilux model 1450 liquid scintillation counter (PerkinElmer, Waltham, Mass., USA). The only difference was with the human cytoplasmic LeuRS when we used tRNA isolated from Brewer's Yeast (Roche Diagnostics GmbH).

Example 35

$IC_{50}$ Determination

To determine the inhibitor concentration, which reduces enzyme activity by 50% ($IC_{50}$), increasing concentrations of compound (Anacor Pharmaceuticals Inc., Palo Alto, Calif., USA) were incubated with LeuRS enzyme, tRNA and L-leucine 20 minutes. Reactions were initiated by the addition of 4 mM ATP. Reactions were stopped after 7 minutes then precipitated and counted to quantify radioactivity. IC50 values were determined using the Graphpad Prism software package (Graphpad Software Inc. (La Jolla, Calif., USA).

Example 36

HepG2 Cytotoxicity Assay

HepG2 cells (HB-8065) were fed fresh medium (Essential Minimum Eagle Medium, EMEM, supplemented with 5% fetal calf serum and 2 mM L-glutamine) the day before subculturing the plates. On the day of plate seeding, a cell suspension of 100,000 cells/mL in culture medium was prepared. Cell suspension (100 uL) was added in each well of a black 96-well microplate with clear bottom, collagen coated, (Becton Dickinson) except in column 11, that was dispensed only 100 uL of culture medium. The plates were incubated for 24 h. It was made up a range of 10 doses of test substances by preparing serial dilutions 1:2 from the stock solution in 100% DMSO and made a dilution of 1:200 of each dose in medium, to achieve a final concentration of 0.5% of DMSO. After 24 h, culture medium was removed from the plate and 150 uL of test compound dilutions were added in two replicates and 150 uL of 0.5% DMSO in culture medium to columns 11 and 12 (blank control). Plates were incubated for 48 and at 37° C., 5% CO2, 95% relative humidity. The medium was then removed and 200 uL of fresh culture medium was added and 50 uL of Resazurin solution to each well and incubated for 1 h and a half. Plates were removed from incubator to allow the fluorescence to stabilise at room temperature protected from light for 15 min. For read out of viability of cells we used Resazurine (BDH). Resazurin is used as an oxidation-reduction indicator that yields a colorimetric change and a fluorescent signal in response to metabolic activity. As cell grows, metabolic activity results in a chemical reduction of Resazurin indicated by a change from non-fluorescent blue to the reduced fluorescent pink form. The degree of Resazurin fluorescence is therefore, an indicator of the number of viable cells in the culture system. Fluorescence was measured at an excitation wavelength of 515 nm and an emission wavelength of 590 nm in a Microplate reader 1420 Multilabel HTS counter, Victor 2, (Wallac).

The fluorescence value of each well is corrected by subtracting the background value (average of column 11) from the absolute value. The percentages of inhibition are calculated relatively to the DMSO control wells (average of column 12). For each compound, the average value of the duplicate samples is calculated and the curve is fitted to Sigmoidal dose-response (variable slope) nonlinear regression curve adjustment (GraphPad) in order to calculate the IC50 (Tox50).

Example 37

The Effect of Compounds Described Herein Against *Mycobacterium tuberculosis*

Substituted benzoxaborole comparator C1-C14 were tested for antibacterial activity against a *Mycobacterium tuberculosis* species and also tested for human liver cell toxicity using HepG2 cells. Exemplary compound G26-CH$_3$ of the invention was compared to comparator compounds C1-H through C14-Br, as shown in Tables 2 as compared to Table 3.

TABLE 2 provides LeuRS inhibition IC50 values, MIC values against the *M. tuberculosis* standard strain Mtb H37Rv, toxicity values against human HepG2 cells, and selectivity values for certain substituted benzoxaboroles

| Compound Designation | Compound Structure | Mtb LeuRS IC$_{50}$ (uM) | Human cyto LeuRS IC$_{50}$ (μM) | Human mito LeuRS IC$_{50}$ (μM) | Mtb H37Rv MIC (μM) (B) | HepG2 cell 48 h Tox50 (μM) (A) | Selectivity Index (A/B) |
|---|---|---|---|---|---|---|---|
| C1-H | 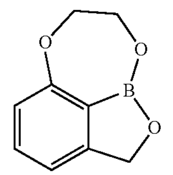 [SMILES: c1cc2c3c(c1)OCCOB3OC2] | 12.2 | 101 | — | 31 | — | — |
| C2-H (racemic) | 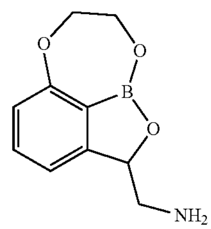 [SMILES: NCC1OB2OCCOc3cccc1c32] | 0.506 | 272 | >300 | 1.88 | >50 | >26 |
| C3-H | 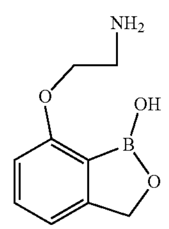 [SMILES: NCCOc1cccc2c1B(O)OC2] | 17.6 | 35.7 | — | 62 | >50 | >0.8 |
| C4-Br | 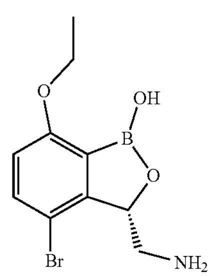 | 0.07 | 31, (73, 67) | >300 | 0.1 | 32 | 320 |
| C5-H | 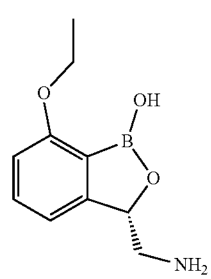 | 0.111 | 25.6 | >300 | 0.6 | 1.8 | 3 |

TABLE 2-continued provides LeuRS inhibition IC50 values, MIC values against the *M. tuberculosis* standard strain Mtb H37Rv, toxicity values against human HepG2 cells, and selectivity values for certain substituted benzoxaboroles

| Compound Designation | Compound Structure | Mtb LeuRS IC$_{50}$ (uM) | Human cyto LeuRS IC$_{50}$ (μM) | Human mito LeuRS IC$_{50}$ (μM) | Mtb H37Rv MIC (μM) (B) | HepG2 cell 48 h Tox50 (μM) (A) | Selectivity Index (A/B) |
|---|---|---|---|---|---|---|---|
| C6-Cl | 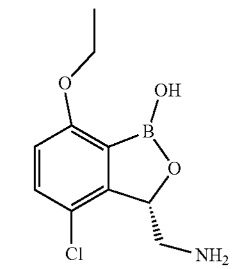 [SMILES: CCOc1ccc(Cl)c2c1B(O)O[C@@H]2CN] | 0.05 | 38.8 | >300 | 0.1 | 36.3 | 363 |
| C7-Cl$_2$ | 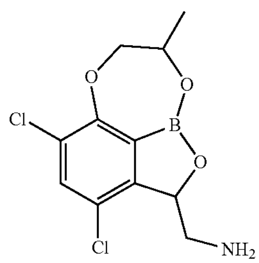 [SMILES: CC1COc2c(Cl)cc(Cl)c3c2B(O1)OC3CN] | 7.97 | — | — | 2.5 | >50 | >20 |
| C8-Cl | 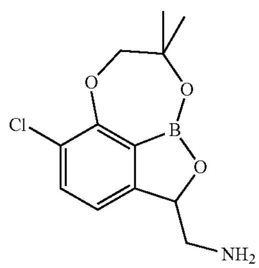 [SMILES: CC1(C)COc2c(Cl)ccc3c2B(OC3CN)O1] | 6.05 | — | — | >5.0 | >50 | 10 |
| C9-Cl | 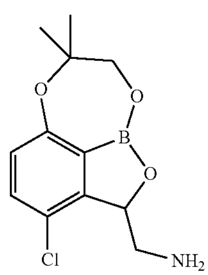 [SMILES: CC1(C)COB2OC(CN)c3c(Cl)ccc(c32)O1] | 37.59 | — | — | 5.0 | >50 | >10 |
| C10-H | 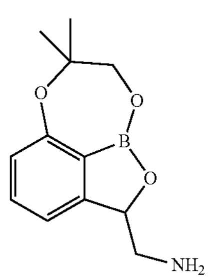 [SMILES: CC1(C)COB2OC(CN)c3cccc(c32)O1] | >300 | — | — | >5.0 | >50 | 10 |

TABLE 2-continued provides LeuRS inhibition IC50 values, MIC values against the *M. tuberculosis* standard strain Mtb H37Rv, toxicity values against human HepG2 cells, and selectivity values for certain substituted benzoxaboroles

| Compound Designation | Compound Structure | Mtb LeuRS IC$_{50}$ (uM) | Human cyto LeuRS IC$_{50}$ (μM) | Human mito LeuRS IC$_{50}$ (μM) | Mtb H37Rv MIC (μM) (B) | HepG2 cell 48 h Tox50 (μM) (A) | Selectivity Index (A/B) |
|---|---|---|---|---|---|---|---|
| C11-H | 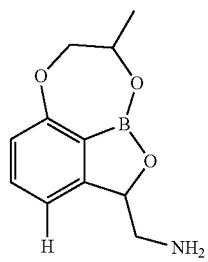 [SMILES: CC1COc2cccc3c2B(O1)OC3CN] | 0.51 | — | — | 1.56 | >50 (40%) | >32 |
| C12-H | 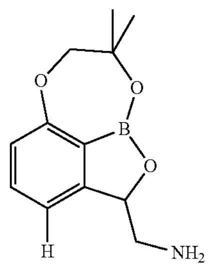 [SMILES: CC1(C)COc2cccc3c2B(OC3CN)O1] | 1.33 | — | — | >5.0 | 24.5 | >4.9 |
| C13-Cl | 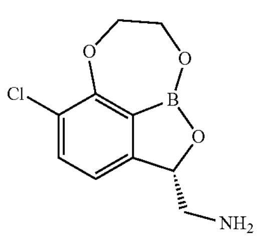 [SMILES: NC[C@H]1OB2OCCOc3c(Cl)ccc1c32] | 2.16 | | | 5.0 | >50 | >10 |
| C14-Cl$_2$ | 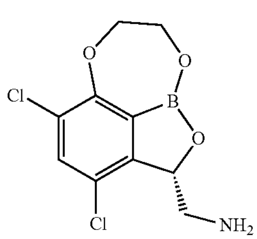 | 4.67 | | | >5.0 | >50 | >10 |

Table 3 provides LeuRS inhibition IC50 values, MIC values against the *M. tuberculosis* standard strain Mtb H27Rv, toxicity values against human HepG2 cells, and selectivity values for certain exemplified compounds of the invention.

$IC_{50}$ value for G26-$CH_3$ against *M. tuberculosis* were found to be sub-micromolar, at 0.53 micromolar. The selectivity index (SI) of Example 2 G26-$CH_3$ against *M. tuberculosis* is unexpectedly improved over other substituted benzoxaboroles in Table 2. Example 2 G26-$CH_3$, which is a substi-

TABLE 3

| Compound Designation | Compound Structure | Mtb LeuRS $IC_{50}$ (uM) | Human cyto LeuRS $IC_{50}$ (μM) | Mtb H37Rv MIC (μM) (B) | HepG2 cell 48 h Tox50 (μM) (A) | Selectivity Index (A/B) | Cell Prot Syn $IC_{50}$ (μM) |
|---|---|---|---|---|---|---|---|
| EXAMPLE 2 G26-$CH_3$ | (structure) | 0.53 | 171 | 0.2 | 971 | 4853 | >600 |
| EXAMPLE 3 G27-phenyl | (structure) | 12.0 | | 8.75 | | | |
| EXAMPLE 4 G28-thienyl | (structure) | 300 | | 40.1 | | | |

As can be seen in Table 3 for Examples 2, (G26-$CH_3$) a huge increase selectivity was observed for G26-$CH_3$ in inhibiting growth of *M. tuberculosis* versus toxicity for human HepG2 cells compared to comparator compounds.

Tables 2 and 3 show a comparison of certain substituted benzoxaborole comparator compounds (shown in closed form) with and without halogen or alkyl substitution at various positions on the benzoxaborole ring, certain substituted benzoxaboroles (shown in closed form) with and without halogen or alkyl substitution at position 4 of the benzoxaborole ring structure, and certain other substituted benzoxaoborole compounds. From the Mtb H37Rv MIC values (B), and the HepG2 cell 48 h $Tox_{50}$ values (A), it is possible to determine selectivity for inhibition of *M. tuberculosis* versus inhibition (toxicity) of human cells for these compounds (see second to right column of Tables 2 and 3).

Compound from Example 2 G26-$CH_3$ was found to have a selectivity index (SI) against *M. tuberculosis* of 4853 (see Table 3) compared to the best comparator compounds C4-Br and C6-Cl exhibiting selectivity indices of 320 and 363, respectively (see Table 2). Further, as seen in Table 3 the tuted benzoxaborole having a methyl substituent at the C-4 position of the benzoxaborole ring and an aminomethyl substituent at position C3 of the benzoxaborole ring has "(S)" relative stereochemistry at the stereocenter C with the aminomethyl substituent, and is surprisingly more selective for activity against *M. tuberculosis* than other substituted benzoxaboroles lacking some of these features as compared to inhibition (toxicity) of human cells for these compounds. In addition, the MIC values against *M. tuberculosis* H37Rv strain for Example. 2 G26-$CH_3$ is 0.2 μM, in contrast to other substituted benzoxaboroles being compared.

Thus, as seen in Table 3, compounds Example 2 G26-$CH_3$ was found surprisingly found to have a SI against *Mycobacterium tuberculosis* of 4853. This SI values are unexpectedly better than any of the comparator compounds set forth in Table 2.

Addition of an alkyl substituent at the C4 of the benzoxaborole ring thus confers an increase in the selectivity index compared to other substituted benzoxaboroles without an alkyl at the C4 of the benzoxaborole ring. Table 3 provides LeuRS inhibition IC50 values, MIC values against the *M. tuberculosis* standard strain Mtb H37Rv, toxicity values against human HepG2 cells, selectivity index (SI) values, and inhibition of protein synthesis values in mammalian cells for a substituted benzoxaborole of the invention wherein the compound (G26-$CH_3$, shown in the closed, tricyclic form) has a methyl at the C4 of the benzoxaborole ring and an aminomethyl substituent at position C3 of the benzoxaborole ring having "(S)" relative stereochemistry at that stereocenter.

As can be seen in Table 3, G26-$CH_3$ was also found to have good activity against leucyl tRNA synthetase from *M. tuberculosis* and exhibited low impact on mammalian cellular protein synthesis.

Surprisingly it has been found that certain substituted benzoxaboroles that are capable of existing in an equilibrium, in certain solvent conditions, between an open form and a closed form, wherein the compound in the closed form has a third ring involving the 1 and 7 positions of the benzoxaborole ring, exhibit an unexpected increase in the selectivity index. C4-Br, the (S) enantiomer of a substituted benzoxaborole comparator compound with a Br at the C4 position of the benzoxaborole ring that is not capable of existing in an equilibrium between an open form and a closed form in aqueous solvents, has an SI of 320, whereas C6-CI, the (S) enantiomer of a substituted-benzoxaborole with a CI at the C-4 position that is also not capable of existing in an equilibrium between an open form and a closed tricyclic form in aqueous solvents, has an SI of 363. This is in stark contrast to Example 2 G26-$CH_3$, the (S) enantiomer of a substituted benzoxaborole with a —$CH_3$ at the C-4 position that is capable of existing in an equilibrium between an open form and a closed form in aqueous solvents, has an SI of >4850.

If one compares the SI of Example 2 G26-$CH_3$ to the SI of C5-H, the (S) enantiomer of a substituted benzoxaborole comparator compound with a H at the C4 position of the benzoxaborole ring, one can see the SI of such a compound without a methyl substituent at C4 is only 3, indicating such a compound has very little selectivity for inhibiting *M. tuberculosis* compared to killing human cells. In contrast, Example 2 C26-$CH_3$, a compound with —$CH_3$ at the C4 position of the benzoxaborole ring which has been shown to exist in equilibrium between an open form and a closed form in aqueous solvents, has a selectivity index (SI) of >4850.

Certain substitutions of the substituted benzoxaboroles capable of existing, in certain environments, in equilibrium between an open form and a closed form thus confer an unexpected increase in the selectivity index. In contrast, comparator compounds C9-CI (a tricyclic benzoxaborole compound with a chloro substituent at C4 and —$CH_3$ substitution at $R^3$ and $R^4$ of the 7-membered ring) and C10-H (a tricyclic benzoxaborole compound with a hydrogen at C4 and —$CH_3$ substitution at $R^3$ and $R^4$ of the 7-membered ring) have SI indices of 10. This arguably indicates that substitution at the $R^3$ and $R^4$ positions is not favored for selectivity for *M. tuberculosis* versus inhibition (toxicity) of human cells for these particular compounds. It also suggests that the presence of a halogen at position C4 of the benzoxaborole ring (see C9-CI) is not sufficient to overcome the negative effect of methyl substitution at both $R^3$ and $R^4$ of the 7-membered tricyclic ring at the $R^3/R^4$ position.

Thus, the substituted benzoxaboroles of the invention, particularly Example 2 G26-$CH_3$, shows surprisingly higher SIs relative to the SIs of similar substituted benzoxaboroles for *M. tuberculosis* versus human cells.

It is to be understood that the invention covers all combinations of aspects with all other suitable aspects and/or exemplary embodiments described herein. It is to be understood that the invention also covers all combinations of exemplary embodiments with all other suitable aspects and/or exemplary embodiments described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having a structure as shown in Formula IIIa:

Formula III 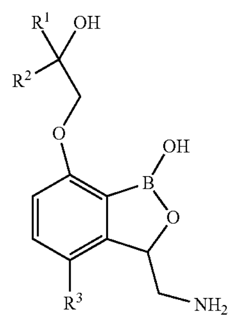 wherein $R^3$ is —$CH_3$; and $R^1$ and $R^2$ are each H, or a pharmaceutically acceptable salt thereof.

2. A pharmaceutical formulation, comprising:

a compound according to claim 1; and a pharmaceutically acceptable excipient, adjuvant or diluent.

3. A combination, comprising:

a first therapeutic agent or a pharmaceutically acceptable salt thereof, wherein the first therapeutic agent has the structure as shown below:

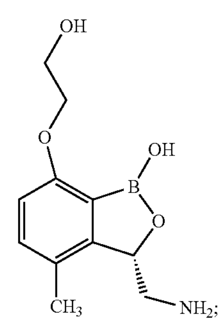 [SMILES: Cc1ccc(OCCO)c2c1[C@@H](CN)OB2O]

and a second therapeutic agent.

4. The combination according to claim 3, wherein the pharmaceutically acceptable salt is selected from a hydrochloride, a hydrobromide, a hydriodide, a nitride, a carbonate, a monohydrogencarbonate, a phosphate, a monohydrogenphosphate, a dihydrogenphosphate, a sulfate, a monohydrogensulfate, a dihydrogensulfate, or a phosphonate salt.

5. The combination according to claim 4, wherein the pharmaceutically acceptable salt is a hydrochloride salt or a dihydrogensulfate salt.

6. The combination according to claim 3, wherein the second therapeutic agent is independently selected from isoniazid, rifampin, pyrazinamide, ethambutol, moxifloxacin, rifapentine, clofazimine, bedaquiline (TMC207), nitroimidazo-oxazine PA-824, delamanid (OPC-67683), an oxazolidinone, EMB analogue SQ109, a benzothiazinone, and a dinitrobenzam ide.

7. The combination according to claim 6, wherein the second therapeutic agent is a therapeutic agent approved or recommended for the treatment of tuberculosis.

8. A method of treating a disease resulting from a mycobacterial infection in a mammal, which method comprises administering to the mammal in need of such treatment a therapeutically effective amount of a compound or a pharmaceutically acceptable salt according to claim 1,
wherein the mycobacterial infection is an infection of a mycobacterium selected from *Mycobacterium tuberculosis, Mycobacterium avium* including subspecies (subsp.) *Mycobacterium avium* subsp. *avium, Mycobacterium avium* subsp. *hominissuis, Mycobacterium avium* subsp. *silvaticum,* and *Mycobacterium avium* subsp. *paratuberculosis; Mycobacterium kansasii, Mycobacterium malmoense, Mycobacterium simiae, Mycobacterium szulgai, Mycobacterium xenopi, Mycobacterium scrofulaceum, Mycobacterium abscessus, Mycobacterium chelonae, Mycobacterium haemophilum, Mycobacterium leprae, Mycobacterium marinum, Mycobacterium fortuitum, Mycobacterium parafortuitum, Mycobacterium gordonae, Mycobacterium vaccae, Mycobacterium bovis, Mycobacterium bovis* BCG, *Mycobacterium africanum, Mycobacterium canetti, Mycobacterium caprae, Mycobacterium microti, Mycobacterium pinnipedi, Mycobacterium leprae, Mycobacterium ulcerans, Mycobacterium intracellulare, Mycobacterium tuberculosis* complex (MTC), *Mycobacterium avium* complex (MAC), *Mycobacterium avian*—intracellulare complex (MAIC), *Mycobacterium gordonae*clade; *Mycobacterium kansasii* clade; *Mycobacterium chelonae* clade; *Mycobacterium fortuitum* clade; *Mycobacterium parafortuitum* clade; and *Mycobacterium vaccae* clade.

9. A method of treating a disease resulting from a mycobacterial infection in a mammal, which method comprises administering to the mammal in need of such treatment a therapeutically effective amount of a compound having a structure as shown:

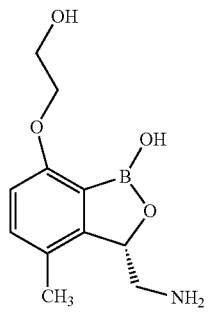 [SMILES: Cc1ccc(OCCO)c2c1[C@@H](CN)OB2O]

or a pharmaceutically acceptable salt thereof, wherein the mycobacterial infection is an infection of a mycobacterium selected from *Mycobacterium tuberculosis* and *Mycobacterium avium.*

10. The method according to claim 9, wherein the mycobacterial infection is a *Mycobacterium tuberculosis* infection.

11. The method according to claim 10, wherein the disease is *tuberculosis.*

12. The method according to claim 11, wherein the mammal is a human.

13. The method according to claim 9, wherein the mycobacterial infection is a *Mycobacterium avium* infection.

14. The method according to claim 13, wherein the disease is Johne's disease, Crohn's disease, pulmonary disease or pulmonary infection, Lady Windermere syndrome, *Mycobacterium avium* complex (MAC) lung disease, disseminated *Mycobacterium avium* complex (DMAC), disseminated *Mycobacterium avium* intracellulare complex (DMAIC), hot-tub lung, MAC mastitis, MAC pyomyositis, *Mycobacterium avum paratuberculosis* or granuloma disease.

15. A method of treating a disease resulting from a mycobacterial infection in a mammal, which method comprises:
administering to the mammal in need of such treatment a first therapeutic agent that is a therapeutically effective amount of a compound having a structure as shown:

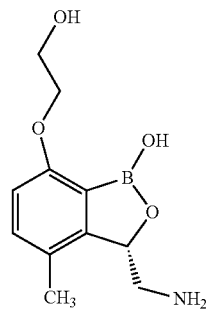 [SMILES: Cc1ccc(OCCO)c2c1[C@@H](CN)OB2O]

or a pharmaceutically acceptable salt thereof,
wherein the mycobacterial infection is an infection of a mycobacterium selected from *Mycobacterium tuberculosis* and *Mycobacterium avium*; and
administering a second therapeutic agent,
wherein the second therapeutic agent is not the first therapeutic agent or a pharmaceutically acceptable salt thereof.

16. The method of claim 15, wherein the second therapeutic agent is independently selected from isoniazid, rifampin, pyrazinamide, ethambutol, moxifloxacin, rifapentine, clofazimine, bedaquiline (TMC207), nitroimidazo-oxazine PA-824 (pretomanid), delamanid (OPC-67683), an oxazolidinone, EMB analogue SQ109, a benzothiazinone, and a dinitrobenzamide.

17. The method of claim 16, wherein the oxazolidinone is linezolid, tedizolid, radezolid, sutezolid (PNU-100480), or posizolid (AZD-5847).

18. The method of claim 15, wherein the second therapeutic agent is selected from a therapeutic agent approved or recommended for the treatment of tuberculosis.

19. A method of treating a disease resulting from a mycobacterial infection in a mammal, which method comprises administering to the mammal in need of such treatment a therapeutically effective amount of a pharmaceutical formulation according to claim 2, wherein the mycobacterial infection is an infection of a mycobacterium selected from *Mycobacterium tuberculosis, Mycobacterium avium* including subspecies (subsp.) *Mycobacterium avium* ; subsp. *avium, Mycobacterium avium*subsp. *hominissuis, Mycobacterium avium* subsp. *silvaticum,* and *Mycobacterium avium* subsp. *paratuberculosis; Mycobacterium kansasii, Mycobacterium malmoense, Mycobacterium simiae, Mycobacterium szulgai, Mycobacterium xenopi, Mycobacterium scrofulaceum, Mycobacterium abscessus, Mycobacterium chelonae, Mycobacterium haemophilum, Mycobacterium leprae, Mycobacterium marinum, Mycobacterium fortuitum, Mycobacterium parafortuitum, Mycobacterium gordonae, Mycobacterium vaccae, Mycobacterium bovis, Mycobacterium bovis*BCG, *Mycobacterium africanum, Mycobacterium canetti, Mycobacterium caprae, Mycobacterium microti, Mycobacterium pinnipedi, Mycobacterium leprae, Mycobacterium ulcerans, Mycobacterium intracellulare, Mycobacterium tuberculosis* complex (MTC), *Mycobacterium avium* complex (MAC), *Mycobacterium avian*-intracellulare complex (MAIC), *Mycobacterium gordonae*clade; *Mycobacterium kansasii* clade; *Mycobacterium chelonae* clade; *Mycobacterium fortuitum* clade; *Mycobacterium parafortuitum* clade; and *Mycobacterium vaccae* clade.

20. A method of treating a disease resulting from a mycobacterial infection in a mammal, which method comprises administering to the mammal in need of such treatment a therapeutically effective amount of a combination according to claim 3, wherein the mycobacterial infection is an infection of a mycobacterium selected from *Mycobacterium tuberculosis, Mycobacterium avium* including subspecies (subsp.) *Mycobacterium avium* subsp. *avium, Mycobacterium avium* subsp. *hominissuis, Mycobacterium avium* subsp. *silvaticum,* and *Mycobacterium avium* subsp. *paratuberculosis; Mycobacterium kansasii, Mycobacterium malmoense, Mycobacterium simiae, Mycobacterium szulgai, Mycobacterium xenopi, Mycobacterium scrofulaceum, Mycobacterium abscessus, Mycobacterium chelonae, Mycobacterium haemophilum, Mycobacterium leprae, Mycobacterium marinum, Mycobacterium fortuitum, Mycobacterium parafortuitum, Mycobacterium gordonae, Mycobacterium vaccae, Mycobacterium bovis, Mycobacterium bovis* BCG, *Mycobacterium africanum, Mycobacterium canetti, Mycobacterium caprae, Mycobacterium microti, Mycobacterium pinnipedi, Mycobacterium leprae, Mycobacterium ulcerans, Mycobacterium intracellulare, Mycobacterium tuberculosis* complex (MTC), *Mycobacterium avium* complex (MAC), *Mycobacterium avian*-intracellulare complex (MAIC), *Mycobacterium gordonae* clade; *Mycobacterium kansasii* clade; *Mycobacterium chelonae* clade; *Mycobacterium fortuitum* clade; *Mycobacterium parafortuitum* clade; and *Mycobacterium vaccae* clade.

21. The combination according to claim 3, wherein the second therapeutic agent is an antiretroviral agent.

22. The method according to claim 15, wherein the second therapeutic agent is an antiretroviral agent.

23. The combination according to claim 21, wherein the antiretroviral agent is zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, or darunavir.

24. The method of claim 22, wherein the antiretroviral agent is zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, or darunavir.

25. The method of claim 24, wherein the antiretroviral agent is GSK1349572 or GSK1265744.

\* \* \* \* \*